United States Patent
Bennett et al.

(10) Patent No.: US 6,541,604 B1
(45) Date of Patent: *Apr. 1, 2003

(54) LEPTIN RECEPTOR HAVING A WSX MOTIF

(75) Inventors: Brian Bennett, Pacifica, CA (US); William Matthews, Woodside, CA (US)

(73) Assignee: Genentech, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/780,562

(22) Filed: Jan. 8, 1997

Related U.S. Application Data

(60) Provisional application No. 60/064,855, filed on Jan. 8, 1996.

(51) Int. Cl.⁷ ............................................. C07K 14/705
(52) U.S. Cl. ..................................................... 530/350
(58) Field of Search ............................... 530/350, 351, 530/402; 514/2, 8, 12

(56) References Cited

U.S. PATENT DOCUMENTS

| | | | |
|---|---|---|---|
| 5,116,951 A | * 5/1992 | Druez et al. ................ | 530/385 |
| 5,264,416 A | * 11/1993 | Park et al. .................. | 435/69.1 |
| 5,349,053 A | 9/1994 | Landolfi | |
| 5,378,808 A | 1/1995 | D'Andrea et al. .......... | 530/350 |
| 5,453,491 A | * 9/1995 | Takatsu et al. ............. | 530/350 |
| 5,521,283 A | 5/1996 | DiMarchi et al. | |
| 5,532,336 A | 7/1996 | DiMarchi et al. | |
| 5,543,320 A | 8/1996 | Park et al. | |
| 5,569,744 A | 10/1996 | Basinski et al. | |
| 5,571,513 A | 11/1996 | Burstein | |
| 5,580,954 A | 12/1996 | DiMarchi et al. | |
| 5,599,905 A | * 2/1997 | Masley et al. .............. | 530/350 |
| 5,605,886 A | 2/1997 | Basinski et al. | |
| 5,635,177 A | 6/1997 | Bennett et al. | |
| 5,635,388 A | 6/1997 | Bennett et al. | |
| 5,639,605 A | * 6/1997 | Kitamurn et al. ............... | 435/6 |
| 5,643,748 A | * 7/1997 | Snodgrass et al. ......... | 435/69.1 |
| 5,670,373 A | 9/1997 | Kishimoto et al. | |
| 5,698,389 A | 12/1997 | de la Brousse et al. | |
| 5,763,211 A | 6/1998 | Snodgrass et al. | |
| 5,827,734 A | 10/1998 | Weigle et al. .............. | 435/325 |
| 5,856,098 A | 1/1999 | Snodgrass et al. ............. | 435/6 |
| 5,858,967 A | 1/1999 | Weigle et al. .................. | 514/2 |
| 5,869,610 A | 2/1999 | Snodgrass et al. .......... | 530/350 |
| 5,882,860 A | 3/1999 | Snodgrass et al. ............. | 435/6 |
| 5,912,123 A | 6/1999 | Snodgrass et al. ............. | 435/6 |
| 5,935,810 A | 8/1999 | Friedman et al. ........... | 435/69.1 |
| 5,968,779 A | 10/1999 | Campfield et al. ......... | 435/69.4 |
| 5,972,621 A | * 10/1999 | Tartaglia et al. ............. | 435/7.1 |
| 6,001,968 A | 12/1999 | Friedman et al. ........... | 530/350 |
| 6,005,080 A | 12/1999 | Snodgrass et al. ....... | 530/387.9 |
| 6,124,439 A | 9/2000 | Friedman et al. ...... | 530/388.24 |
| 2002/0037553 A1 | 3/2002 | Al-Barazanji et al. ..... | 435/69.1 |

FOREIGN PATENT DOCUMENTS

| | | |
|---|---|---|
| EP | 372752 | 6/1990 |
| EP | 0396 387 A3 | 11/1990 |
| EP | 0 396 387 A2 | 11/1990 |
| EP | 0 741 187 A2 | 11/1996 |
| EP | 0 956 862 A1 | 11/1999 |
| WO | WO 91/01004 | 1/1991 |
| WO | WO 91/01743 | 2/1991 |
| WO | WO 94/05332 | 3/1994 |
| WO | WO 94/11404 | 5/1994 |
| WO | WO 95/14930 | 6/1995 |
| WO | PCT/GB96/01388 | 6/1995 |
| WO | WO 95/21864 | 8/1995 |
| WO | WO 96/03438 | 2/1996 |
| WO | WO 96/05309 | 2/1996 |
| WO | WO 96/08510 | 3/1996 |
| WO | WO 96/23517 | 8/1996 |
| WO | WO 96/24670 | 8/1996 |
| WO | WO 96/31526 | 10/1996 |
| WO | WO 96/34885 A3 | 11/1996 |
| WO | WO 96/34885 A2 | 11/1996 |
| WO | WO 97/00319 | 1/1997 |
| WO | WO 97/12037 | 4/1997 |
| WO | WO 97/19952 | 6/1997 |

(List continued on next page.)

OTHER PUBLICATIONS

H. Baumann et al., "The full–length leptin receptor has signaling capabilities of interleukin 6–type cytokine receptors," *Proc. Natl. Acad. Sci. USA*, vol. 93, pp. 8374–8378 (Aug. 1996).

B. D. Bennett et al., "A role for leptin and its cognate receptor in hematopoiesis," *Current Biology*, vol. 6, No. 9, pp. 1170–1180 (1996).

B. Burguera et al., "The Long Form of the Leptin Receptor (OB–Rb) is Widely Expressed in the Human Brain," *Neuroendocrinology*, vol. 61, pp. 187–195 (2000).

S. C. Chua Jr. et al., "Phenotypes of Mouse diabetes and Rat fatty Due to Mutations in the OB (Leptin) Receptor," *Science*, vol. 271, pp. 994–996 (Feb. 16, 1996).

N. Hoggard et al., "Ontogeny of the expression of leptin and its receptor in the murine fetus and placenta," *British Journal of Nutrtion*, vol. 83, pp. 317–326 (2000).

S–M Luoh et al., "Cloning and characterization of a human leptin receptor using a biologically ctive leptin immunoadhesin," *Journal of Molecular Endocrinology*, vol. 18, pp. 77–85 (1997).

(List continued on next page.)

Primary Examiner—John Ulm
(74) Attorney, Agent, or Firm—Knobbe, Martens, Olson & Bear LLP.

(57) ABSTRACT

The WSX receptor, WSX receptor extracellular domain (ECD), WSX receptor variants, chimeric WSX receptor (e.g., WSX receptor immunoadhesin), and antibodies which bind thereto (including agonist and neutralizing antibodies) are disclosed. Various uses for these molecules are described.

1 Claim, 45 Drawing Sheets

FOREIGN PATENT DOCUMENTS

| WO | WO 97/25424 | 7/1997 | |
| --- | --- | --- | --- |
| WO | WO 97/26272 | 7/1997 | |
| WO | WO 97/26335 | 7/1997 | |
| WO | WO 97/26370 | 7/1997 | |
| WO | WO 97/26523 | 7/1997 | |
| WO | WO 97/27286 | 7/1997 | |
| WO | WO 97/41217 | 11/1997 | |
| WO | WO 97/41263 | 11/1997 | |
| WO | WO 97/48419 | 12/1997 | A61K/48/00 |
| WO | WO 97/48806 | 12/1997 | C12N/15/16 |
| WO | 98/18486 | 5/1998 | |
| WO | WO 98/28427 | 7/1998 | C12N/15/62 |

OTHER PUBLICATIONS

Shin et al., *Hybrid Antibodies*, Intern. Rev. Immunol. vol. 10, pp. 177–186 (1993).

U.S. patent application Ser. No. 08/895,626, Avraham et al., filed Jul. 17, 1997.

Arai et al., "Molecular Biology of T–Cell–derived Lymphokines: A Model system for Proliferation and Differentiation of Hemopoietic Cells" *BioEssay* 5(4):166–71 (Oct. 1986).

Bruno et al., "Effect of Recombinant and Purified Hematopoietic Growth Factors on Human Megakaryocyte Colony Formation" *Exp. Hematol.* 16:371–377 (1988).

Cosman, D. et al., "A New Cytokine Receptor Superfamily" *Trends Biochem. Sci.* 15:265–270 (1990).

Francis, G., "Protein modification and fusion proteins" *Focus on Growth Growth Factors* 3:4–10 (1997).

Gainsford et al., "Leptin can induce proliferation, differentiation, and functional activation of hemopoietic cells" *Proc. Natl. Acad. Sci. USA* 93:14564–14568 (Dec. 1996).

Ishizaka et al., "Preferential Differntiation of Inflammatory Cells by Recombinant Human Interleukins" *Int. Arch Allergy Appl Immunol* 88:46–49 (1989).

Koike et al., "Synergism of BSF–2/Interleukin 6 and Interleukin 3 on Development of Multipotential Hemopoietic Progenitors in Serum–Free Culture" *Journal of Experimental Medicine* 168:879–890 (1988).

Migliaccio et al., "Effect of Recombinant Hematopoietic Growth Factors on Proliferation of Human Marrow Progenitor Cells in Serum–Deprived Liquid Culture" *Blood* 72(3):1387–1392 (1988).

Shin et al., "Hybrid Antibodies" *Intern. Rev. Immunol.* 10:177–186 (1993).

Ashkenazi et al., "Protection Against Endotoxic Shock by a Tumor Necrosis Factor Receptor Immunoadhesion" *Proc. Natl. Acad. Sci.* 88:10535–10539 (1991).

Barinaga, M., "Obesity: Leptin Receptor Weighs In" *Science* 271:29 (Jan. 5, 1996).

Bennet et al., "A role for Leptin and its cognate receptor in hematopoiesis" *Current Biology* 6(9):1170–1180 (Sep. 1, 1996).

Genbank, "Release 100" *Homo sapiens cDNA clone 84708 5'* (Mar. 2, 1995).

Kaczmarski *Blood Review* 5(3) 1991, p 193–203.*

Casman *Cytokine* 5(2) 1993, p 95–106.*

Shields et al *Cytokine* 7(7) 1995, p 679–88.*

*Antibodies, A Laboratory Manual,* Harlow and Lane, Cold Spring Harbor Laboratory pps. 341 (1988).

"Polyethylene glycol and derivatives" *Catalog Shearwater Polymers, Inc., Functionalized Biocompatible Polymers for Research* (Jan. 1994).

Ashkenazi and Chamow, "Immunoadhesins: An Alternative to Human Monoclonal Antibodies" *Methods: A Companion to Methods in Enzymology* 8:104–115 (1995).

Barin, Marcia, ""Obese" protein slims mice" *Science* 269:475–476 (1995).

Baumann et al., "Multiple regions within the cytoplasmic domains of the leukemia inhibitory factor receptor and gp130 cooperate in signal transduction in hepatic and neuronal cells" *Molecular & Cellular Biology* 14(1):138–146 (1994).

Beck et al., "Generation of soluble interleukin–1 receptor from an immunoadhesin by specific cleavage" *Molecular Immunology* 31(17):1335–1344 (1994).

Bennett et al., "Extracellular Domain–IgG Fusion Proteins for Three Human Natriuretic Peptide Receptors. Hormone Pharmacology and Application to Solid Phase Screening of Synthetic Peptide Antisera" *The Journal of Biological Chemistry* 266(34):23060–23067 (Dec. 5, 1991).

Campfield et al., "Recombinant mouse ob protein: evidence for a peripheral signal linking adiposity and central neural networks" *Science* 269:546–549 (1995).

Carter et al. *Mutagenesis, A Practical Approach,* Mcpherson,ed., Oxford, UK:IRL Press vol. Chapter 1:1–25 (1991).

Carter et al., "Engineering Subtilisin BPN' for Site–Specific Proteolysis" *Proteins: Struct. Funct., Genet.* 6:240–248 (1989).

Carter et al., "Humanization of an anti–p185$^{HER2}$ antibody for human cancer therapy" *Proc. Natl. Acad. Sci.* 89:4285–4289 (1992).

Chen et al., "Evidence that the diabetes gene encodes the leptin receptor: identification of a mutation in the leptin receptor gene in db/db mice" *Cell* 84:491–495 (1996).

Cioffi et al., "Novel B219/OB receptor isoforms: possible role of leptin in hematopoiesis and reproduction" *Nature* 2(5):585–589 (1996).

Colditz, G.A., "Economic costs of obesity" *Am. J. Clin. Nutr.* 55:503S–507S (1992).

Coleman and Hummal, "Effects of parabiosis of normal with genetically diabetic mice" *Am. J. Physiol.* 217:1298–1304 (1969).

Coleman et al., "Obese and Diabetes: Two Mutant Genes Causing Diabetes–Obesity Syndromes in Mice" *Diebetologia* 14:141–148 (1978).

Coleman, D.L., "Effects of parabiosis of obese with diabetes and normal mice" *Diabetol* 9:294–298 (1973).

Considine, R. et al., "Serum immunoreactive–leptin concentrations in normal–weight and obese humans" *The New England Journal of Medicine* pps. 292–295 (Feb. 1, 1996).

D'Andrea, A.D., "Cytokine receptors in congenital hematopoietic disease" *New England J. of Medicine* 330(12):839–846 (1994).

Dexter et al., "Growth and Differentiation in the Hemopoietic System" *Ann. Rev. Cell Biol.* 3:423–441 (1987).

Eisenberg, R., "Structure and Function in Gene Patenting" *Nature Genetics* 15:125–129 (1997).

Friedman et al., "Molecular mapping of the mouse ob mutation" *Genomics* 11:1054–1062 (1991).

Fukunaga R. et al., "Functional domains of the granulocyte colony–stimulating factor receptor" *EMBO Journal* 10(10):2855–2865 (1991).

Griffiths et al., "Isolation of High Affinity Human Antibodies Directly From Large Synthetic Repertoires" *EMBO Journal* 13:3245–3260 (1994).

Grupe et al., "Transgenic Knockouts Reveal a Critical Requirement for Pancreatic β Cell Glucokinase in Maintaining Glucose Homeostasis" *Cell* 83:69–78 (1995).

Halaas et al., "Weight–reducing effects of the plasma protein encoded by the obese gene" *Science* 269:543–546 (1995).

Hardy et al., "Resolution and characterization of pro–B and pre–pro–B cell stages in normal mouse bone marrow" *Journal of Experimental Medicine* 173:1213–1225 (1991).

Hillier et al., "WashU–Merck EST Project" *GenBank* (1995).

Holmes et al., "Structure and Functional Expression of a Human Interleukin–8 Receptor" *Science* 253(5025):1278–1280 (Sep. 13, 1991).

Humphries et al., "Self–Renewal of Hemopoietic Stem Cells During Mixed Colony Formation in Vitro" *Proc. Natl. Acad. Sci.* 78:3629–3633 (1981).

Kim et al., "Detection of Human Leukemia Inhibitory Factor by Monoclonal Antibody Based ELISA" *Journal of Immunological Methods* 156:9–17 (1992).

Kishimoto, "Cytokine Signal Transduction" *Cell* 76:253–262 (Jan. 28, 1994).

Kuczmarski et al., "Increasing prevalence of overweight among US adults" *J. Am. Med. Assoc.* 272(3):205–211 (1994).

Laskov et al., "Extinction of B–cell surface differentiation markers in hybrids between murine B–lymphoma and myeloma cells" *Cellular Immunology* 55(2):251–264 (1980).

Lee, G. et al., "Abnormal splicing of the leptin receptor in diabetic mice" *Nature* 379:632–635 (Feb. 1996).

Levin et al., "Decreased Food Intake Does Not Completely Account For Adiposity Reduction After ob Protein Infusion" *Proc. Natl. Acad. Sci.* 93:1726–1730 (1996).

Maffei et al., "Increased expression in adipocytes of ob RNA in mice with lesions of the hypothalamus and with mutations at the db locus" *Proc. Natl. Acad. Sci.* 92:6957–6960 (1995).

Mark et al., "rse, a Novel Receptor–type Tyrosine Kinase with Homology to Axl/Ufo, Is Expressed at High Levels in the Brain" *Journal of Biological Chemistry* 269(14):10720–10728 (Apr. 8, 1994).

McNiece et al., "The role of recombinant stem cell factor in early B cell development. Synergistic interaction with IL–7" *J. Immunol.* 146:3785–3790 (1991).

Miyajima et al., "Receptors for Granulocyte–Macrophage Colony–Stimulating Factor, Interleukin–3, and Interleukin–5" *Blood* 82(7):1960–1974 (Oct. 1, 1993).

Murakami et al., "Critical cytoplasmic region of the interleukin 6 signal transducer gp130 is conserved in the cytokine receptor family" *Proc. Natl. Acad. Sci. USA* 88:11349–11353 (Dec. 1991).

Nicola, N., "Cytokine Pleiotrophy and Redundancy: A View From the Receptor" *Stem Cells* 12(Suppl.1):3–12 (1994).

Pelleymounter et al., "Effects of the obese gene product on body weight regulation in ob/ob mice" *Science* 269:540–543 (1995).

Pi–Sunyer, F.X., "Medical Hazards of Obesity" *Anns. Int. Med.* 119:655–660 (1993).

Rink, Timothy J., "In search of a satiety factor" *Nature* 372:406–407 (1994).

Stewart et al., "Induction of Type 1 Diabetes by Interferon–A in Transgenic Mice" *Science* 260:1942–1946 (1993).

Suva et al., "A parathyroid hormone–related protein implicated in malignant hypercalcemia: cloning and expression" *Science* 237(4817):893–896 (Aug. 1987).

Tartaglia et al., "Identification and expression cloning of a leptin receptor, ob–r" *Cell* 83:1263–1271 (1995).

Tavassoli, M., "Lodgement of haemopoietic cells in the course of haemopoiesis on cellulose ester membrane: an experimental model for haemopoietic cell trapping" *Brit. J. Haematology* 57:71–80 (1984).

Vaisse et al., "Leptin Activation of Stat3 in the Hypothalamus of Wild–Type and ob/ob Mice But Not db/db Mice" *Nature Genetics* 14:95–97 (1996).

Vaughan et al., "Human Antibodies With Sub–nanomolar Affinities Isolated From a Large Non–immunized Phage Display Library" *Nature Biotechnology* 14:309–314 (1996).

Wells, J., "Structural and functional basis for hormone binding and receptor oligomerization" *Cell Biology* 6:163–173 (1994).

Zeigler et al., "Cellular and Molecular Characterization of the Role of the FLK–2/FLT–3 Receptor Tyrosine Kinase in Hematopoietic Stem Cells" *Blood* 84(8):2422–2430 (1994).

Zhang et al., "Positional cloning of the mouse obese gene and its human homologue" *Nature* 372:425–431 (1994).

\* cited by examiner

```
sites: std
length: 4102 (circular)

pleI
              hinfI
        xhoI  salI
        paeR7I  taqI                                           alui
        ecoRI tagI hincII/hindII tru9I                                                         eco57I
        apoI aval accI  acII  mseI                                                              bsII                                              foki       ddeI       mnlI
    1 GAATTCTCGA GTCGACGGCG GGCGTTAAAG CTCTCCGTGGC ATTATCCTTC AGTGGGGCTA TTGGACTGAC TTTTCCTTATG CTGGGATGTG CCTTAGAGGA
      CTTAAGAGCT CAGCTGCCGC CCGCAATTTC GAGAGCACCG TAATAGGAAG TCACCCCGAT AACCTGACTG AAAAGGAATAC GACCCTACAC GGAATCTCCT rsaI                                                                                                  tru9I
         csp6I  eco57I                                       apoI          maeIII         apoI                 mseI
    101 TTATGGGTGT ACTTCTCTGA AGTAAGATGA TTTGTCAAAA ATTCTGTGTG GTTTGTTAC ATTGGAATT TATTTATGTG ATAACTCGT TTAACTTGTC
        AATACCCACA TGAAGAGACT TCATTCTACT AAACAGTTTT TAAGACACAC CAAACAATG TAACCCTTAA ATAAATACAC TATTGACGCA AATTGAACAG
      1                 M  I    C   Q   K    F   C    V   V   L   L   H    W   E   F    I   Y   V    I   T   A    F   N   L   S nlaIII
                                 sphI
                                 nspI
                         tru9I   nspHI            apoI
              styI       mseI
              bsaJI
    201 ATATCCAATT ACTCCTTGGA GATTAAGTT GTCTTGCATG CCACCAAATT CAACCTATGA CTACTTCCTT TTGCCTGCTG GACTCTCAAA GAATACTTCA
        TATAGGTTAA TGAGGAACCT CTAAATTCAA CAGAACGTAC GGTGGTTTAA GTTGGATACT GATGAAGGAA AACGGACGAC CTGAGAGTTT CTTATGAAGT
      26 Y   P   I    T   P   W   R    F   K   L    S   C   M    P   P   N   S    T   Y   D    Y   F   L    L   P   A   G    L   S   K    N   T   S taqI
              sfuI
              bstBI
              bsiCI              pvuII                                                                           pleI
              asuII              nspBII                   tru9I                                                  hinfI
                         bsmAI  aluI    ddeI              mseI                                                              apoI
    301 AATTCGAATG GACATTATGA GACAGCTGTT GAACCTAAGT TTAATTCAAG TGGTACTCAC ACCATGAGTG AAAAGATTGA ATAGGTTTTG TTGAAAGGTG ACAACGAAAG
        TTAAGCTTAC CTGTAATACT CTGTCGACAA CTTGGATTCA AATTAAGTTC ACCATGAGTG TGGTACTCAC TTTTCTAACT TATCCAAAAC AACTTTCCAC TGTTGCTTTC
      59 N   S   N   G    H   Y   E    T   A   V    E   P   K    F   N   S    S   G   T    H   T   M   S    E   K   I    D   R   L    L   K   R sfaNI
    401 GGAGTGAGCA AGATAGAAAC TGCTCCTTAT GTGCAGACAA CATTGAAGGA AAGACATTTG TTTCAACAGT GTTTTTCAAC AAATAGATGC
        CCTCACTCGT TCTATCTTTG ACGAGGAATA CACGTCTGTT GTAACTTCCT TTCTGTAAAC AAAGTTGTCA CAAAAGTTG TTTATCTACG
      93 S  E   Q    D   R   N    C   S   L   C    A   D   N    I   E   G    K   T   F    V   S   T    V   F   Q   Q     I   D   A
```

```
                                                                                                                              ddeI
                                                                                                   ecoRI                                                      bsmAI aluI fokI
                    rsaI                                                                            apoI                   alul       drdI      CAAGATTGTC TCAGCTACAT
                    csp6I                                                                           AATATTCAGA  ACAGTTATCA GAGAAGCTGA                         AGTCGATGTA
                    nlaIV                                                              sspI         GAATTCACA                                    GTTCTAACAG
                    kpnI                                                                TATCAAGTGA  CTTAAGATGT  TGTCAATAGT CTCTTCGACT
                    hgiCI                                              TCCACTTTCAA                                                                K   I  V    S   A  T   S
                    banI                                                                ATAGTTCACT  N   S    T   T  V   I   R    E   A    D
                    asp718                            AGGTACCATT       AGGTGAAGTT       Y   S   E                 ^begin12u
              bslI   acc65I               TGGTACCATT  TCGGGTTGGTA      P   L   Q
    901  AGCCCACCAT  ACCATGGTA   V   P  F
    259  TCGGGTGGTA  P   P   L                                                                                         tfiI
         S   P   P                                                                                                     scrFI
                                                                                                                       mvaI
                                                                                                                       ecoRII
                                                                                            bpuAI                       dsaV
                                                                                           scrFI                        bstXI                    bstNI
                                                                                           mvaI bbsI                                             apyI[dcm+]
                                                                                           ecoRII                                                sau96I       rsaI
                                                                                           dsaV                                                                        bsrI       csp6I
                                                                                           bstNI                                                                        maeIII    scaI
                                              accI                                                                       haeIII/palI            hinfI  gsuI/bpmI gsuI/bpmI  mnlI
                                              rmaI bst1107I bsaJI mboII                                mnlI                                             TGGAGTGACT GGAGTACTCC
                                              maeI accI      apyI[dcm+]             mnlI hphI  bsmAI fokI bsaJI   CCCAGGAATC CTGACCTACC        bsrI asuI   ACCTCACTGA CCTCATGAGG
    1001 CCCTGCTAGT AGACAGTATA CTTCCTGGGT CTTCGTATGA GGTTCAGGTG AGGGGCAAGA  GACTGGATGG          CCAAGTCCAC GAAGCATACT   CTGACCTTCT CCGTTCT       CCCCGTTCT  CCTGACCTTC
                                                                                                                                                          CCCCCGTTCT
         GGGACGATCA TCTGTCATAT GAAGGACCCA GAAGCATACT CCAAGTCCAC GAAGCATACT              CCCCGTTCT CTGACCTACC GGTCCTTAG ACCTCACTGA CCTCATGAGG
    293  L   L   V  D   S   I  L   P   G   S   S   Y   E   V   Q   V   R   G   K   R    L   D    G   P   G   I   W    S   D    W   S   T     P apoI                                               sfaNI
    1101 TCGTGTCTTT ACCACACAAG ATGTCATATA CTTTCCACCT AAAATTCTGA                    CAAGTGTTGG GTCTAATGTT TCTTTTCACT    GCATCTATAA GAAGGAAAAC
         AGCACAGAAA TGGTGTGTTC TACAGTATAT GAAAGGTGGA TTTTAAGACT                    GTTCACAACC CAGATTACAA AGAAAAGTGA    CGTAGATATT CTTCCTTTTG
    326  R   V   F  T   T   Q   D   V   I   Y   F   P   P   K   I   L   T   S    V   G    S   N   V    S   F   H   C    I   Y    K   K   E  N
```

FIG. 1C

```
                                                                                                                    nlaIII
                                                                                                                    sau3AI
                                                                                                                    mboI/ndeII[dam-]
                                                                                                                    dpnI[dam+]
                                                                                                                    dpnII[dam-]
                                                                                   apoI  .ddeI                       bclI[dam-]                    maeIII
              mnlI              foki          alui  apoI  mnlI            bsrI
1201 AAGATTGTTC CCTCAAAAGA GATTGTTTGG TGGATGAATT TAGCTGAGAA AATTCCTCAA AGCCAGTATG ATGTTGTGAG TGATCATGTT AGCAAAGTTA
     TTCTAACAAG GGAGTTTTCT CTAACAAACC ACCTACTTAA ATCGACTCTT TTAAGGAGTT TCGGTCATAC TACAACACTC ACTAGTACAA TCGTTTCAAT
359   K  I  V  P   S  K  E   I  V  W   M  N  L    A  E  K    I  P  Q    S  Q  Y  D   M  V  V  S   D  H  V   S  K  V  T rsaI    fnu4HI               bsmI
           taqI                                                   csp6I   bbvI                 nlaIII
           xhoI                               sfaNI
           paeR7I
           avaI
           mnlI    mnlI
1301 CTTTTTTCAA TCTGAATGAA ACCAAACCTC GAGGAAAGTT TACCTATGAT GCAGTGTACT GCTGCAATGA ACATGAATGC CATCATCGCT ATGCTGAATT
     GAAAAAAGTT AGACTTACTT TGGTTTGGAG CTCCTTTCAA ATGGATACTA CGTCACATGA CGACGTTACT TGTACTTACG GTAGTAGGA TACGACTTAA
393  F  F  N    L  N  E    T  K  P  R   G  K  F   T  Y  D    A  V  Y  C   C  N  E    H  E  C   H  H  R  Y   A  E  L tru9I                                                          rsaI
                                          mseI                                                           csp6I
                                          rsaI                                                                       bsrI          maeIII
                                          csp6I                                             hincII/hindII            bsrI          aciI
1401 ATATGTGATT GATGTCAATA TCAATATCTC ATGTGAAACT GATGGGTACT TAACTAAAAT GACTTGCAGA TGTCAACCA GTACAATCCA GTCACTTGCG
     TATACACTAA CTACAGTTAT AGTTATAGAG TACACTTTGA CTACCCATGA ATTGATTTTA CTGAACGTCT ACCAGTTGGT CATGTTAGGT CAGTGAACGC
426  Y  V  I    D  V  N  I   N  I  S    C  E  T   D  G  Y  L   T  K  M   T  C  R    W  S  T  S   T  I  Q    S  L  A hgiJII
                                                                                                     bsp1286
                                                                                                     bmyI
                    muni1 mnlI                    fnu4HI                                                  banI
                                                  bbvI                                  fokI             ddeI
1501 GAAAGCACTT TGCAATTGAG GTATCATAGG AGCAGCCTTT ACTGTTCTGA TATTCCATCT ATTCATCCCA TATCTGAGCC CAAAGATTGC TATTTGCAGA
     CTTTCGTGAA ACGTTAACTC CATAGTATCC TCGTCGGAAA TGACAAGACT ATAAGGTAGA TAAGTAGGGT ATAGACTCGG GTTTCTAACG ATAAACGTCT
459  E  S  T  L   Q  L  R    Y  H  R    S  S  L  Y   C  S  D    I  P  S    I  H  P  I   S  E  P    K  D  C   Y  L  Q  S

FIG. 1D
```

```
                                                    sau3AI
                                                    mboI/ndeII[dam-]
                                                     dpnI[dam+]
                                                      dpnII[dam-]
                                                       alwI[dam-]
                                      mamI[dam-]                                              rmaI         pleI
              ppu10I                  bsaBI[dam-]                                             maeI         hinfI
              nsiI/avaIII                    draIII
              bsmI                mboII
1601 GTGATGGTTT TTATGAATGC ATTTTCCAGC CAATCTTCCT ATTATCTGGC TACACAATGT GGATTAGGAT CAATCACTCT CTAGGTTCAC TTGACTCTCC
     CACTACCAAA AATACTTACG TAAAAGGTCG GTTAGAAGGA TAATAGACCG ATGTGTTACA CCTAATCCTA GTTAGTGAGA GATCCAAGTG AACTGAGAGG
 493  D  G  F   Y  E  C   I  F  Q   P  I  F  L   L  S  G   Y  T  M  W   I  R  I   N  H  S   L  G  S  L   D  S  P
         ^beginl3-2
         nlaIII
         nspI
         nspHI                   tfiI
         aflIII       hinfI       hphI              foKI
                                                    mnlI   bsrI
1701 ACCAACATGT GTCCTTCCTG ATTCTGTGGT GAAGCCACTG CCTCCATCCA GTGTGAAAGC AGAAATTACT ATAAACATTG GATTATTGAA AATATCTTGG
     TGGTTGTACA CAGGAAGGAC TAAGACACCA CTTCGGTGAC GGAGTAGGT CACACTTTCG TCTTTAATGA TATTTGTAAC CTAATAACTT TTATAGAACC
 526  P  T  C   V  L  P  D   S  V  V   K  P  L   P  P  S  S   V  K  A   E  I  T   I  N  I  G   L  L  K   I  S  W
                                       tfiI
                                       hinfI                 tru9I        rsaI
            bsrI                       xcmI                  mseI         csp6I      mboII                  sfaNI
1801 GAAAAGCCAG TCTTTTCCAGA GAATAACCTT CAATTCCAGA TTCCGTATGG TTTAAGTGGA AAAGAAGTAC AATGGAAGAT GTATGAGGTT TATGATGCAA
     CTTTTCGGTC AGAAAGGTCT CTTATTGGAA GTTAAGGTCT AAGGCATACC AAATTCACCT TTTCTTCATG TTACCTTCTA CATACTCCAA ATACTACGTT
 559  E  K  P   V  F  P  E   N  N  L   Q  F  Q   I  R  Y  G   L  S  G   K  E  V  Q   W  K  M   Y  E  V   Y  D  A  K
                                                                       hinPI                       rmaI
            bsmAI bsrI                                                 hhaI/cfoI mnlI maeI         bsrI
1901 AATCAAAATC TGTCAGTCTC CCAGTTCCAG ACTTGTGTGC AGTCTATGCT GTTCAGGTGC GCTGTAAGAG CTAGATGGA CTGGGATATT GGAGTAATTG
     TTAGTTTTAG ACAGTCAGAG GGTCAAGGTC TGAACACACG TCAGATACGA CAAGTCCACG CGACATTCTC CGATCTACCT GACCCTATAA CCTCATTAAC
 593  S  K  S   V  S  L   P  V  P  D   L  C  A   V  Y  A   V  Q  V  R   C  K  R   L  D  G   L  G  Y  W   S  N  W
                 sau96I
                 avaII
                 asuI
                 ppuMI                                                         tru9I
          nlaIII ecoNI ecoO109I/draII         apoI                             mseI
                 bsII  mnlI                                                    aseI/asnI/vspI
2001 GAGCAATCCA GCCTACACAG TTGTCATGGA TATAAAAGTT CCTATGAGAG GACCTGAATT TTGGAGAATA ATTAATGGAG ATACTATGAA AAAGGAGAAA
     CTCGTTAGGT CGGATGTGTC AACAGTACCT ATATTTTCAA GGATACTCTC CTGGACTTAA AACCTCTTAT TAATTACCTC TATGATACTT TTTCCTCTTT
 626  S  N  P   A  Y  T  V   V  M  D   I  K  V   P  M  R  G   P  E  F   W  R  I   I  N  G  D   T  M  K   K  E  K
```

```
                   maeIII
                                           pleI
                                           hinfI                                                       nlaIII
2101 AATGTCACTT TACTTTGGAA GCCCCTGATG AAAAATGACT CATTGTGCAG TGTTCAGAGA TATGTGATAA ACCATCATAC TTCCTGCAAT GGAACATGGT
     TTACAGTGAA ATGAAACCTT CGGGGACTAC TTTTTACTGA GTAACACGTC ACAAGTCTCT ATACACTATT TGGTAGTATG AAGGACGTTA CCTTGTACCA
659   N  V  T  L     L  W  K    P  L  M     K  N  D  S     L  C  S  V     Q  R  Y  V     V  I  N  H     H  T  S  C    N  G  T  W  S haeIII/palI
                                                                             mscI/balI
                                                                                haeI
             mboII                                                                eaeI
                       apoI                                 maeIII                 cfrI                   munI
2201 CAGAAGATGT GGGAAATCAC ACGAAATTCA CTTTCCTGTG GACAGAGCAA GCACATACTG TTACGGTTCT GGCCATCAAT TCAATTGGTG CTTCTGTTGC
     GTCTTCTACA CCCTTTAGTG TGCTTTAAGT GAAAGGACAC CTGTCTCGTT CGTGTATGAC AATGCCAAGA CCGGTAGTTA AGTTAACCAC GAAGACAACG
693   E  D  V    G  N  H     T  K  F  T     F  L  W       T  E  Q  A     H  T  V  L     T  R  T     Q  L  V     L  L  L
                                                                                                                          scrFI
                                                                                                                          mvaI
                                                                                                                          ecoRII
                                                        ddeI          truI                                                dsaV
                                                        draIII        mseI                                                bstNI
              bslI      haeIII/palI                     maeIII        ahaIII/draI                                         apyI[dcm+]
     tru9I tru9I        haeI
     apoI mseI          nlaIII
2301 AAATTTAAT TTAACCTTTT CATGGCCTAT GAGCAAAGTA AATATCGTGC AGTCACTCAG TGCTTATCCT TTAAACAGCA GTTGTGTGAT TGTTCCTGG
     TTTAAAATTA AATTGGAAAA GTACCGGATA CTCGTTTCAT TTATAGCACG TCAGTGAGTC ACGAATAGGA AATTTGTCGT CAACACACTA ACAAGGACC
726   N  F  N    L  T  F  S     W  P  M     S  K  V     N  I  V  Q     S  L  S       A  Y  P  L     N  S  S     C  V  I  V  S  W xmnI
                                                                                                         tfiI
                                                          truI                                           hinfI mboII
          draIII                                           mseI          mboII hphI                            asp700
           hphI bsrI         aluI                                                            ddeI       earI/ksp632I
2401 ATACTATCAC CCAGTGATTA CAAGCTAATG TATTTTATTA TTGAGTGGAA AAATCTTAAT GAAGATGGTG AAATAAAATG GCTTAGAATC TCTTCATCTG
     TATGATAGTG GGTCACTAAT GTTCGATTAC ATAAAATAAT AACTCACCTT TTTAGAATTA CTTCTACCAC TTTATTTTAC CGAATCTTAG AGAAGTAGAC
759   I  L  S  P     S  D  Y     K  L  M     Y  F  I  I     E  W  K    N  L  N     E  D  G  E     I  K  W    L  R  I  S  S  S  V
```

```
                                                        mnlI
                                                        hphI
                                                        maeIII
                                                        bstEII
              mnlI            mboII
              apoI            eco57I
3301  GAACTTTGA AATTGGAGGG AAATTTCCCT GAAGAAAATA ATGATAAAAA GTCTATCTAT TATTTAGGGG TCACCTCAAT CAAAAAGAGA GAGAGTGGTG
      CTTGAAAACT TTAACCTCCC TTTAAAGGGA CTTCTTTTAT TACTATTTT CAGATAGATA ATAAATCCCC AGTGGAGTTA GTTTTTCTCT CTCTCACCAC
1059  E  L  L  K  L  E  G  N  F  P  E  E  N  N  D  K  K  S  I  Y  Y  L  G  V  T  S  I  K  K  R  E  S  G  V scrFI
                                                                        mvaI
                                                                        ecoRII
                                                                        dsaV
                                                                        bstNI
              drdI              bsp1286                                 apyI[dcm+]
                                bmyI                                    gsuI/bpmI
3401  TGCTTTTGAC TGACAAGTCA AGGGTATCGT GCCCATTCCC AGCCCCCTGT TTATTCACGG ACATCAGAGT TCTCCAGGAC AGTTGCTCAC ACTTTGTAGA
      ACGAAAACTG ACTGTTCAGT TCCCATAGCA CGGGTAAGGG TCGGGGACA AATAAGTGCC TGTAGTCTCA AGAGGTCCTG TCAACGAGTG TGAAACATCT
1093  L  L  T  D  K  S  R  V  S  C  P  F  P  A  P  C  L  F  T  D  I  R  V  L  Q  D  S  C  S  H  F  V  E nlaIII
                                                                                            sau3AI
                                      mboII                      nlaIII                     mboI/ndeII[dam-]
                                      bpuAI                      nspI                       dpnI[dam+]
              rmaI                    bbsI   sfaNI nspHI mnlI              pleI             dpnI[dam-]
              maeI     ddeI                                                hinfI      ddeI
3501  AAATAATATC AACTTAGGAA CTTCTAGTAA GAAGACTTTT CCAAACTTGT GCATCTTACA TGCCTCAATT CCAAACTTGT TCTACTCAGA CTCATAAGAT CATGGAAAAC
      TTTATTATAG TTGAATCCTT GAAGATCATT CTTCTGAAAA GGTTTGAACA CGTAGAATGT ACGGAGTTAA GGTTTGAACA AGATGAGTCT GAGTATTCTA GTACCTTTTG
1126  N  N  I  N  L  G  T  S  S  K  K  T  F  A  S  Y  M  P  Q  F  Q  T  C  S  T  Q  T  H  K  I  M  E  N maeIII           mboII
                               eco57I
3601  AAGATGTGTG ACCTAACTGT GTAATTTCAC TGAAGAAACC TTCAGATTTG TGTTATAATG GGTAATATAA AGTGTAATAG ATTATAGTTG TGGGTGGGAG
      TTCTACACAC TGGATTGACA CATTAAAGTG ACTTCTTTGG AAGTCTAAAC ACAATATTAC CCATTATATT TCACATTATC TAATATCAAC ACCCACCCTC
1159  K  M  C  D  L  T  V  V  I  S  L  K  K  P  S  D  L  C  Y  N  G  Y  I  * pleI                                                      xmnI
              hinfI apoI                                  ddeI maeIII   asp700
3701  AGAGAAAAGA AACCAGAGTC AAATTTGAAA ATAATTGTTC CAAATGAATG TTGTCTGTTT GTTCTCTCTT AGTAACATAG ACAAAAAATT TGAGAAAGCC
      TCTCTTTTCT TTGGTCTCAG TTTAAACTTT TATTAACAAG GTTTACTTAC AACAGACAA CAAGAGAGAA TCATTGTATC TGTTTTTAA ACTCTTTCGG
```

FIG. 1I

```
                                                                          sau96I
                                                                          nlaIV
                                                                          avaII
                                                   rmaI          asuI               rmaI
                                                   maeI          ppuMI              maeI
                          mboII                    aluI          ecoO109I/draII     aluI
            accI          earI/ksp632I
            sapI
3801 TTCATAAGCC TACCAATGTA GACACGCTCT TCTATTTTAT TCCCAAGCTC TAGTGGGAAG GTCCCTTGTT TCCAGCTAGA AATAAGCCCA ACAGACACCA
     AAGTATTCGG ATGGTTACAT CTGTGCGAGA AGATAAAATA AGGGTTCGAG ATCACCCTTC CAGGGAACAA AGTCGATCT  TTATTCGGGT TGTCTGTGGT nspI
                                                                                                        nspHI
                                                                      rsaI                              tru9I nlaIII
                                   mnlI                               csp6I                             mseI aflIII
3901 TCTTTTGTGA GATGTAATTG TTTTTTCAGA GGGCGTGTTG TTTTACCTCA AGTTTTTGTT TTGTACCAAC ACACACACAC ACACACATTG TTAACACATG
     AGAAAACACT CTACATTAAC AAAAAAGTCT CCCGCACAAC AAAATGGAGT TCAAAAACAA AACATGGTTG TGTGTGTGTG TGTGTGTAAC AATTGTGTAC sfuI
                                                                                                        bstBI
                                                                                                        bsiCI
                                                                                                        asuII
                                                                                           tru9I        ecoRI
                                                 scfI                                      mseI         apoI
4001 TCCTTGTGTG TTTTGAGAGT ATATTATGTA TTTATATTTT GTGCTATACAG ACTGTAGGAT TTGAAGTAGG ACTTCCTAA ATGTTTAAGA TAAACAGAAT
     AGGAACACAC AAAACTCTCA TATAATACAT AAATATAAAA CACGATATGTC TGACATCCTA AACTTCATCC TGAAAGGATT TACAAATTCT ATTTGTCTTA taqI
4101 TC
     AG length: 4102
```

FIG. 1J

```
wsxfull.6.4.variant    1   MICQKFCVVLLHWEFIYVITAFNLSYP ITPWRFKLSCMPPNSTYDYFLLP
wsxfull.12.1.variant   1   MICQKFCVVLLHWEFIYVITAFNLSYP ITPWRFKLSCMPPNSTYDYFLLP
wsxfull.13.2.variant   1   MICQKFCVVLLHWEFIYVITAFNLSYP ITPWRFKLSCMPPNSTYDYFLLP wsxfull.6.4.variant   51   AGLSKNTSNSNGHYETAVEPKFNSSGTHFSNLSKTTFHCCFRSEQDRNCS
wsxfull.12.1.variant  51   AGLSKNTSNSNGHYETAVEPKFNSSGTHFSNLSKTTFHCCFRSEQDRNCS
wsxfull.13.2.variant  51   AGLSKNTSNSNGHYETAVEPKFNSSGTHFSNLSKTTFHCCFRSEQDRNCS wsxfull.6.4.variant  101   LCADNIEGKTFVSTVNSLVFQQIDANWNIQCWLKGDLKLFICYVVESLFKN
wsxfull.12.1.variant 101   LCADNIEGKTFVSTVNSLVFQQIDANWNIQCWLKGDLKLFICYVVESLFKN
wsxfull.13.2.variant 101   LCADNIEGKTFVSTVNSLVFQQIDANWNIQCWLKGDLKLFICYVVESLFKN wsxfull.6.4.variant  151   LFRNYNYKVHLLYVLPEVLEDSPLVPQKGSFQMVHCNCSVHECCECLVPV
wsxfull.12.1.variant 151   LFRNYNYKVHLLYVLPEVLEDSPLVPQKGSFQMVHCNCSVHECCECLVPV
wsxfull.13.2.variant 151   LFRNYNYKVHLLYVLPEVLEDSPLVPQKGSFQMVHCNCSVHECCECLVPV wsxfull.6.4.variant  201   PTAKLNDTLLMCLKITSGGVIFQSPLMSVQPINMVKPDPPLGLHMEITDD
wsxfull.12.1.variant 201   PTAKLNDTLLMCLKITSGGVIFQSPLMSVQPINMVKPDPPLGLHMEITDD
wsxfull.13.2.variant 201   PTAKLNDTLLMCLKITSGGVIFQSPLMSVQPINMVKPDPPLGLHMEITDD wsxfull.6.4.variant  251   GNLKISWSSPPLVPFFPLQYQVKYSENSTTVIREADKIVSATSLLVDSILP
wsxfull.12.1.variant 251   GNLKISWSSPPLVPFFPLQYQVKYSENSTTVIREADKIVSATSLLVDSILP
wsxfull.13.2.variant 251   GNLKISWSSPPLVPFFPLQYQVKYSENSTTVIREADKIVSATSLLVDSILP
```

FIG. 2A

```
wsxfull.6.4.variant   301  GSSYEVQVRGKRLDGPGIWSDWSTPRVFTTQDVIYFPPKILTSVGSNVSF
wsxfull.12.1.variant  301  GSSYEVQVRGKRLDGPGIWSDWSTPRVFTTQDVIYFPPKILTSVGSNVSF
wsxfull.13.2.variant  301  GSSYEVQVRGKRLDGPGIWSDWSTPRVFTTQDVIYFPPKILTSVGSNVSF wsxfull.6.4.variant   351  HCIYKKENKIVPSKEIVWWMNLAEKIPQSQYDVVSDHVSKVTFFNLNETK
wsxfull.12.1.variant  351  HCIYKKENKIVPSKEIVWWMNLAEKIPQSQYDVVSDHVSKVTFFNLNETK
wsxfull.13.2.variant  351  HCIYKKENKIVPSKEIVWWMNLAEKIPQSQYDVVSDHVSKVTFFNLNETK wsxfull.6.4.variant   401  PRGKFTYDAVYCCNEHECHHRYAELYVIDVNINISCETDGYLTKMTCRWS
wsxfull.12.1.variant  401  PRGKFTYDAVYCCNEHECHHRYAELYVIDVNINISCETDGYLTKMTCRWS
wsxfull.13.2.variant  401  PRGKFTYDAVYCCNEHECHHRYAELYVIDVNINISCETDGYLTKMTCRWS wsxfull.6.4.variant   451  TSTIQSLAESTLQLRYHRSSLYCSDIPSIHPISEPKDCYLQSDGFYECIF
wsxfull.12.1.variant  451  TSTIQSLAESTLQLRYHRSSLYCSDIPSIHPISEPKDCYLQSDGFYECIF
wsxfull.13.2.variant  451  TSTIQSLAESTLQLRYHRSSLYCSDIPSIHPISEPKDCYLQSDGFYECIF wsxfull.6.4.variant   501  QPIFLLSGYTMWIRINHSLGSLDSPPTCVLPDSVVKPLPPSSVKAEITIN
wsxfull.12.1.variant  501  QPIFLLSGYTMWIRINHSLGSLDSPPTCVLPDSVVKPLPPSSVKAEITIN
wsxfull.13.2.variant  501  QPIFLLSGYTMWIRINHSLGSLDSPPTCVLPDSVVKPLPPSSVKAEITIN wsxfull.6.4.variant   551  IGLLKISWEKPVFPENNLQFQIRYGLSGKEVQWKMYEVYDAKSKSVSLPV
wsxfull.12.1.variant  551  IGLLKISWEKPVFPENNLQFQIRYGLSGKEVQWKMYEVYDAKSKSVSLPV
wsxfull.13.2.variant  551  IGLLKISWEKPVFPENNLQFQIRYGLSGKEVQWKMYEVYDAKSKSVSLPV
```

FIG. 2B

```
wsxfull.6.4.variant   601  PDLCAVYYAVQVRCKRLDGLGYWSNWSNPAYTVVMDIKVPMRGPEFWRIIN
wsxfull.12.1.variant  601  PDLCAVYYAVQVRCKRLDGLGYWSNWSNPAYTVVMDIKVPMRGPEFWRIIN
wsxfull.13.2.variant  601  PDLCAVYYAVQVRCKRLDGLGYWSNWSNPAYTVVMDIKVPMRGPEFWRIIN wsxfull.6.4.variant   651  GDTMKKEKNVTLLWKPLMKNDSLCSVQRYVINHHTSCNGTWSEDVGNHTK
wsxfull.12.1.variant  651  GDTMKKEKNVTLLWKPLMKNDSLCSVQRYVINHHTSCNGTWSEDVGNHTK
wsxfull.13.2.variant  651  GDTMKKEKNVTLLWKPLMKNDSLCSVQRYVINHHTSCNGTWSEDVGNHTK wsxfull.6.4.variant   701  FTFLWTEQAHTVTVLAINSIGASVANFNLTFSWPMSKVNIVQSLSAYPLN
wsxfull.12.1.variant  701  FTFLWTEQAHTVTVLAINSIGASVANFNLTFSWPMSKVNIVQSLSAYPLN
wsxfull.13.2.variant  701  FTFLWTEQAHTVTVLAINSIGASVANFNLTFSWPMSKVNIVQSLSAYPLN wsxfull.6.4.variant   751  SSCVIVSWILSPSDYKLMYFIIEWKNLNEDGEIKWLRISSSVKKYYIHDH
wsxfull.12.1.variant  751  SSCVIVSWILSPSDYKLMYFIIEWKNLNEDGEIKWLRISSSVKKYYIHDH
wsxfull.13.2.variant  751  SSCVIVSWILSPSDYKLMYFIIEWKNLNEDGEIKWLRISSSVKKYYIHDH Trans
wsxfull.6.4.variant   801  FIPIEKYQFSLYPIFMEGVGKPKIINSFTQDDIEKHQSDAGLYVIVPVI-
wsxfull.12.1.variant  801  FIPIEKYQFSLYPIFMEGVGKPKIINSFTQDDIEKHQSDAGLYVIVPVI-
wsxfull.13.2.variant  801  FIPIEKYQFSLYPIFMEGVGKPKIINSFTQDDIEKHQSDAGLYVIVPVI-
                                membrane Domain          Box 1 wsxfull.6.4.variant   851  SSSILLLGTLLISHQRMKKLFWEDVPNPKNCSWAQGLNFQK......MF.
wsxfull.12.1.variant  851  SSSILLLGTLLISHQRMKKLFWEDVPNPKNCSWAQGLNFQK......MF.
wsxfull.13.2.variant  851  SSSILLLGTLLISHQRMKKLFWEDVPNPKNCSWAQGLNFQKPETFEHLFI-
```

FIG. 2C

```
                                                     Box 2
wsxfull.13.2.variant   901  KHTASVTC GPLLLEPETISEDISVDTSWKNKDEMMPTTVVSLLSTTDLEK
                                                Box 3
wsxfull.13.2.variant   951  GSVCIS DQF N SVNFSEAEGTEVTYEDESQR Q PFVKYATLISNSKPSETGE wsxfull.6.4.variant    892  . . . . . . . . . . . . . . . . . . . . . . . . . . . . . . . . . . . . . . . . . . . . . . . . . . . . .
wsxfull.12.1.variant   894  . . . . . . . . . . . . . . . . . . . . . . . . . . . . . . . . . . . . . . . . . RT PR I VPGH
wsxfull.13.2.variant  1001  EQGLINSSVTKCFSSKNSPLKDSFSNSSWEIEAQAFFILSDQH PN I SPH wsxfull.6.4.variant    893  . . . . . . . . . . . . . . . . . . . . . . . . . . . . . . . . . . . . T D I L . . .
wsxfull.12.1.variant   903  . . . . . . . . . . . . . . . . . . . . . . . . . . . . . . . . . . . . K D L IF . . .
wsxfull.13.2.variant  1051  LTFSEGLDELLKLEGNFPEENNDKKSIYYLGVTSIKKRESGV L TDKSRV wsxfull.12.1.variant   908  . . . . . . . . . . . . . . . . R R C L KAACSLR V ITTP . . . . . . . . . . . . . . . . . . . .
wsxfull.13.2.variant  1101  SCPFPAPCLFTDI R V L QDSC SHF V ENNINLGTSSKKTFASYMPQFQTCST wsxfull.13.2.variant  1151  QTHKIMENKMCDLTV
```

| | | |
|---|---|---|
| wsxfull.6.4.variant | 351 | CTTCCTTTTGCCTGCTGGACTCTCAAAGAATACTTCAAATTCGAATGGAC |
| wsxfull.12.1.variant | 264 | CTTCCTTTTGCCTGCTGGACTCTCAAAGAATACTTCAAATTCGAATGGAC |
| wsxfull.13.2.variant | 264 | CTTCCTTTTGCCTGCTGGACTCTCAAAGAATACTTCAAATTCGAATGGAC |
| wsxfull.6.4.variant | 401 | ATTATGAGACAGCTGTTGAACCTAAGTTTAATTCAAGTGGTACTCACTTT |
| wsxfull.12.1.variant | 314 | ATTATGAGACAGCTGTTGAACCTAAGTTTAATTCAAGTGGTACTCACTTT |
| wsxfull.13.2.variant | 314 | ATTATGAGACAGCTGTTGAACCTAAGTTTAATTCAAGTGGTACTCACTTT |
| wsxfull.6.4.variant | 451 | TCTAAACTTATCCAAAACAAACAACTTTCCACTGTTGCTTTCGGAGTGAGCAAGA |
| wsxfull.12.1.variant | 364 | TCTAAACTTATCCAAAACAAACAACTTTCCACTGTTGCTTTCGGAGTGAGCAAGA |
| wsxfull.13.2.variant | 364 | TCTAAACTTATCCAAAACAAACAACTTTCCACTGTTGCTTTCGGAGTGAGCAAGA |
| wsxfull.6.4.variant | 501 | TAGAAACTGCTCCTCCTTATGTGCAGAGACAACAACATTGAAGGAAAGACATTTGTTT |
| wsxfull.12.1.variant | 414 | TAGAAACTGCTCCTCCTTATGTGCAGAGACAACAACATTGAAGGAAAGACATTTGTTT |
| wsxfull.13.2.variant | 414 | TAGAAACTGCTCCTCCTTATGTGCAGAGACAACAACATTGAAGGAAAGACATTTGTTT |
| wsxfull.6.4.variant | 551 | CNACAGTAAAATTCTTTAGTTTTTCAACAAAAATAGATGCAAACTGGAACATA |
| wsxfull.12.1.variant | 464 | CAACAGTAAAATTCTTTAGTTTTTCAACAAAAATAGATGCAAACTGGAACATA |
| wsxfull.13.2.variant | 464 | CAACAGTAAAATTCTTTAGTTTTTCAACAAAAATAGATGCAAACTGGAACATA |
| wsxfull.6.4.variant | 601 | CAGTGCTGGCTAAAAGGAGACTTAAAATTATTCATCTGTTATGTGGAGTC |
| wsxfull.12.1.variant | 514 | CAGTGCTGGCTAAAAGGAGACTTAAAATTATTCATCTGTTATGTGGAGTC |
| wsxfull.13.2.variant | 514 | CAGTGCTGGCTAAAAGGAGACTTAAAATTATTCATCTGTTATGTGGAGTC |

| | | |
|---|---|---|
| wsxfull.6.4.variant | 651 | ATTATTTAAGAATCTATTCAGGAATTATAACTATAAGGTCCATCTTTTAT |
| wsxfull.12.1.variant | 564 | ATTATTTAAGAATCTATTCAGGAATTATAACTATAAGGTCCATCTTTTAT |
| wsxfull.13.2.variant | 564 | ATTATTTAAGAATCTATTCAGGAATTATAACTATAAGGTCCATCTTTTAT |
| | | |
| wsxfull.6.4.variant | 701 | ATGTTCTGCCTGAAGTGTTAGAAGATTCACCCTCTGGTTCCCCAAAAGGC |
| wsxfull.12.1.variant | 614 | ATGTTCTGCCTGAAGTGTTAGAAGATTCACCCTCTGGTTCCCCAAAAGGC |
| wsxfull.13.2.variant | 614 | ATGTTCTGCCTGAAGTGTTAGAAGATTCACCCTCTGGTTCCCCAAAAGGC |
| | | |
| wsxfull.6.4.variant | 751 | AGTTTTCAGATGGTTCACTGCAATTGCAGTGTTCATGAATGTTGTGAATG |
| wsxfull.12.1.variant | 664 | AGTTTTCAGATGGTTCACTGCAATTGCAGTGTTCATGAATGTTGTGAATG |
| wsxfull.13.2.variant | 664 | AGTTTTCAGATGGTTCACTGCAATTGCAGTGTTCATGAATGTTGTGAATG |
| | | |
| wsxfull.6.4.variant | 801 | TCTTGTGCCTGTGCCAACAGCCAAACTCAACGACACTCTCCTTATGTGTT |
| wsxfull.12.1.variant | 714 | TCTTGTGCCTGTGCCAACAGCCAAACTCAACGACACTCTCCTTATGTGTT |
| wsxfull.13.2.variant | 714 | TCTTGTGCCTGTGCCAACAGCCAAACTCAACGACACTCTCCTTATGTGTT |
| | | |
| wsxfull.6.4.variant | 851 | TGAAAATCACATCTGGTGGAGTAATTTTTCCAGTCACCTCTAATGTCAGTT |
| wsxfull.12.1.variant | 764 | TGAAAATCACATCTGGTGGAGTAATTTTTCCAGTCACCTCTAATGTCAGTT |
| wsxfull.13.2.variant | 764 | TGAAAATCACATCTGGTGGAGTAATTTTTCCAGTCACCTCTAATGTCAGTT |
| | | |
| wsxfull.6.4.variant | 901 | CAGCCCATAAATATGGTGAAGCCTGATCCACCATTAGGTTTGCATATGGA |
| wsxfull.12.1.variant | 814 | CAGCCCATAAATATGGTGAAGCCTGATCCACCATTAGGTTTGCATATGGA |
| wsxfull.13.2.variant | 814 | CAGCCCATAAATATGGTGAAGCCTGATCCACCATTAGGTTTGCATATGGA |

| | | |
|---|---|---|
| wsxfull.6.4.variant | 951 | AATCACAGATGATGGTAAATTTAAAGATTTCTTGGTCCAGCCCACCATTGG |
| wsxfull.12.1.variant | 864 | AATCACAGATGATGGTAAATTTAAAGATTTCTTGGTCCAGCCCACCATTGG |
| wsxfull.13.2.variant | 864 | AATCACAGATGATGGTAAATTTAAAGATTTCTTGGTCCAGCCCACCATTGG |
| wsxfull.6.4.variant | 1001 | TACCATTTCCACTTCAATATCAAGTGAAATATTCAGAGAATTCTACAACA |
| wsxfull.12.1.variant | 914 | TACCATTTCCACTTCAATATCAAGTGAAATATTCAGAGAATTCTACAACA |
| wsxfull.13.2.variant | 914 | TACCATTTCCACTTCAATATCAAGTGAAATATTCAGAGAATTCTACAACA |
| wsxfull.6.4.variant | 1051 | GTTATCAGAGAAGCTGACAAGATTGTCTCAGCTACATCCCTGCTAGTAGA |
| wsxfull.12.1.variant | 964 | GTTATCAGAGAAGCTGACAAGATTGTCTCAGCTACATCCCTGCTAGTAGA |
| wsxfull.13.2.variant | 964 | GTTATCAGAGAAGCTGACAAGATTGTCTCAGCTACATCCCTGCTAGTAGA |
| wsxfull.6.4.variant | 1101 | CAGTATACTTCCTGGGTCTTCGTATGAGGTTCAGGTGAGGGCAAGAGAC |
| wsxfull.12.1.variant | 1014 | CAGTATACTTCCTGGGTCTTCGTATGAGGTTCAGGTGAGGGCAAGAGAC |
| wsxfull.13.2.variant | 1014 | CAGTATACTTCCTGGGTCTTCGTATGAGGTTCAGGTGAGGGCAAGAGAC |
| wsxfull.6.4.variant | 1151 | TGGATGGCCCAGGAATCTGGAGTGACTCCTCCTCGTCGTCTTTACC |
| wsxfull.12.1.variant | 1064 | TGGATGGCCCAGGAATCTGGAGTGACTCCTCCTCGTCGTCTTTACC |
| wsxfull.13.2.variant | 1064 | TGGATGGCCCAGGAATCTGGAGTGACTCCTCCTCGTCGTCTTTACC |
| wsxfull.6.4.variant | 1201 | ACACAAGATGTCATATACTTTCCACCTAAAATTCTGACAAGTGTTGGGTC |
| wsxfull.12.1.variant | 1114 | ACACAAGATGTCATATACTTTCCACCTAAAATTCTGACAAGTGTTGGGTC |
| wsxfull.13.2.variant | 1114 | ACACAAGATGTCATATACTTTCCACCTAAAATTCTGACAAGTGTTGGGTC |

FIG. 3D

| | | |
|---|---|---|
| wsxfull.6.4.variant | 1251 | TAATGTTTCTTTTCACTGCATCTATAAGAAAACAAGATTGTTCCCT |
| wsxfull.12.1.variant | 1164 | TAATGTTTCTTTTCACTGCATCTATAAGAAAACAAGATTGTTCCCT |
| wsxfull.13.2.variant | 1164 | TAATGTTTCTTTTCACTGCATCTATAAGAAAACAAGATTGTTCCCT |
| wsxfull.6.4.variant | 1301 | CAAAAGAGATTGTTTGGTGGATGAATTTAGCTGAGAAAATTCCTCAAAGC |
| wsxfull.12.1.variant | 1214 | CAAAAGAGATTGTTTGGTGGATGAATTTAGCTGAGAAAATTCCTCAAAGC |
| wsxfull.13.2.variant | 1214 | CAAAAGAGATTGTTTGGTGGATGAATTTAGCTGAGAAAATTCCTCAAAGC |
| wsxfull.6.4.variant | 1351 | CAGTATGATGTTGTTGTGAGTGATCATCATGTTAGCAAAAGTTACTTTTTTCAATCT |
| wsxfull.12.1.variant | 1264 | CAGTATGATGTTGTTGTGAGTGATCATCATGTTAGCAAAAGTTACTTTTTTCAATCT |
| wsxfull.13.2.variant | 1264 | CAGTATGATGTTGTTGTGAGTGATCATCATGTTAGCAAAAGTTACTTTTTTCAATCT |
| wsxfull.6.4.variant | 1401 | GAATGAAACCAAACATGAATCATCGGAGGAAAAGTTTACCTATGCTGAATTATATGTGATTGCT |
| wsxfull.12.1.variant | 1314 | GAATGAAACCAAACATGAATCATCGGAGGAAAAGTTTACCTATGCTGAATTATATGTGATTGCT |
| wsxfull.13.2.variant | 1314 | GAATGAAACCAAACATGAATCATCGGAGGAAAAGTTTACCTATGCTGAATTATATGTGATTGCT |
| wsxfull.6.4.variant | 1451 | GCAATGAAACATGAATCTCATGTGAAACTGATGGGGTACTTAAACTAAAATGAT |
| wsxfull.12.1.variant | 1364 | GCAATGAAACATGAATCTCATGTGAAACTGATGGGGTACTTAAACTAAAATGAT |
| wsxfull.13.2.variant | 1364 | GCAATGAAACATGAATCTCATGTGAAACTGATGGGGTACTTAAACTAAAATGAT |
| wsxfull.6.4.variant | 1501 | GTCAATATCAATATCTCATGTGAAACTGATGGGGTACTTAAACTAAAATGAC |
| wsxfull.12.1.variant | 1414 | GTCAATATCAATATCTCATGTGAAACTGATGGGGTACTTAAACTAAAATGAC |
| wsxfull.13.2.variant | 1414 | GTCAATATCAATATCTCATGTGAAACTGATGGGGTACTTAAACTAAAATGAC |

```
wsxfull.6.4.variant   1851  AATTACTATAAACATTGGATTATTGAAAAATATCTTGGGAAAAAGCCAGTCT
wsxfull.12.1.variant  1764  AATTACTATAAACATTGGATTATTGAAAAATATCTTGGGAAAAAGCCAGTCT
wsxfull.13.2.variant  1764  AATTACTATAAACATTGGATTATTGAAAAATATCTTGGGAAAAAGCCAGTCT wsxfull.6.4.variant   1901  TTCCAGAGAATAACCTTCAATTCCAGATTCGCTATGGTTTAAGTGGAAAA
wsxfull.12.1.variant  1814  TTCCAGAGAATAACCTTCAATTCCAGATTCGCTATGGTTTAAGTGGAAAA
wsxfull.13.2.variant  1814  TTCCAGAGAATAACCTTCAATTCCAGATTCGCTATGGTTTAAGTGGAAAA wsxfull.6.4.variant   1951  GAAGTACAATGGAAGATGTATGAGGTTTATGATGCAAAAATCAAAATCTGT
wsxfull.12.1.variant  1864  GAAGTACAATGGAAGATGTATGAGGTTTATGATGCAAAAATCAAAATCTGT
wsxfull.13.2.variant  1864  GAAGTACAATGGAAGATGTATGAGGTTTATGATGCAAAAATCAAAATCTGT wsxfull.6.4.variant   2001  CAGTCTCCCAGTTCCAGACTTGTGTGTGCAGTCTATGCTGTTCAGGTGCGCT
wsxfull.12.1.variant  1914  CAGTCTCCCAGTTCCAGACTTGTGTGTGCAGTCTATGCTGTTCAGGTGCGCT
wsxfull.13.2.variant  1914  CAGTCTCCCAGTTCCAGACTTGTGTGTGCAGTCTATGCTGTTCAGGTGCGCT wsxfull.6.4.variant   2051  GTAAGAGGCTAGATGGACTGGGATATTGGAGTAATTGGAGCAATCCAGCC
wsxfull.12.1.variant  1964  GTAAGAGGCTAGATGGACTGGGATATTGGAGTAATTGGAGCAATCCAGCC
wsxfull.13.2.variant  1964  GTAAGAGGCTAGATGGACTGGGATATTGGAGTAATTGGAGCAATCCAGCC wsxfull.6.4.variant   2101  TACACAGTTGTCATGGATATAAAAGTTCCTATGAGAGGACCTGAATTTTG
wsxfull.12.1.variant  2014  TACACAGTTGTCATGGATATAAAAGTTCCTATGAGAGGACCTGAATTTTG
wsxfull.13.2.variant  2014  TACACAGTTGTCATGGATATAAAAGTTCCTATGAGAGGACCTGAATTTTG
```

```
wsxfull.13.2.variant  3514  TTAGGAACTTCTAGTAAGAAGACTTTTGCATCTTACATGCCTCAATTCCA wsxfull.13.2.variant  3564  AACTTGTTCTACTCAGACTCATAAGATCATGGAAAACAAGATGTGTGACC wsxfull.13.2.variant  3614  TAACTGTGTAATTTCACTGAAGAAACCTTCAGATTTGTGTTATAATGGGT wsxfull.13.2.variant  3664  AATATAAAGTGTAATAGATTATAGTTGTGGGTGGGAGAGAGAAAAGAAAC wsxfull.13.2.variant  3714  CAGAGTCAAATTTGAAAATAATTGTTCCAAATGAATGTTGTCTGTTTGTT wsxfull.13.2.variant  3764  CTCTCTTAGTAACATAGACAAAATTTGAGAAAGCCTTCATAAGCCTAC wsxfull.13.2.variant  3814  CAATGTAGACACGCTCTTCTTCTATTTTCCAAGCTCTAGTGGGAAGGTC wsxfull.13.2.variant  3864  CCTTGTTTCCAGCTAGAAATAAGCCCAACAGACACCATCTTTTGTGAGAT wsxfull.13.2.variant  3914  GTAATTGTTTTTTCAGAGGGCGTGTTGTTTTACCTCAAGTTTTTGTTTTG wsxfull.13.2.variant  3964  TACCAACACACACACACATTCTTAACACATGTCCTTGTGTGTGTTT wsxfull.13.2.variant  4014  TGAGAGTATATTATGTATTTATTTTGTGCTATCAGACTGTAGGATTTG wsxfull.13.2.variant  4064  AAGTAGGACTTTCCTAAATGTTTAAGATAAACAGAATTC
```

FIG. 3L

```
wsxfull.13.2.variant    1  M I C Q K F C V V L L H W E F I Y V I T A F N L S Y P I T P W R F K L S C M P P N S T Y D F L L P
mu.wsx.ecd              1  M M C Q K F Y V V L L H W E F L Y V I A A N L A Y P I S P W K F K L F C G P P N T D D S F L S P wsxfull.13.2.variant   51  A G L S K N T S N S N G H Y E T A V E P K F N S S G T H F S N L S K T T F H C C F R S E Q D R N C S
mu.wsx.ecd             51  A G A P N N A S A L K G A S E A I V E A K F N S S G I Y V P E L S K T V F H C C F G N E Q G Q N C S wsxfull.13.2.variant  101  L C A D N I E G K T F V S T V N S L V F Q Q I D A N W N I Q C W L K G D L K L F I C Y V E S L F K N
mu.wsx.ecd            101  A L T D N T E G K T L A S V V K A S V F R Q L G V N W D I E C W M K G D L T L F I C H W E P L P K N wsxfull.13.2.variant  151  L F R N Y N Y K V H L L Y V L P E V L E D S P L V P O K G S F Q M V H C N C S V H E C C E C L V P V
mu.wsx.ecd            151  P F K N Y D S K V H L L Y D L P E V I D D S P L P P L K D S F Q T V Q C N C S L R G - C E C H V P V wsxfull.13.2.variant  201  P T A K L N D T L L M C L K I T S G G V I F Q S P L M S V Q P I N M V K P D P P L G H M E I T D D
mu.wsx.ecd            200  P R A K L N Y A L L M Y L E I T S A G V S F Q S P L M S L Q P M L V K P D P P L G L H M E V T D D wsxfull.13.2.variant  251  G N L K I S W S S P P L V P F P L Q Y Q V K Y S E N S T T V I R E A D K I V S A T S L L V D S I L P
mu.wsx.ecd            250  G N L K I S W D S Q T M A P F P L Q Y Q V K Y L E N S - T I V R E A A E I V S A T S L L V D S V L P
```

FIG. 4A

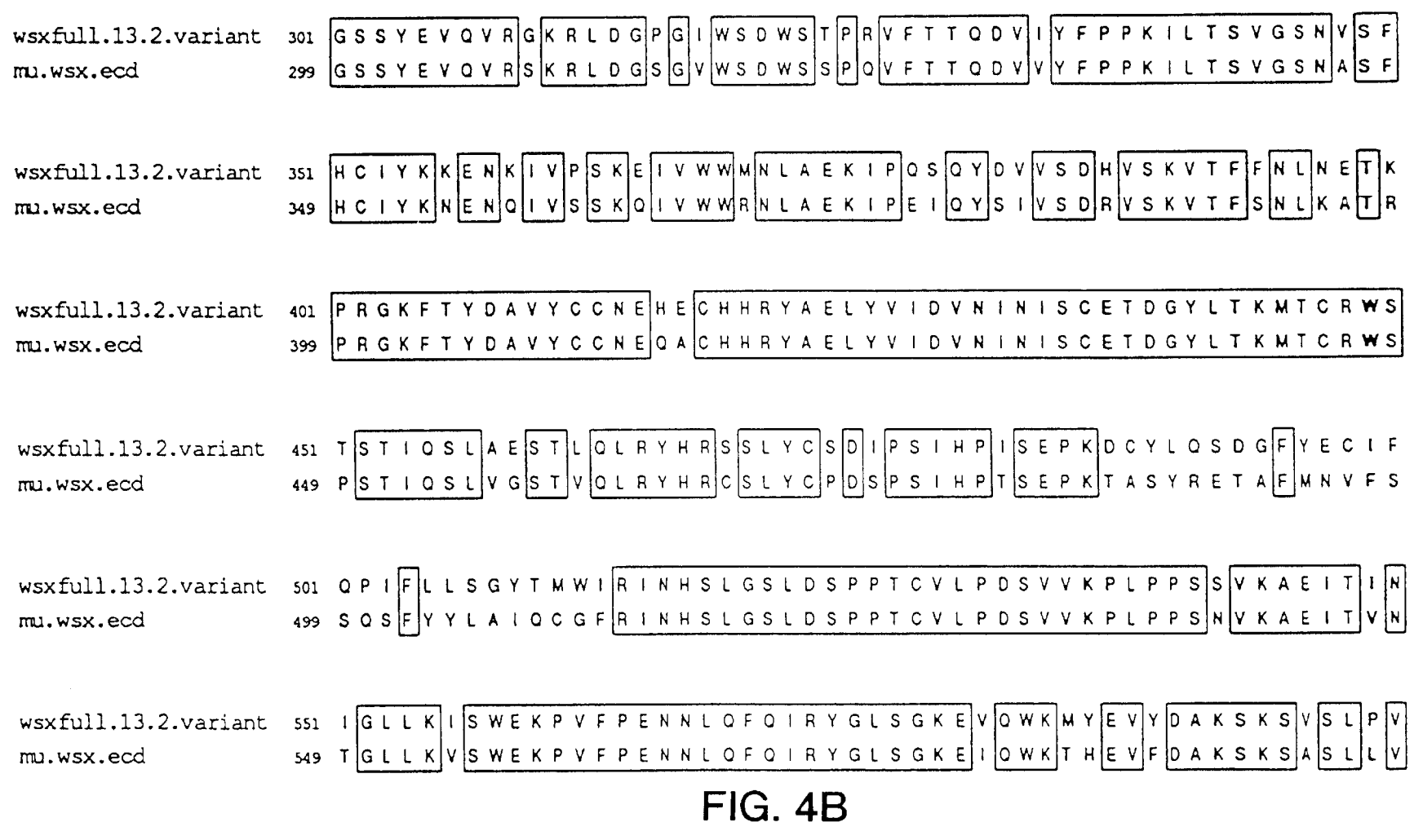

| | | |
|---|---|---|
| wsxfull.13.2.variant | 301 | G S S Y E V Q V R G K R L D G P G I W S D W S T P R V F T T Q D V I Y F P P K I L T S V G S N V S F |
| mu.wsx.ecd | 299 | G S S Y E V Q V R S K R L D G S G V W S D W S S P Q V F T T Q D V Y F P P K I L T S V G S N A S F |
| | | |
| wsxfull.13.2.variant | 351 | H C I Y K K E N K I V P S K E I V W W M N L A E K I P Q S Q Y D V S D H V S K V T F F N L N E T K |
| mu.wsx.ecd | 349 | H C I Y K N E N Q I V S S K Q I V W W R N L A E K I P E I Q Y S I V S D R V S K V T F S N L K A T R |
| | |

| | | |
|---|---|---|
| wsxfull.13.2.variant | 601 | P D L C A V Y Y A V Q V R C R L D G L G Y W S N W S N P A Y T V V M D I K V P M R G P E F W R I I N |
| mu.wsx.ecd | 599 | S D L C A V Y Y V V Q V R C R R L D G L G Y W S N W S S P A Y T L V M D V K V P M R G P E F W R K M D |
| wsxfull.13.2.variant | 651 | G D T M K K E K N V T L L W K P L M K N D S L C S V Q R Y V I N H H T S C N G T W S E D V G N H T K |
| mu.wsx.ecd | 649 | G D V T K K E R N V T L L W K P L T K N D S L C S V R R Y V K H R T A H N G T W S E D V G N R T N |
| wsxfull.13.2.variant | 701 | F T F L W T E Q A H T V T V L A I N S I G A S V A N F N L T F S W P M S K V N I V Q S L S A Y P L N |
| mu.wsx.ecd | 699 | L T F L W T E P A H T V T V L A V N S L G A S L V N F N L T F S W P M S K V S A V E S L S A Y P L S |
| wsxfull.13.2.variant | 751 | S S C V I V S W I L S P S Q Y K L M Y F I E W K N L N E D G E I K W L R I S S S V K K Y Y I H D H |
| mu.wsx.ecd | 749 | S S C V I L S W T L S P D D Y S L Y L V I E W K I L N E D D G M K W L R I P S N V K K Y Y I H D H |
| wsxfull.13.2.variant | 801 | F I P I E K Y Q F S L Y P I F M E G V G K P K I I N S F T Q D D I E K H Q S D A G L Y V I V P V I I |
| wsxfull.13.2.variant | 851 | S S S I L L L G T L L L I S H Q R M K K L F W E D V P N P K N C S W A Q G L N F Q K P E T F E H L F I |

FIG. 4C

```
wsxfull.13.2.variant  901  KHTASVTCGPLLLEPETISEDISVDTSWKNKDEMMPTTVVSLLSTTDLEK wsxfull.13.2.variant  951  GSVCISDQFNSVNFSEAEGTEVTYEDESQRQPFVKYATLISNSKPSETGE wsxfull.13.2.variant 1001  EQGLINSSVTKCFSSKNSPLKDSFSNSSWEIEAQAFFILSDQHPNIISPH wsxfull.13.2.variant 1051  LTFSEGLDELLKLEGNFPEENNDKKSIYYLGVTSIKKRESGVLLTDKSRV wsxfull.13.2.variant 1101  SCPFPAPCLFTDIRVLQDSCSHFVENNINLGTSSKKTFASYMPQFQTCST wsxfull.13.2.variant 1151  QTHKIMENKMCDLTV
```

FIG. 4D

```
mu.wsx.ecd         1  GGGCCCCCCCTCGAAGTCGACGGTATCGATAAGCTTGATATCGAATTCCG
mu.wsx.ecd        51  GCCGGGACACAGGTGGGACACTCTTTTAGTCCTCAATCCCTGGCGCGAGG
mu.wsx.ecd       101  CCACCCAAGGCAAACGCAGGACGCAGGGCGTTTGGGACCAGGCAGCAGAC
mu.wsx.ecd       151  TGGGGCGGTACCTGCGGAGAGCCACGCAACTTCTCCAGGCCTCTGACTAC
mu.wsx.ecd       201  TTTGGAAACTGCCCCGGGGCTGCGACATCAACCCCTTAAGTCCCGGAGGCG
mu.wsx.ecd       251  GAAAGAGGGTGGGTTTGAAAGACACAAGGAAGAAAAATGTGCTGTG
mu.wsx.ecd       301  GGGCGGGTTAAGTTTCCCACCCTCTTCCCCCCTTCCCGAGCAAATTAGAAA
mu.wsx.ecd       351  CAAAACAAATAGAAAAAGCCAGCCCTCCGGCCAACCA...GAATT CT CGAGT CGAC A C
wsxfull.13.2.variant 1  .................................................GAATT CT CGAGT CGAC A C
```

```
mu.wsx.ecd            2794 A C C T G A T T A T A G T C T G T T A T C T G G T T A T T G A A T G G A A G A T C C T T A
wsxfull.13.2.variant  2409 A C C C A G T G A T T A C A A G C T A T T G T T A T T T T T T A T T G A G T G G A A A A T C T T A mu.wsx.ecd            2844 A T G A A G A T G A T G G A A T G A A G T G G C T
wsxfull.13.2.variant  2459 A T G A A G A T G G T G A A A T A A A T G G C T T A G A A T C T C T T C A T C T G T T A A G A A G wsxfull.13.2.variant  2509 T A T T A T A T C C A T G A T C A T T T T A T C C C C A T T G A G A A G T A C C A G T T C A G T C T wsxfull.13.2.variant  2559 T T A C C C A A T A T T T A T G G A A G G A G T G G G A A A A C C A A A G A T A A T T A A T A G T T wsxfull.13.2.variant  2609 T C A C T C A A G A T G A T A T T G A A A A A C A C C A G A G T G A T G C A G G T T T A T A T G T A wsxfull.13.2.variant  2659 A T T G T G C C A G T A A T T A T T T C C T C T T C C A T C T T A T T G C T T G G A A C A T T A T T wsxfull.13.2.variant  2709 A A T A T C A C A C C A A A G A A T G A A A A A G C T A T T T T G G G A A G A T G T T C C G A A C C wsxfull.13.2.variant  2759 C C A A G A A T T G T T C C T G G G C A C A A G G A C T T A A T T T T C A G A A G C C A G A A A C G
```

FIG. 5J

```
wsxfull.13.2.variant  2809  TTTGAGCATCTTTTATCAAGCATACAGCATCAGTGACATGTGGTCCTCT
wsxfull.13.2.variant  2859  TCTTTTGGAGCCTGAAACAATTTCAGAAGATATCAGTGTTGATACATCAT
wsxfull.13.2.variant  2909  GGAAAAATAAAGATGAGATGATGCCAAACAACTGTGGTCTCTCTACTTTCA
wsxfull.13.2.variant  2959  ACAACAGATCTTGAAAAGGGTTCTGTTTGTATTAGTGACCAGTTCAACAG
wsxfull.13.2.variant  3009  TGTTAACTTCTCTGAGGCTGAGGGTACTGAGGTAACCTATGAGGACGAAA
wsxfull.13.2.variant  3059  GCCAGAGACAAACCCTTTGTTAAATACGCCACGCTGATCAGCAACTCTAAA
wsxfull.13.2.variant  3109  CCAAGTGAAACTGGTGAAGAACAAGGGCTTATAAATAGTTCAGTCACCAA
wsxfull.13.2.variant  3159  GTGCTTCTCTAGCAAAAATTCTCCGTTGAAGGATTCTTTCTAATAGCT
wsxfull.13.2.variant  3209  CATGGGAGATAGAGGCCCAGGCATTTTTATATTATCAGATCAGCATCCC
```

FIG. 5K

```
wsxfull.13.2.variant  3259  AACATAATTTCACCACACCTCACATTCTCAGAAGGATTGGATGAACTTTTT
wsxfull.13.2.variant  3309  GAAATTGGAGGGAAATTTCCCTGAAGAAATAATGATAAAAAGTCTATCTG
wsxfull.13.2.variant  3359  ATTATTTAGGGGTCACCCTCAATCAAAAAGAGAGAGTGGTGTGCTTTTTG
wsxfull.13.2.variant  3409  ACTGACAAGTCAAGGGTATCGTGCCCATTCCCAGCCCCCTGTTTATTCAC
wsxfull.13.2.variant  3459  GGACATCAGAGTTCTCCAGGACAGTTGCTCACACTTTGTAGAAAATAATA
wsxfull.13.2.variant  3509  TCAAACTTAGGAACTTCTAGTAAGAAGACTTTTTGCATCTTACATGCCTCAA
wsxfull.13.2.variant  3559  TTCCAAACTTGTTCTACTCAGAACTCATAAGATCATGAAAAACAAGATGTG
wsxfull.13.2.variant  3609  TGACCTAACTGTGTAATTTCACTGAAGAAACCTTCAGATTTGTGTTATAA
wsxfull.13.2.variant  3659  TGGGTAATATAAAGTGTAATAGATTATAGTTGTGGGTGGGAGAGAGAAAA
```

FIG. 5L

```
wsxfull.13.2.variant  3709  GAAACCAGAGTCAAATTTGAAAATAATTGTTCCAAATGAATGTTGTCTGT wsxfull.13.2.variant  3759  TTGTTCTCTCTTAGTAACATAGACAAAAATTTGAGAAAGCCTTCATAAG wsxfull.13.2.variant  3809  CCTACCAATGTAGACACGGCTCTTCTATTTTATTCCCAAGCTCTAGTGGGA wsxfull.13.2.variant  3859  AGGTCCCTTGTTTCCAGCTAGAAATAAGCCAACAGACAOCATCTTTTGT wsxfull.13.2.variant  3909  GAGATGTAAATTGTTTTTTCAGAGGGCGTGTTGTTTTACCTCAAGTTTTTG wsxfull.13.2.variant  3959  TTTTGTACCAACACACACACACACATTCTTAACACATGTCCTTGTG wsxfull.13.2.variant  4009  TGTTTTGAGAGTATATTATGTATTTATTTTGTGCTATCAGACTGTAGG wsxfull.13.2.variant  4059  ATTTGAAGTAGGACTTTCCTAAATGTTTAAGATAAACAGAATTC
```

FIG. 5M

Murine

| | | | |
|---|---|---|---|
| -213 | Sense: | GGGTTAAGTTTCCCACCC | (SEQ ID NO:9) |
| | Antisense: | GGGTGGGAAACTTAACCC | (SEQ ID NO:10) |
| | Scrambled: | AGGATACAGTGGGATCCC | (SEQ ID NO:11) |
| -99 | Sense: | GCCCGAGCACTCCTTTAA | (SEQ ID NO:12) |
| | Antisense: | TTAAAGGAGTGCTCCCGC | (SEQ ID NO:13) |
| | Scrambled: | GAGCGGCCCTGTTAGATA | (SEQ ID NO:14) |
| -20 | Sense: | GTATACCTCTGAAGAA | (SEQ ID NO:15) |
| | Antisense: | TTCTTCAGAGGTGTACAC | (SEQ ID NO:16) |
| | Scrambled: | ATGCGAGGCTACTTCTAT | (SEQ ID NO:17) |
| +84 | Sense: | CTCTCCTGGAAATTTAA | (SEQ ID NO:18) |
| | Antisense: | TTAAATTTCCAGGGAGAG | (SEQ ID NO:19) |
| | Scrambled: | ATTTGAAGGAGTTAAGCC | (SEQ ID NO:20) |
| +211 | Sense: | AATTTAATTCAAGTGGTA | (SEQ ID NO:21) |
| | Antisense: | TACCAGTTGAATTAAATT | (SEQ ID NO:22) |
| | Scrambled: | GTATCACTTCATAATATA | (SEQ ID NO:23) |

Human

| | | | |
|---|---|---|---|
| 5L | Sense: | GATGGTCAGGGTGAACTG | (SEQ ID NO:24) |
| | Antisense: | CAGTTCACCCTGACCATC | (SEQ ID NO:25) |
| | Scrambled: | GAGGCGAATGTGCGGATT | (SEQ ID NO:26) |
| +85 | Sense: | CTTAAATCTCCAAGGAGT | (SEQ ID NO:27) |
| | Antisense: | ACTCCTTGGAGATTTAAG | (SEQ ID NO:28) |
| | Scrambled: | AAGTCTTAAGCCAGACTT | (SEQ ID NO:29) |
| -47 | Sense: | TCTAAGGCACATCCCAGC | (SEQ ID NO:30) |
| | Antisense: | GCTGGGATGTGCCTTAGA | (SEQ ID NO:31) |
| | Scrambled: | CGCAATGAATTGACCCCC | (SEQ ID NO:32) |
| -20 | Sense: | TACTTCAGAGAAGTACAC | (SEQ ID NO:33) |
| | Antisense: | GTGTACTTCTCTGAAGTA | (SEQ ID NO:34) |
| | Scrambled: | GAATCACGGTAACTATCA | (SEQ ID NO:35) |
| +185 | Sense: | CAGCTGTCTCATAATGTC | (SEQ ID NO:36) |
| | Antisense: | GACATTATGAGACAGCTG | (SEQ ID NO:37) |
| | Scrambled: | TTCGTCAAGCCATCTGAT | (SEQ ID NO:38) |

FIG. 7

LEPTIN RECEPTOR HAVING A WSX MOTIF

This is a non-provisional application filed under 37 CFR §1.53(b) claiming priority under 35 USC §119(e) to provisional application Ser. No. 60/064,855 filed Jan. 8, 1996.

BACKGROUND OF THE INVENTION

1. Field of the Invention

The present invention pertains generally to the WSX receptor. In particular, the invention relates to native sequence WSX receptor, WSX receptor variants, WSX receptor extracellular domain, chimeric WSX receptor and antibodies which bind to the WSX receptor (including agonist and neutralizing antibodies), as well as the various uses for these molecules.

2. Description of Related Art

Hematopoietic growth factors (reviewed in D'Andrea, *NEJM* 330(12): 839–846 (1994)) have been shown to enhance growth and/or differentiation of blood cells via activation of receptors present on the surface of blood progenitor cells of the bone marrow. While some of these growth factors stimulate proliferation of restricted lineages of blood cells, others enhance proliferation of multiple lineages of blood cells. For example, erythropoietin (EPO) supports the proliferation of erythroid cells, whereas interleukin-3 (IL-3) induces proliferation of erythroid and myeloid lineages and is therefore considered a multi-lineage factor.

In recent years, several hematopoietic growth factor receptors have been isolated. Due to their low abundance and their existence in both high-affinity and low-affinity forms, biochemical characterization of these receptors has been hampered.

Cytokine receptors frequently assemble into multi-subunit complexes. Sometimes, the subunit of this complex is involved in binding the cognate growth factor and the β-subunit may contain an ability to transduce a signal to the cell. These receptors have been assigned to three subfamilies depending on the complexes formed. Subfamily 1 includes the receptors for EPO, granulocyte colony-stimulating factor (G-CSF), interleukin-4 (IL-4), interleukin-7 (IL-7), growth hormone (GH) and prolactin (PRL). Ligand binding to receptors belonging to this subfamily is thought to result in homodimerization of the receptor. Subfamily 2 includes receptors for IL-3, granulocyte-macrophage colony-stimulating factor (GM-CSF), interleukin-5 (IL-5), interleukin-6 (IL-6), leukemia inhibitory factor (LIF), oncostatin M (OSM) and ciliary neurotrophic factor (CNTF). Subfamily 2 receptors are heterodimers having an α-subunit for ligand binding and β-subunit (either the shared β-subunit of the IL-3, GM-CSF and IL-5 receptors or the gp 130 subunit of the IL-6, LIF, OSM and CNTF receptors) for signal transduction. Subfamily 3 contains only the interleukin-2 (IL-2) receptor. The β and γ subunits of the IL-2 receptor complex are cytokine-receptor polypeptides which associate with the α-subunit of the unrelated Tac antigen.

SUMMARY OF THE INVENTION

According to a first aspect, the invention is concerned with the WSX cytokine receptor and a soluble form of the receptor which is the WSX receptor extracellular domain (ECD). The WSX receptor polypeptides are optionally conjugated with, or fused to, molecules which increase the serum half-lives thereof and can be formulated as pharmaceutical compositions comprising the polypeptide and a physiologically acceptable carrier.

In certain embodiments, the WSX receptor ECD may be used as an antagonist insofar as it may bind to WSX ligand and thereby reduce activation of endogenous WSX receptor. This may be useful in conditions characterized by excess levels of WSX ligand and/or excess WSX receptor activation in a mammal. WSX receptor ECD may, for example, be used to treat metabolic disorders (e.g., anorexia or steroid-induced truncalobesity), stem cell tumors and other tumors which express WSX receptor.

Pharmaceutical compositions of the WSX receptor ECD may further include a WSX ligand. Such dual compositions may be beneficial where it is therapeutically useful to prolong the half-life of WSX ligand and/or activate endogenous WSX receptor directly as a heterotrimeric complex.

The invention also relates to chimeric WSX receptor molecules, such as WSX receptor immunoadhesins (having long half-lives in the serum of a patient treated therewith) and epitope tagged WSX receptor. Immunoadhesins may be employed as WSX receptor antagonists in conditions or disorders in which neutralization of WSX receptor biological activity may be beneficial. Bispecific immunoadhesins (combining a WSX receptor ECD with a domain of another cytokine receptor) may form high affinity binding complexes for WSX ligand.

The invention further provides methods for identifying a molecule which binds to and/or activates the WSX receptor. This is useful for discovering molecules (such as peptides, antibodies, and small molecules) which are agonists or antagonists of the WSX receptor. Such methods generally involve exposing an immobilized WSX receptor to a molecule suspected of binding thereto and determining binding of the molecule to the immobilized WSX receptor and/or evaluating whether or not the molecule activates (or blocks activation on the WSX receptor. In order to identify such WSX ligands, the WSX receptor may be expressed on the surface of a cell and used to screen libraries of synthetic compounds and naturally occurring compounds (e.g., endogenous sources of such naturally occurring compounds, such as serum). The WSX receptor can also be used as a diagnostic tool for measuring serum levels of endogenous WSX ligand.

In a further embodiment, a method for purifying a molecule which binds to the WSX receptor is provided. This can be used in the commercial production and purification of therapeutically active molecules which bind to this receptor. In the method, the molecule of interest (generally a composition comprising one or more contaminants) is adsorbed to immobilized WSX receptor (e.g., WSX receptor immunoadhesin immobilized on a protein A column). The contaminants, by virtue of their inability to bind to the WSX receptor, will generally flow through the column. Accordingly, it is then possible to recover the molecule of interest from the column by changing the elution conditions, such that the molecule no longer binds to the immobilized receptor.

In further embodiments, the invention provides antibodies that specifically bind to the WSX receptor. Preferred antibodies are monoclonal antibodies which are non-immunogenic in a human and bind to an epitope in the extracellular domain of the receptor. Preferred antibodies bind the WSX receptor with an affinity of at least about $10^6$ L/mole, more preferably $10^7$ L/mole.

Antibodies which bind to the WSX receptor may optionally be fused to a heterologous polypeptide and the antibody or fusion thereof may be used to isolate and purify WSX receptor from a source of the receptor.

In a further aspect, the invention provides a method for detecting the WSX receptor in vitro or in vivo comprising contacting the antibody with a sample suspected of containing the receptor and detecting if binding has occurred. Based on the observation herein that CD34+ cells possess WSX receptor, use of WSX antibodies for identification and/or enrichment of stem cell populations (in a similar manner to that in which CD34 antibodies are presently used) is envisaged.

For certain applications, it is desirable to have an agonist antibody which can be screened for as described herein. Such agonist antibodies are useful for activating the WSX receptor for in vitro uses whereby enhancement of proliferation and/or differentiation of a cell comprising the receptor is desired. Furthermore, these antibodies may be used to treat conditions in which an effective amount of WSX receptor activation leads to a therapeutic benefit in the mammal treated therewith. For example, the agonist antibody can be used to enhance survival, proliferation and/or differentiation of a cell comprising the WSX receptor. In particular, agonist antibodies and other WSX ligands may be used to stimulate proliferation of stem cells/progenitor cells either in vitro or in vivo. Other potential therapeutic applications include the use of agonist antibodies to treat metabolic disorders (such as obesity and diabetes) and to promote kidney, liver or lung growth and/or repair (e.g., in renal failure).

For therapeutic applications it is desirable to prepare a composition comprising the agonist antibody and a physiologically acceptable carrier. Optionally, such a composition may further comprise one or more cytokines.

In other embodiments, the antibody is a neutralizing antibody. Such molecules can be used to treat conditions characterized by unwanted or excessive activation of the WSX receptor.

In addition to the above, the invention provides isolated nucleic acid molecules, expression vectors and host cells encoding the WSX receptor which can be used in the recombinant production of WSX receptor as described herein. The isolated nucleic acid molecules and vectors are also useful for gene therapy applications to treat patients with WSX receptor defects and/or to increase responsiveness of cells to WSX ligand.

BRIEF DESCRIPTION OF THE DRAWINGS

Figure 1B:
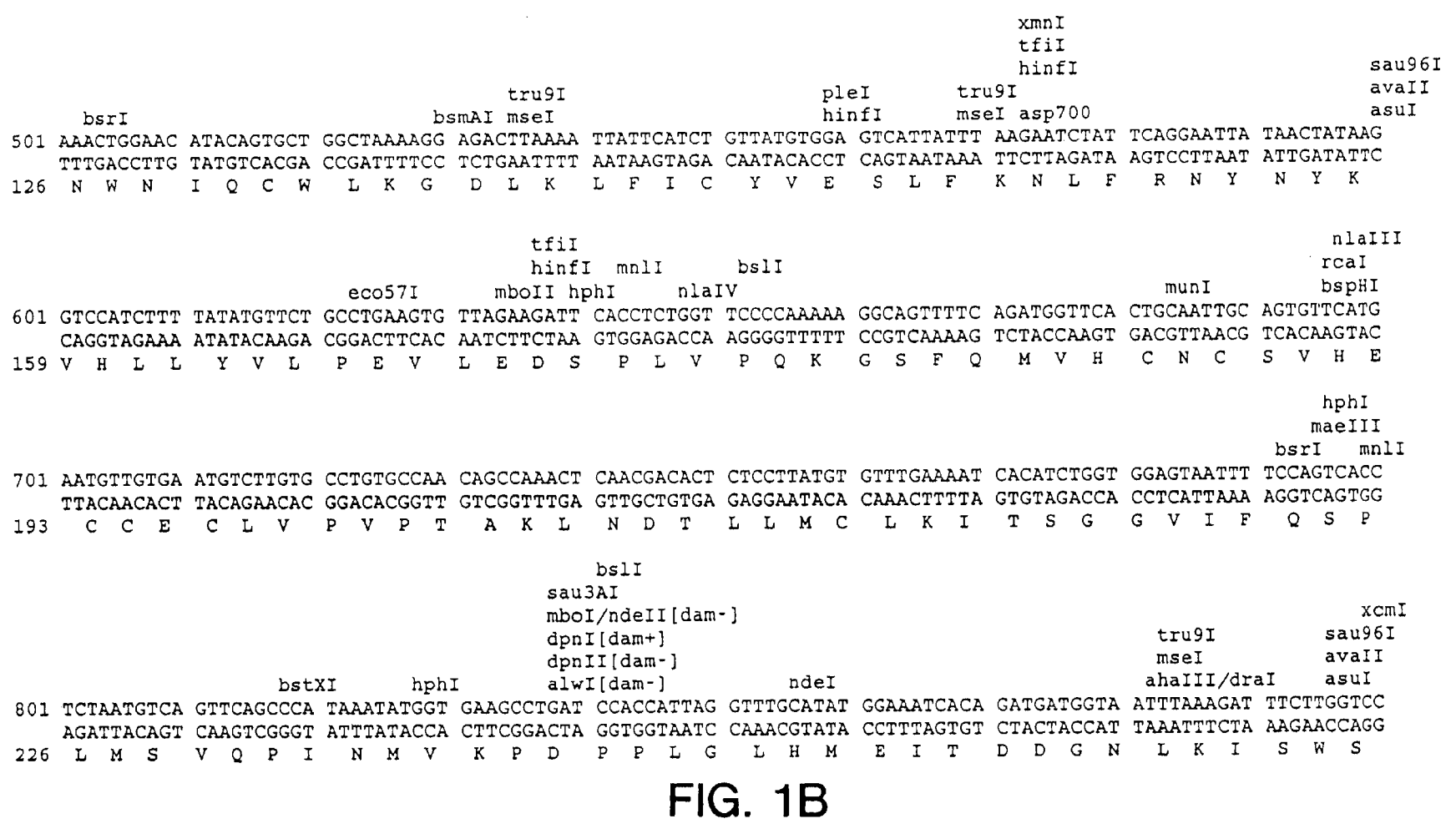
Figure 1G:
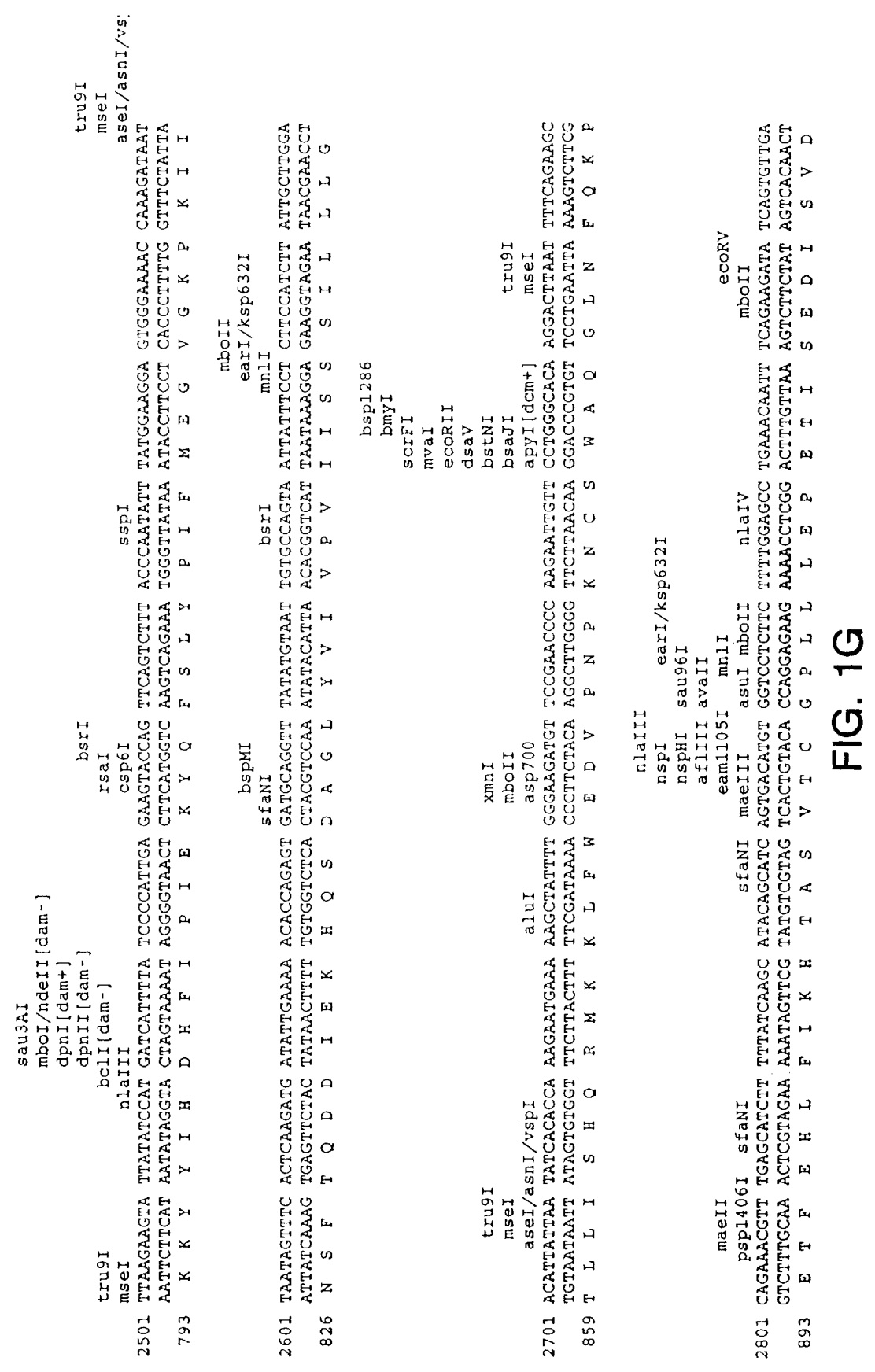
Figure 1H:
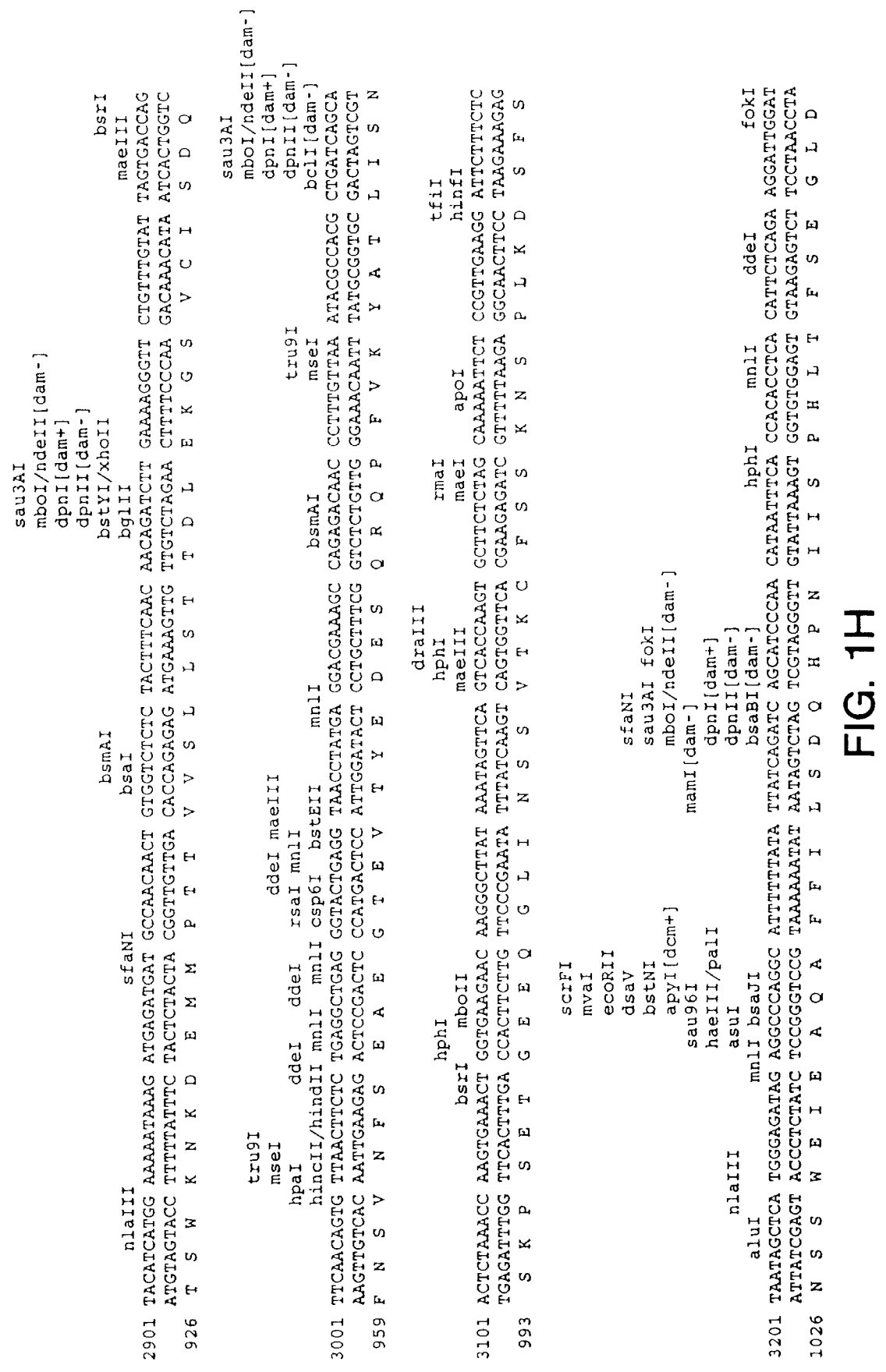

FIGS. 1A–J together depict the double stranded nucleotide (SEQ ID NO:1) and deduced amino acid sequence (SEQ ID NO:2) encoding full length human WSX receptor variant 13.2. Nucleotides are numbered at the beginning of the sense strand. Amino acid residues are numbered at the beginning of the amino acid sequence. Restriction enzyme sites are depicted above the nucleotide sequence.

FIGS. 2A–D together depict an amino acid sequence alignment of full length human WSX receptor variants 6.4 (SEQ ID NO:3), 12.1 (SEQ ID NO:4) and 13.2 (SEQ ID NO:2), respectively. Homologous residues are boxed. WSX receptor variants 6.4, 12.1 and 13.2 are native sequence human WSX receptor variants which, without being bound to any one theory, appear to be generated by alternate splicing of WSX receptor mRNA. The putative signal peptide, transmembrane, Box 1, Box 2, and Box 3 domains are indicated. The extracellular and cytoplasmic domains are amino- and carboxy-terminal, respectively, to the transmembrane domain. The Box 1–3 domains shown correspond to the box 1–3 motifs described in Baumann et al., *Mol. Cell. Biol.* 14(1):138–146 (1994).

Figure 3A:
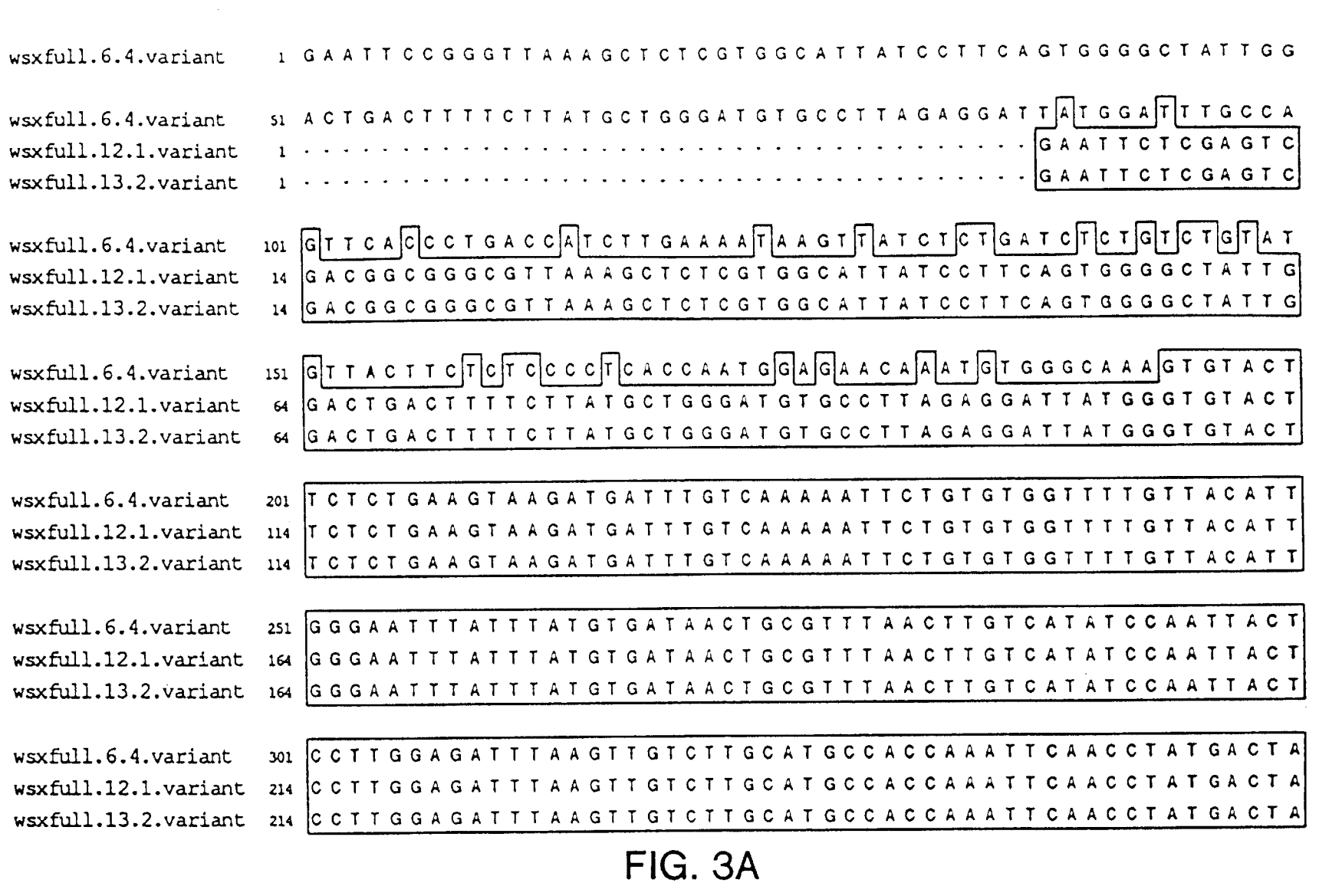
Figure 3F:
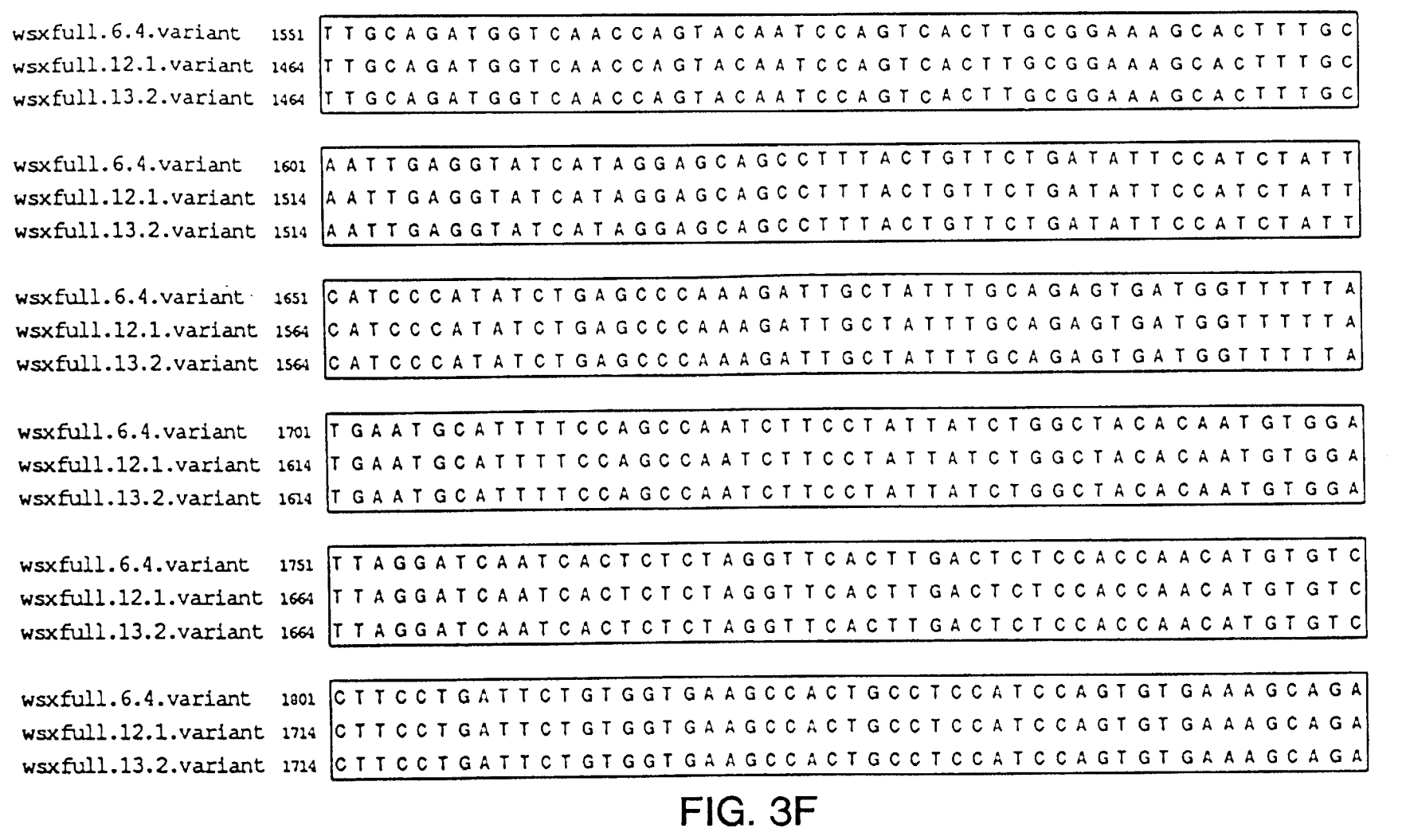
Figure 3H:
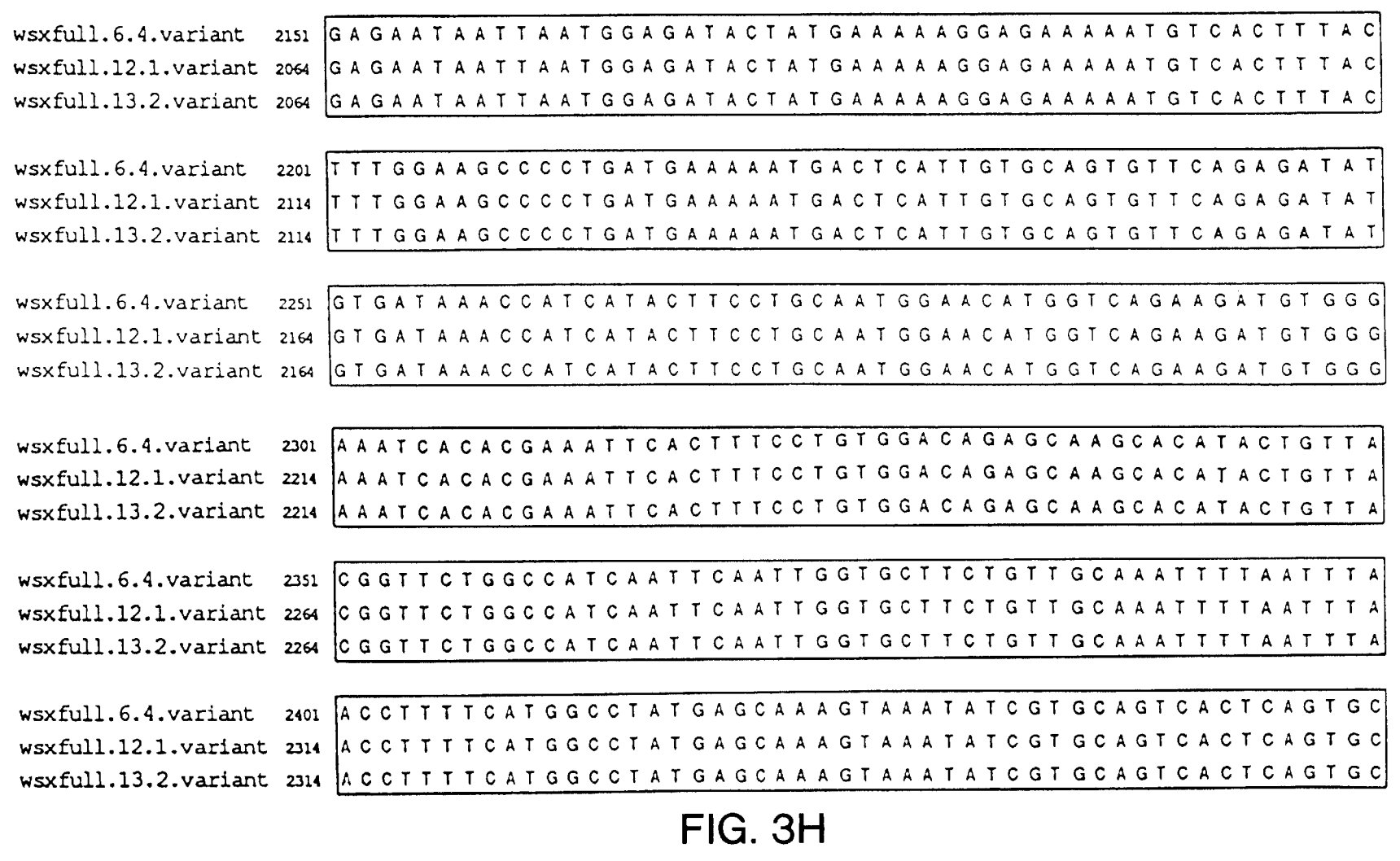
Figure 3I:
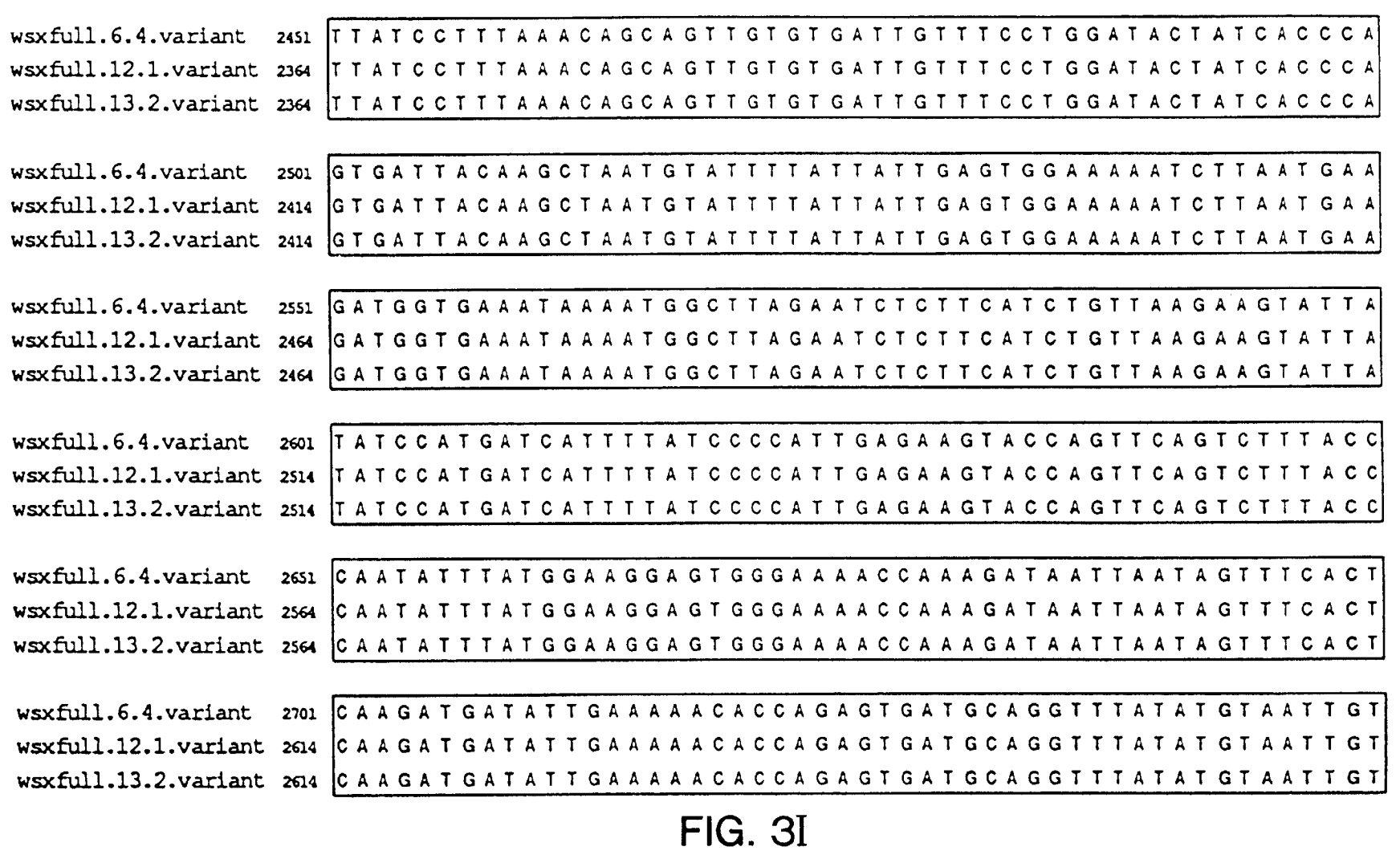
Figure 3J:
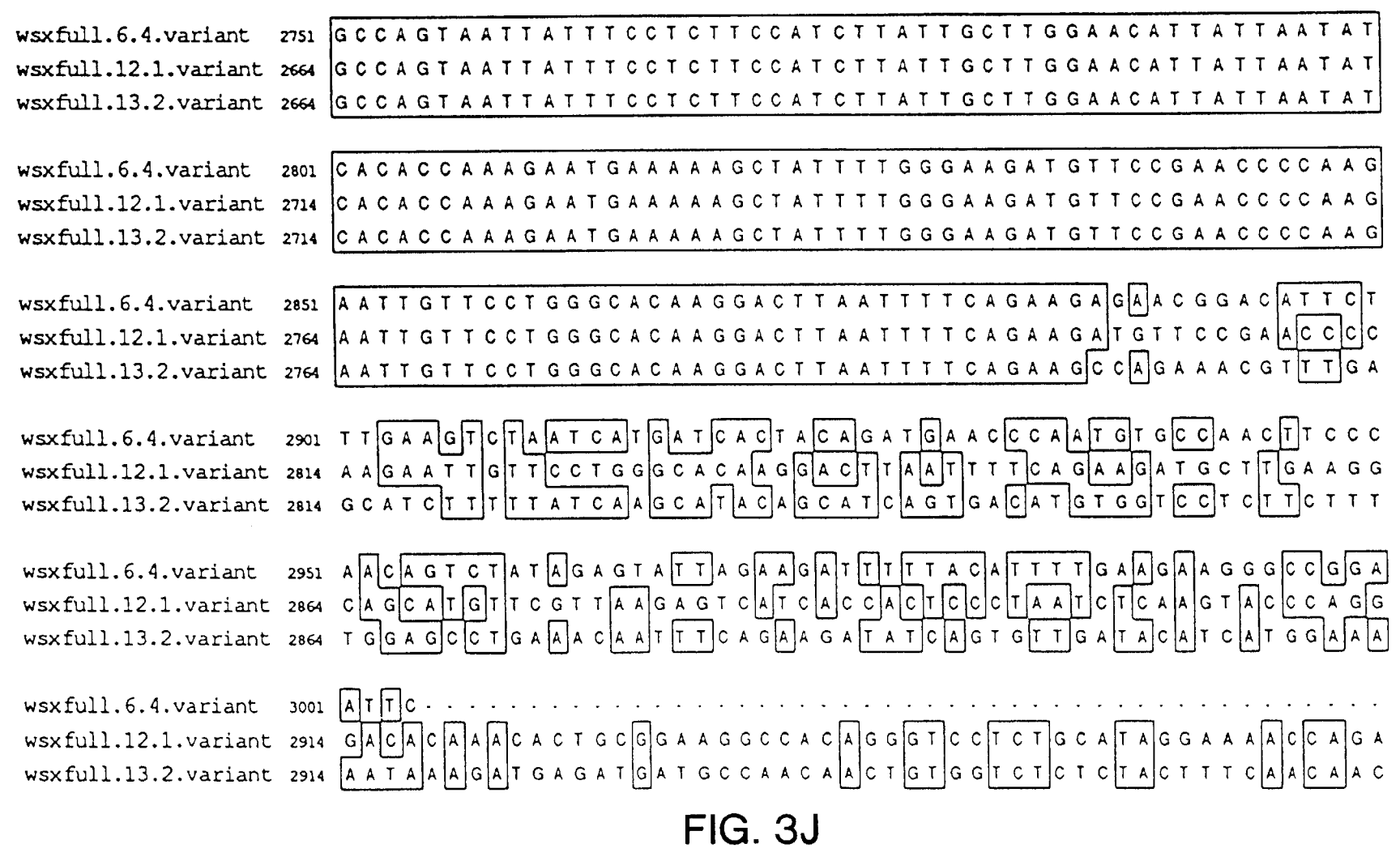
Figure 3K:
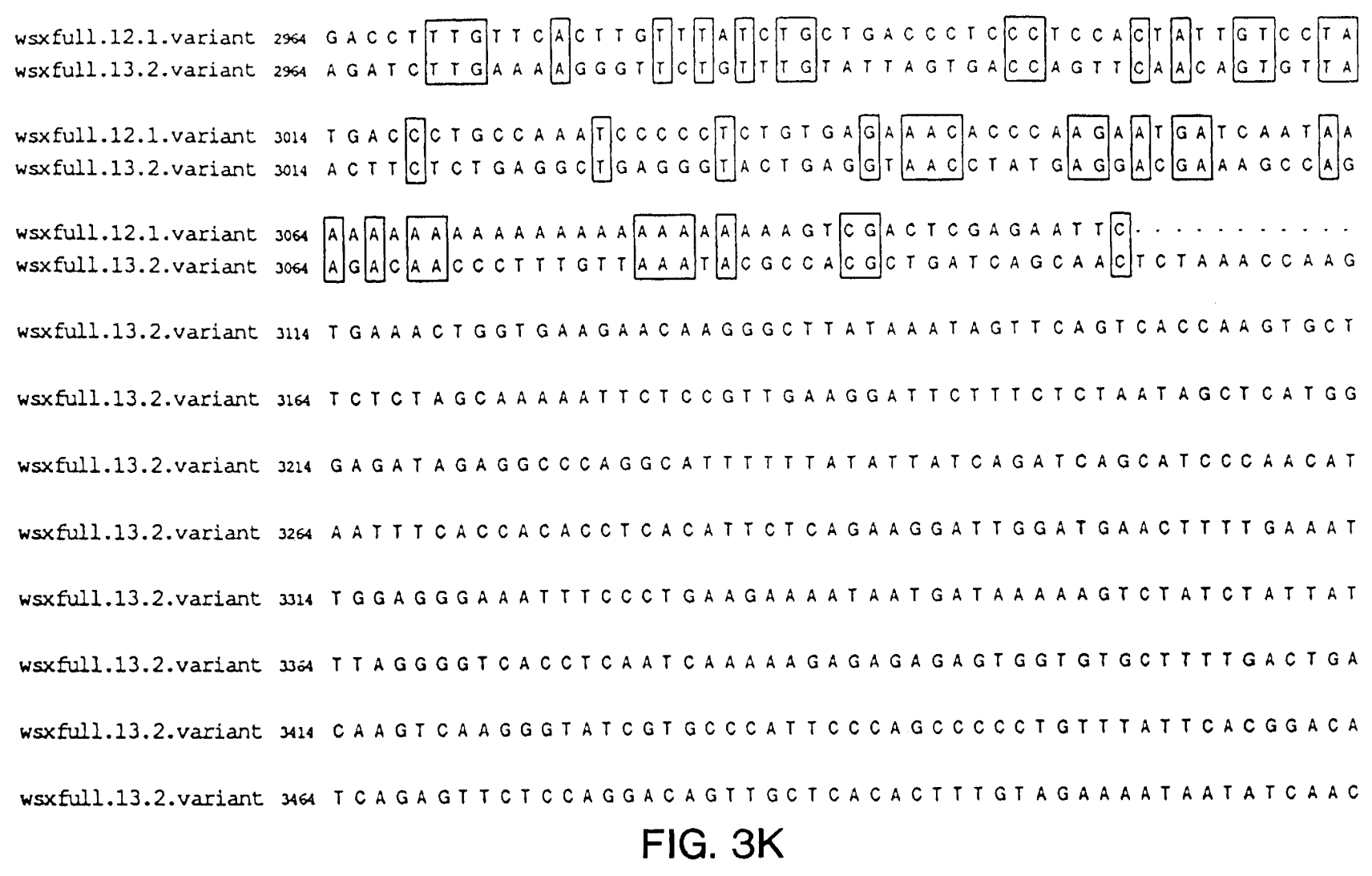

FIGS. 3A–L together depict an alignment of the nucleotide sequences encoding human WSX receptor variants 6.4 (SEQ ID NO:5), 12.1 (SEQ ID NO:6) and 13.2 (SEQ ID NO:1), respectively.

FIGS. 4A–D depict an alignment of the full length human WSX receptor variant 13.2 amino acid sequence (top) with that of partial murine WSX receptor extracellular domain sequence (bottom) (SEQ ID NO:7) obtained as described in Example 7. The putative murine signal peptide is marked with an arrow.

Figure 5B:
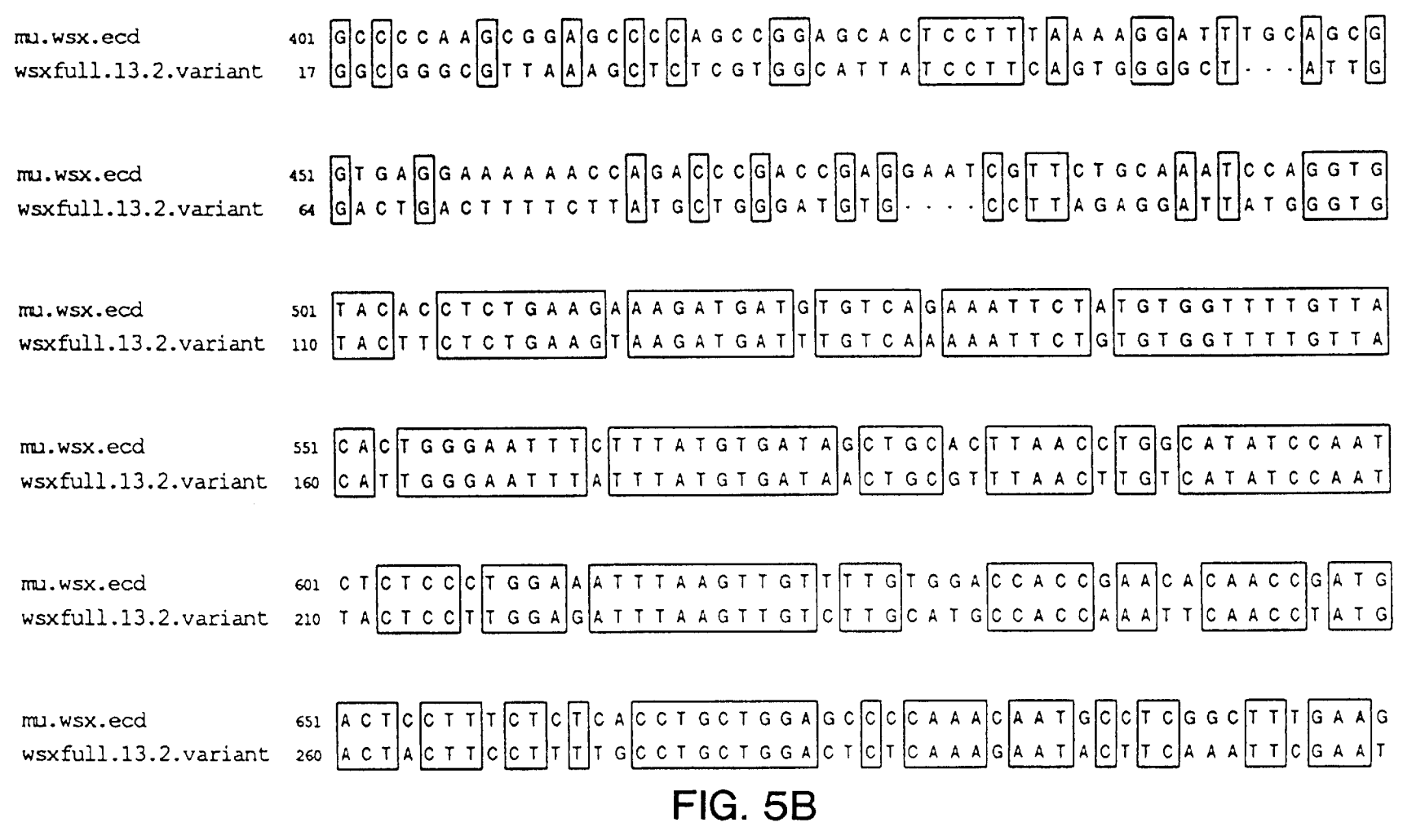
Figure 5C:
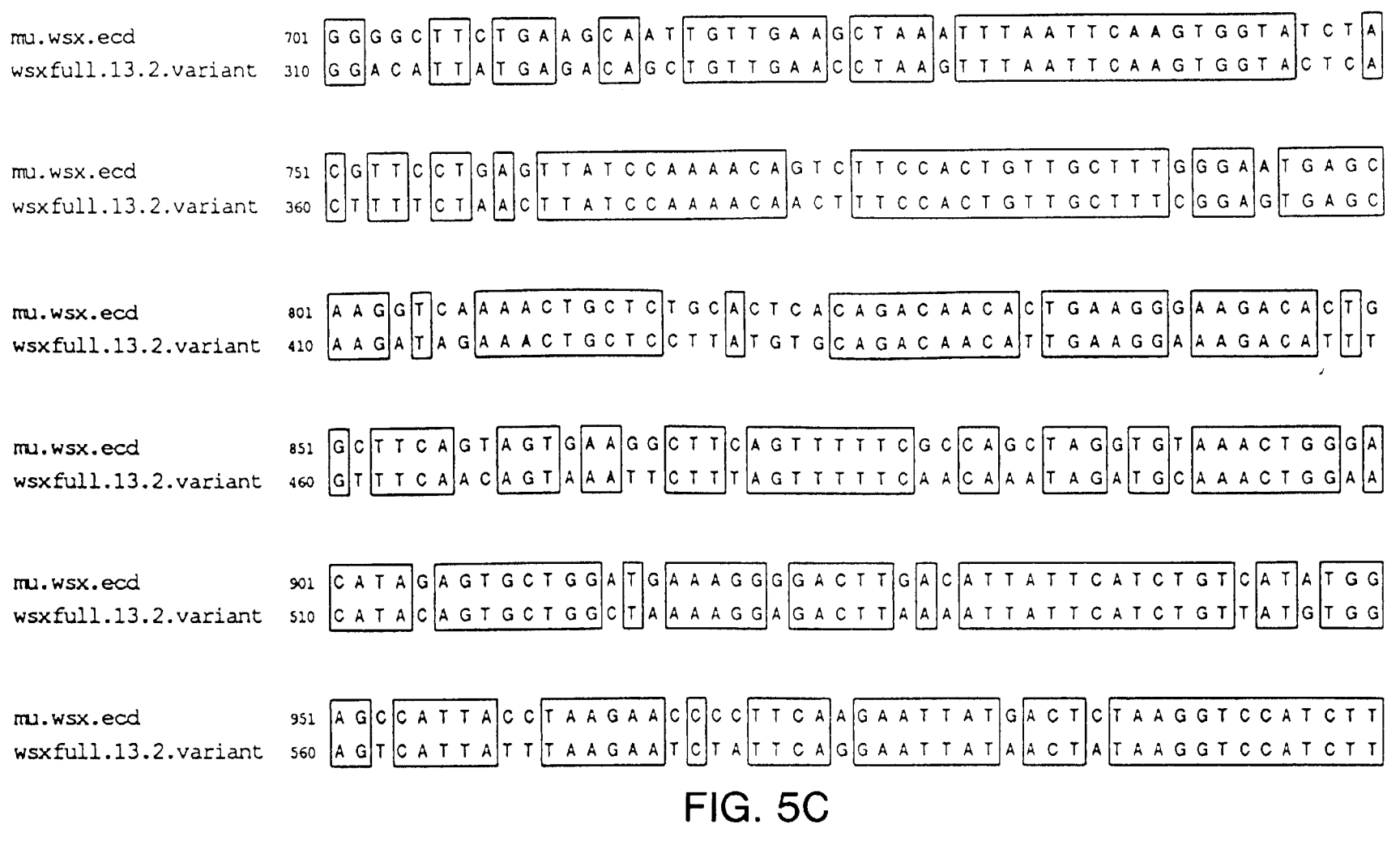
Figure 5D:
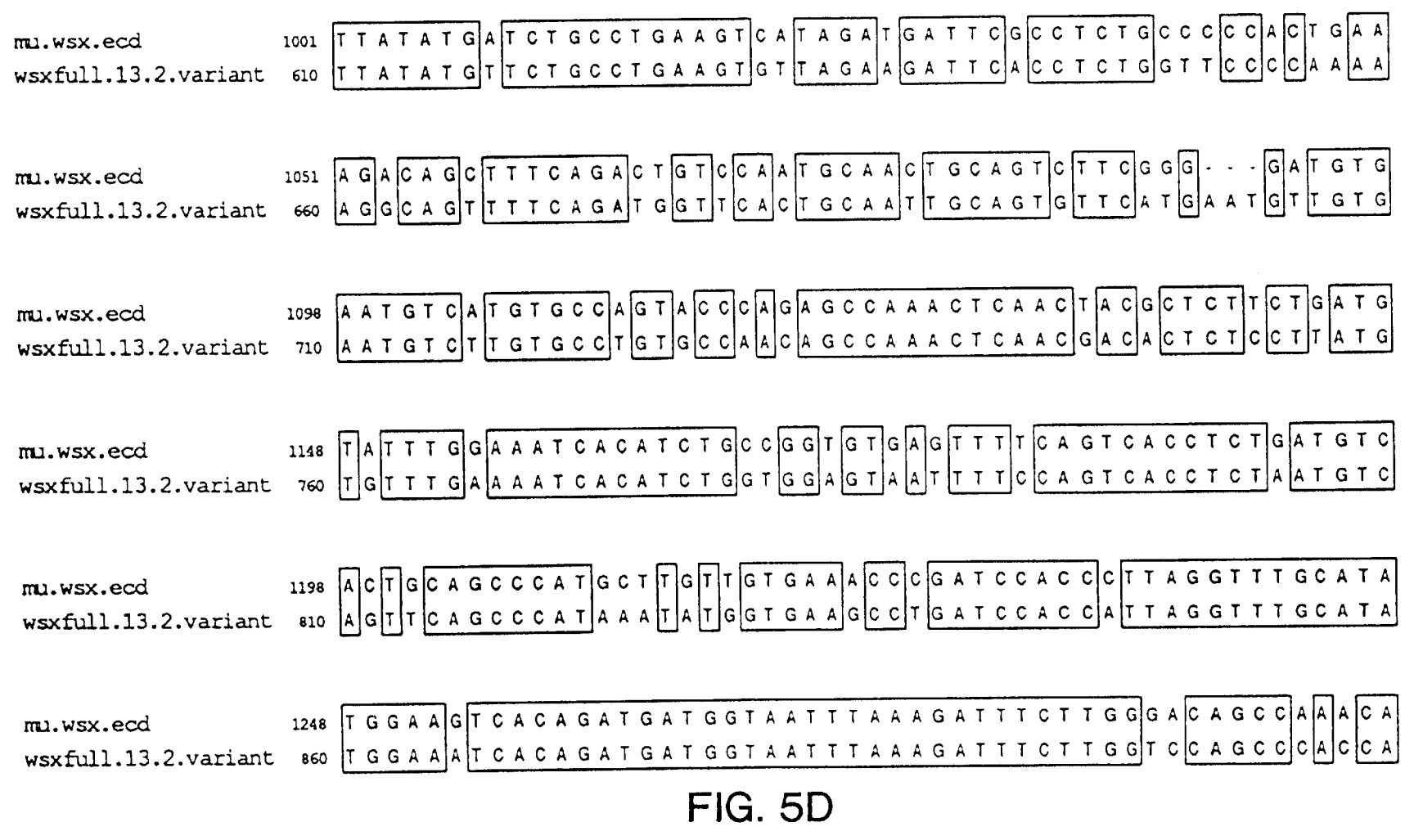
Figure 5E:
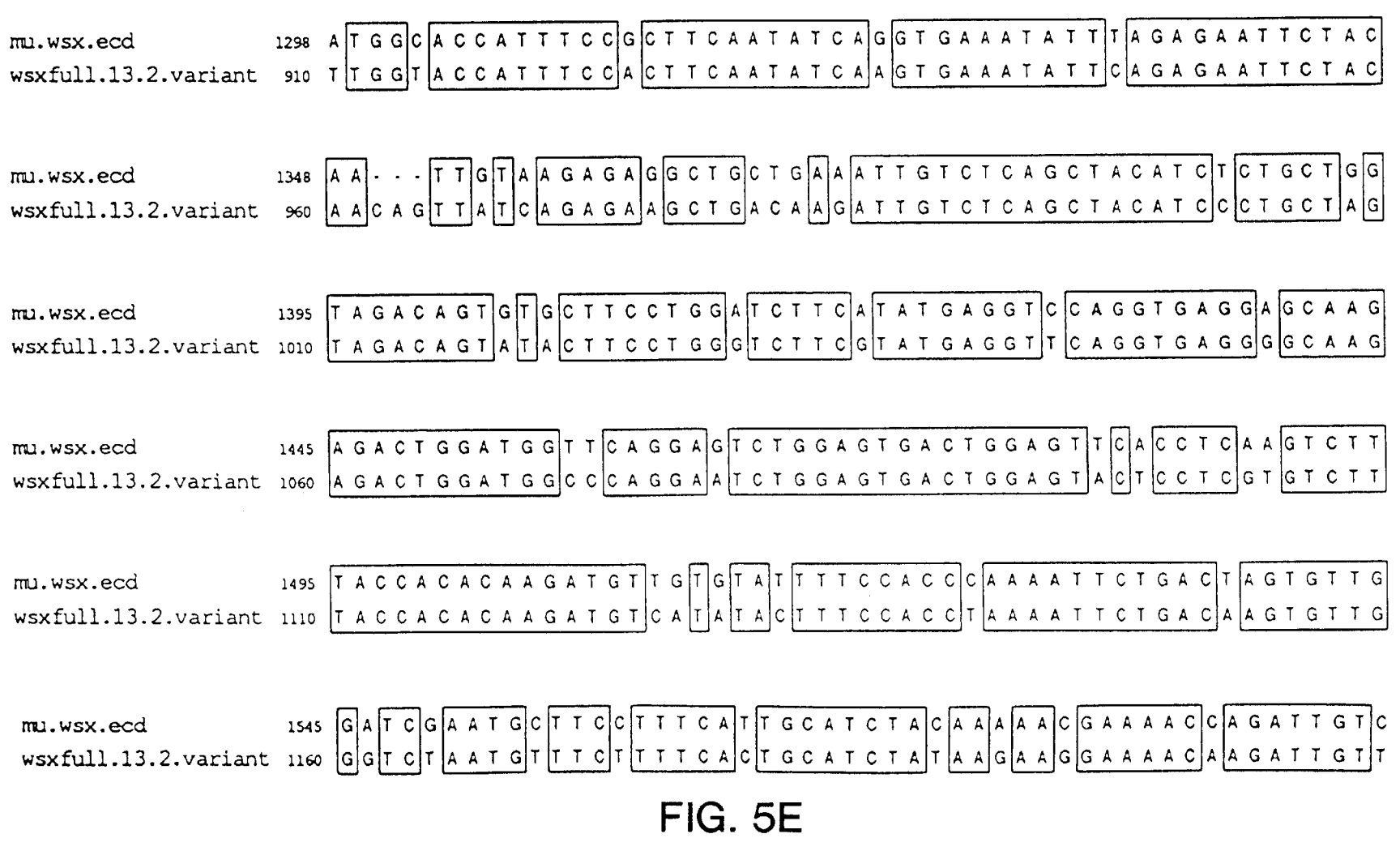
Figure 5F:
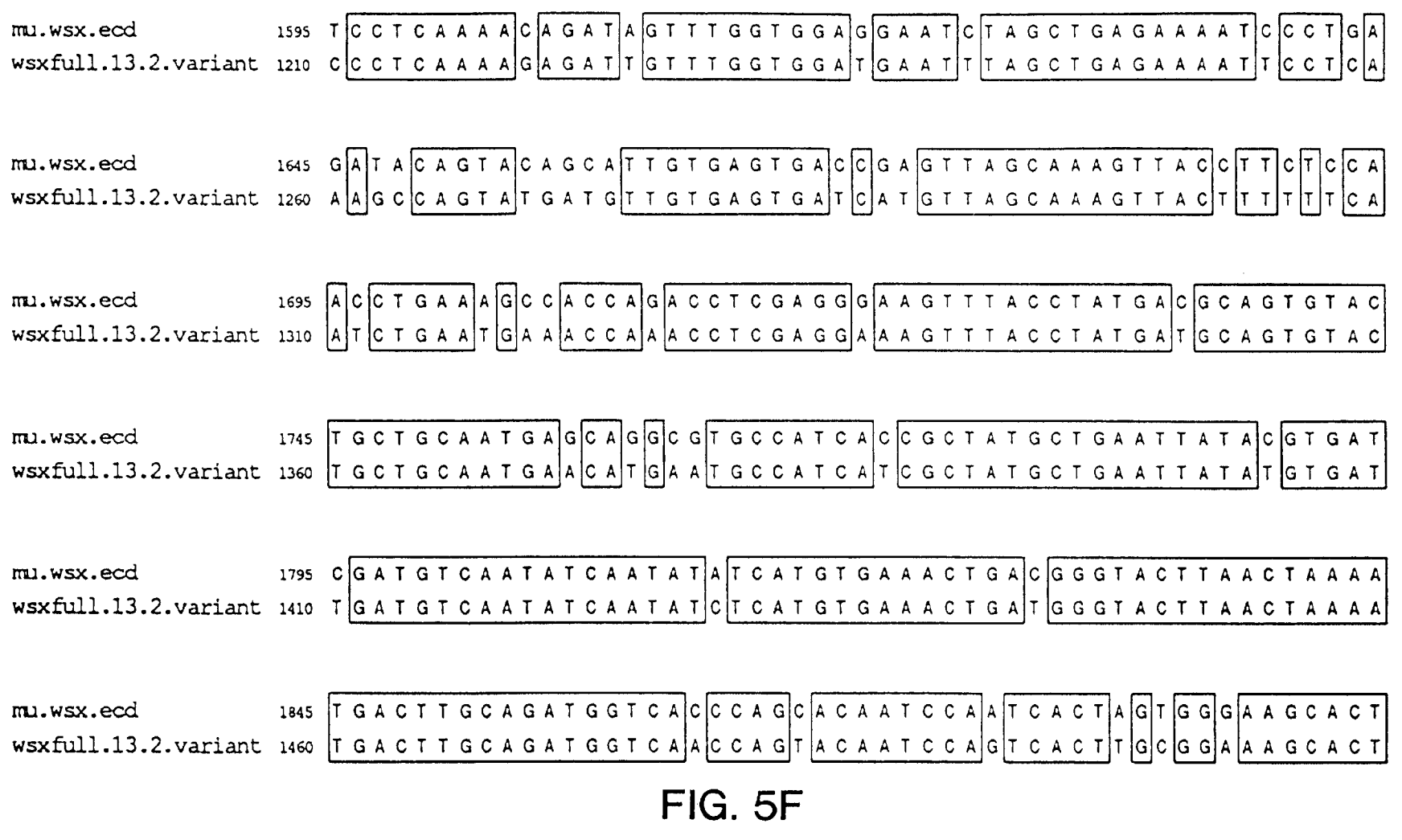
Figure 5G:
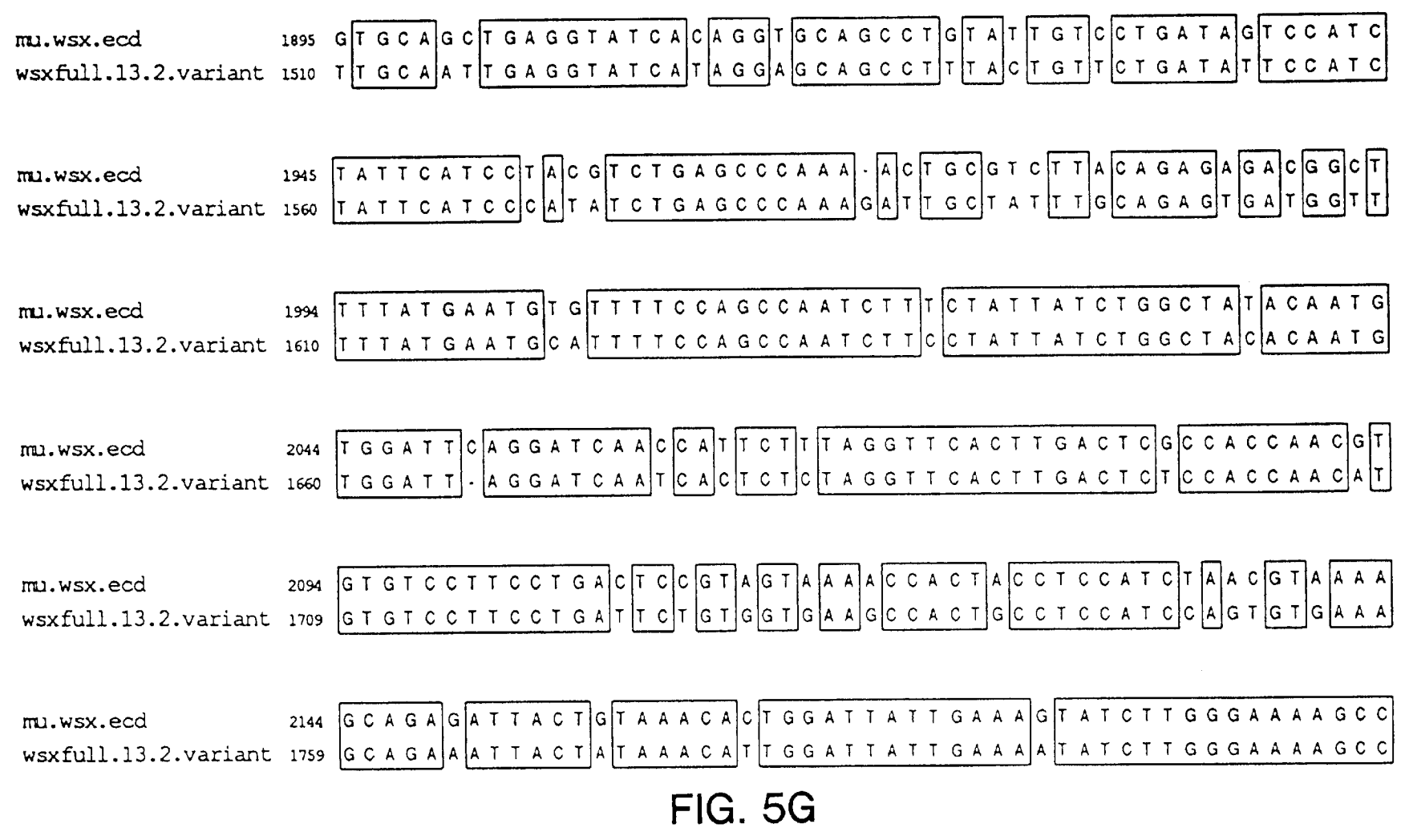
Figure 5H:
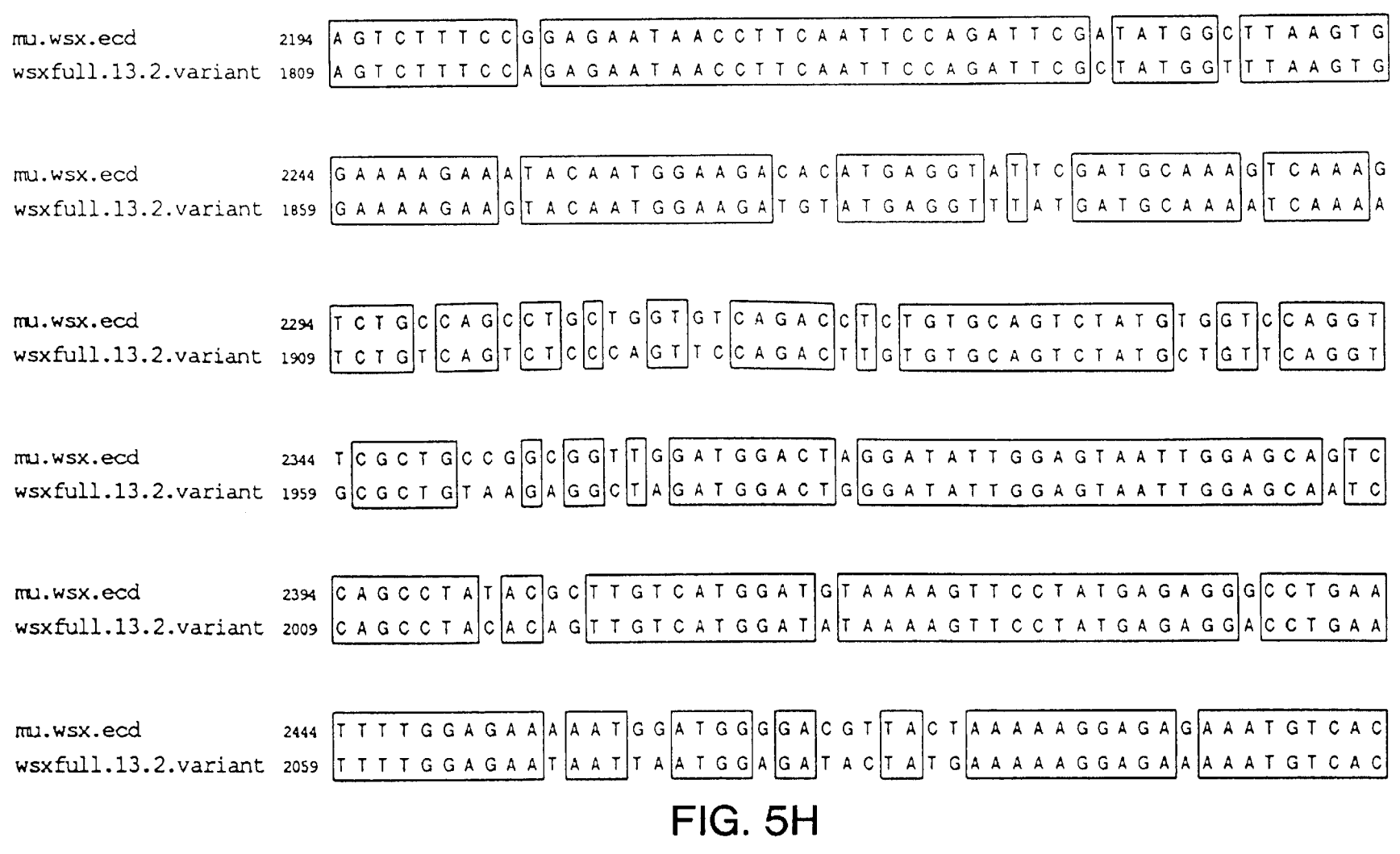
Figure 5I:
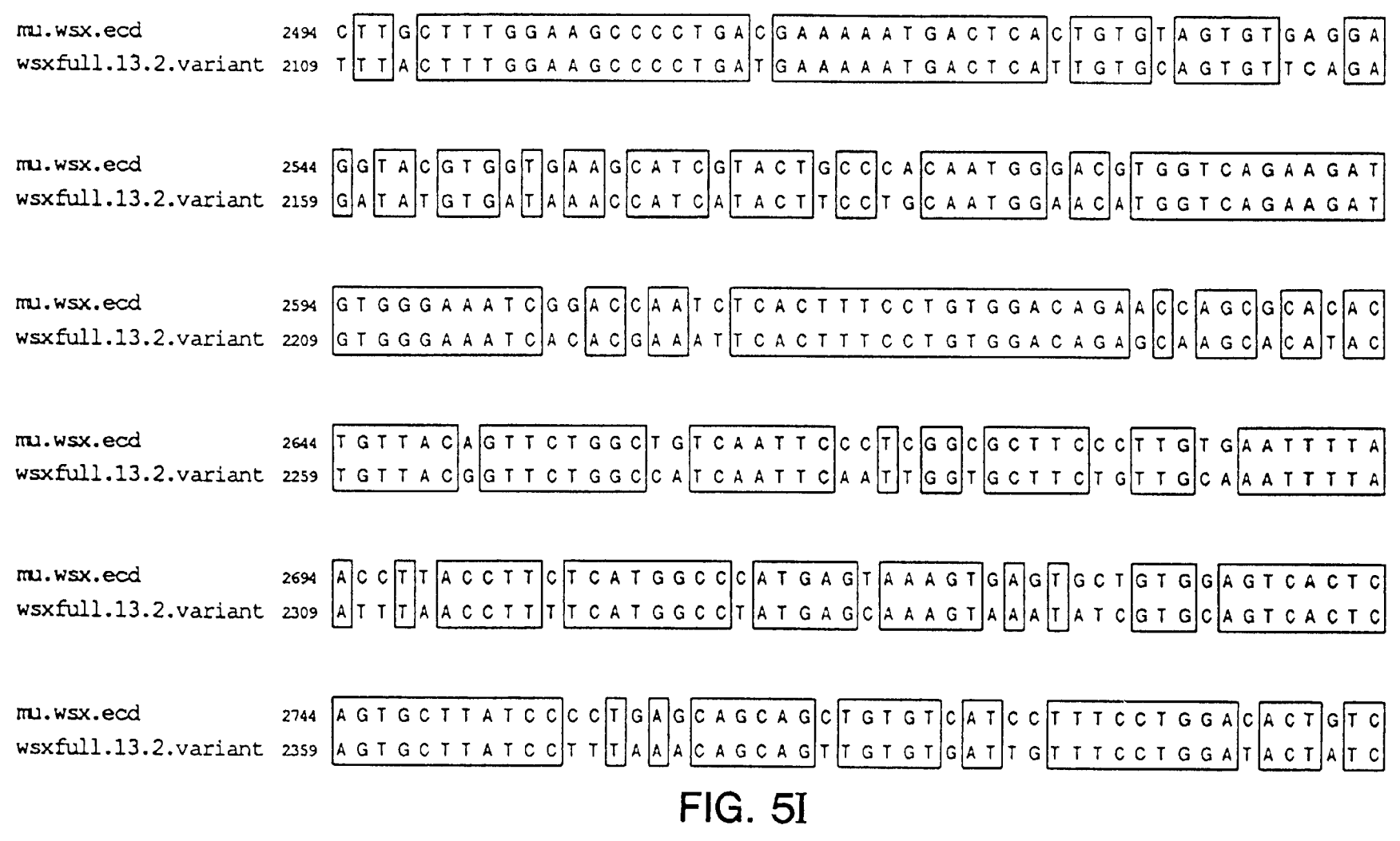

FIGS. 5A–M represent an alignment of the nucleotide sequences encoding human WSX receptor variant 13.2 (SEQ ID NO:1) (bottom) and partial murine WSX receptor extracellular domain (top) (SEQ ID NO:8), respectively.

FIG. 7 shows the human and murine oligonucleotides (SEQ ID NOS:9–38, respectively) used for the antisense experiment described in Example 8.

DETAILED DESCRIPTION OF THE PREFERRED EMBODIMENTS

I. Definitions

Figure 6:
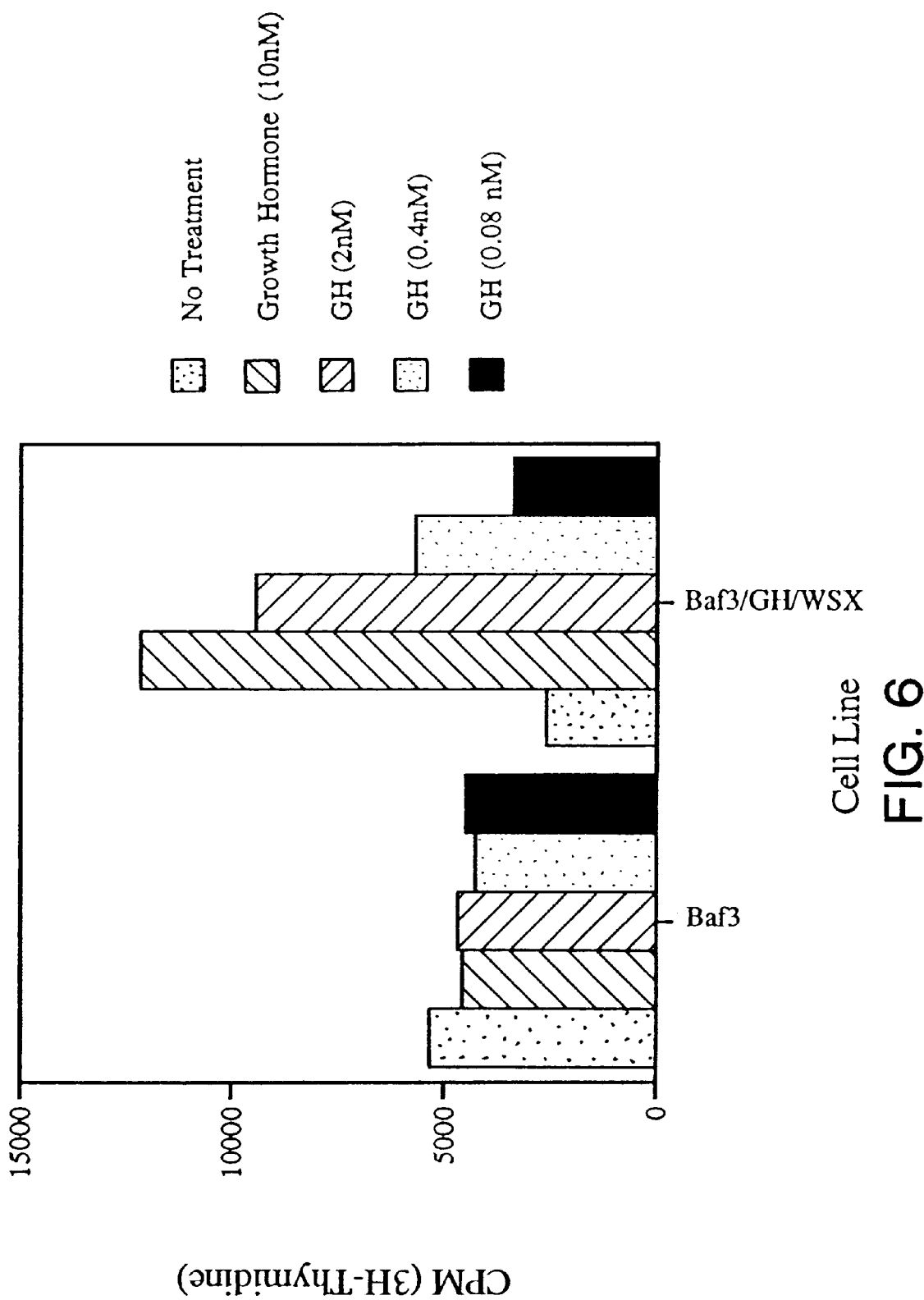
FIG. 6 is a bar graph depicting results of the thymidine incorporation assay described in Example 5. $^3$H-thymidine incorporation (counts per minute, CPM) in parental Baf3 cells or Baf3 cells electroporated with GH/WSX chimera in the presence of varying concentrations of human growth hormone (GH) is shown.

In describing the present invention, the following terms will be employed, and are intended to be defined as indicated below.

The terms "WSX receptor" or "WSX receptor polypeptide" when used herein encompass native sequence WSX receptor; WSX receptor variants; WSX extracellular domain; and chimeric WSX receptor (each of which is defined herein). Optionally, the WSX receptor is not associated with native glycosylation. "Native glycosylation" refers to the carbohydrate moieties which are covalently attached to WSX receptor when it is produced in the mammalian cell from which it is derived in nature. Accordingly, human WSX receptor produced in a non-human cell is an example of a WSX receptor which is "not associated with native glycosylation". Sometimes, the WSX receptor is unglycosylated (e.g., as a result of being produced recombinantly in a prokaryote).

A "native sequence WSX receptor" comprises a polypeptide having the same amino acid sequence as a WSX receptor derived from nature. Thus, a native sequence WSX receptor can have the amino acid sequence of naturally occurring human WSX receptor, murine WSX receptor, or WSX receptor from any other mammalian species. Such native sequence WSX receptor polypeptides can be isolated from nature or can be produced by recombinant or synthetic means. The term "native sequence WSX receptor" specifically encompasses naturally-occurring truncated forms of the WSX receptor, naturally-occurring variant forms (e.g., alternatively spliced forms such as human WSX receptor variants 6.4, 12.1 and 13.2 described herein) and naturally-occurring allelic variants of the WSX receptor. The preferred native sequence WSX receptor is a mature native sequence human WSX receptor, such as human WSX receptor variant 6.4, human WSX receptor variant 12.1 or human WSX receptor variant 13.2 (each shown in FIGS. 2A–D). Most preferred is mature human WSX receptor variant 13.2.

The "WSX receptor extracellular domain" (ECD) is a form of the WSX receptor which is essentially free of the transmembrane and cytoplasmic domains of WSX receptor, i.e., has less than 1% of such domains, preferably 0.5 to 0% of such domains, and more preferably 0.1 to 0% of such domains. Ordinarily, the WSX receptor ECD will have an amino acid sequence having at least about 95% amino acid sequence identity with the amino acid sequence of the ECD of WSX receptor indicated in FIGS. 2A–D for human WSX receptor variants 6.4, 12.1 and 13.2, preferably at least about 98%, more preferably at least about 99% amino acid sequence identity, and thus includes WSX receptor variants as defined below.

"WSX receptor variant" means a biologically active WSX receptor as defined below having less than 100% sequence identity with WSX receptor having the deduced amino acid sequence shown in FIGS. 1A–J for human WSX receptor variant 13.2. Such WSX receptor variants include WSX receptor polypeptides wherein one or more amino acid residues are added at the N- or C-terminus of, or within, the human WSX receptor sequence; from about one to thirty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active WSX receptor variant will have an amino acid sequence having at least about 90% amino acid sequence identity with human WSX receptor variant 13.2 shown in FIGS. 1A–J, preferably at least about 95%, more preferably at least about 99%.

A "chimeric WSX receptor" is a polypeptide comprising full-length WSX receptor or one or more domains thereof (e.g., the extracellular domain) fused or bonded to heterologous polypeptide. The chimeric WSX receptor will generally share at least one biological property in common with human WSX receptor variant 13.2. Examples of chimeric WSX receptors include immunoadhesins and epitope tagged WSX receptor.

The term "immunoadhesin" is used interchangeably with the expression "WSX receptor-immunoglobulin chimera" and refers to a chimeric molecule that combines a portion of the WSX receptor (generally the extracellular domain thereof) with an immunoglobulin sequence. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

The term "epitope tagged" when used herein refers to a chimeric polypeptide comprising WSX receptor fused to a "tag polypeptide". The tag polypeptide has enough residues to provide an epitope against which an antibody thereagainst can be made, yet is short enough such that it does not interfere with biological activity of the WSX receptor. The tag polypeptide preferably also is fairly unique so that the antibody thereagainst does not substantially cross-react with other epitopes. Suitable tag polypeptides generally have at least six amino acid residues and usually between about 8–50 amino acid residues (preferably between about 9–30 residues).

"Isolated WSX receptor" means WSX receptor that has been purified from a WSX receptor source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

"Biological property" when used in conjunction with either "WSX receptor" or "isolated WSX receptor" means having an effector or antigenic function or activity that is directly or indirectly caused or performed by native sequence WSX receptor (whether in its native or denatured conformation). Effector functions include ligand binding; and enhancement of survival, differentiation and/or proliferation of cells (especially proliferation of cells). However, effector functions do not include possession of an epitope or antigenic site that is capable of cross-reacting with antibodies raised against native sequence WSX receptor.

An "antigenic function" means possession of an epitope or antigenic site that is capable of cross-reacting with antibodies raised against native sequence WSX receptor. The principal antigenic function of a WSX receptor polypeptide is that it binds with an affinity of at least about $10^6$ L/mole to an antibody raised against native sequence WSX receptor. Ordinarily, the polypeptide binds with an affinity of at least about $10^7$ L/mole. The antibodies used to define "antigenic function" are rabbit polyclonal antibodies raised by formulating the WSX receptor in Freund's complete adjuvant, subcutaneously injecting the formulation, and boosting the immune response by intraperitoneal injection of the formulation until the titer of the anti-WSX receptor antibody plateaus.

"Biologically active" when used in conjunction with either "WSX receptor" or "isolated WSX receptor" means a WSX receptor polypeptide that exhibits or shares an effector function of native sequence WSX receptor and that may (but need not) in addition possess an antigenic function. A principal effector function of the WSX receptor is its ability to induce proliferation of CD34+ human umbilical cord blood cells in the colony assay described in Example 8.

"Antigenically active" WSX receptor is defined as a polypeptide that possesses an antigenic function of WSX receptor and that may (but need not) in addition possess an effector function.

"Percent amino acid sequence identity" with respect to the WSX receptor sequence is defined herein as the percentage of amino acid residues in the candidate sequence that are identical with the residues in the WSX receptor sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the candidate WSX receptor sequence shall be construed as affecting sequence identity or homology.

"WSX ligand" is a molecule which binds to and preferably activates native sequence WSX receptor. The ability of a molecule to bind to WSX receptor can be determined by the ability of a putative WSX ligand to bind to WSX receptor immunoadhesin (see Example 2) coated on an assay plate, for example. The thymidine incorporation assay provides a means for screening for WSX ligands which activate the WSX receptor. Exemplary WSX ligands include anti-WSX receptor agonist antibodies and the protein described in Zhang et al. *Nature* 372:425–431 (1994).

A "thymidine incorporation assay" can be used to screen for molecules which activate the WSX receptor. In order to perform this assay, IL-3 dependent Baf3 cells (Palacios et al., *Cell*, 41:727–734 (1985)) are stably transfected with full length native sequence WSX receptor as described in Example 4. The WSX receptor/Baf3 cells so generated are starved of IL-3 for 24 hours in a humidified incubator at 37° C. in 5% $CO_2$ and air. Following IL-3 starvation, the cells are plated out in 96 well culture dishes with, or without, a test sample containing a potential agonist (such test samples are optionally diluted) and cultured for 24 hours in a cell culture incubator. 20 µl of serum free RPMI media containing 1 µCi of $^3H$ thymidine is added to each well for the last 6–8 hours. The cells are then harvested in 96 well filter plates and washed with water. The filters are then counted using a Packard Top Count Microplate Scintillation Counter, for example. Agonists are expected to induce a statistically significant increase (to a P value of 0.05) in $^3H$ uptake, relative to control. Preferred agonists leads to an increase in $^3H$ uptake which is at least two fold of that of the control.

An "isolated" WSX receptor nucleic acid molecule is a nucleic acid molecule that is identified and separated from at least one contaminant nucleic acid molecule with which it is ordinarily associated in the natural source of the WSX receptor nucleic acid. An isolated WSX receptor nucleic acid molecule is other than in the form or setting in which it is found in nature. Isolated WSX receptor nucleic acid molecules therefore are distinguished from the WSX receptor nucleic acid molecule as it exists in natural cells. However, an isolated WSX receptor nucleic acid molecule includes WSX receptor nucleic acid molecules contained in cells that ordinarily express WSX receptor where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256: 495 (1975), or may be made by recombinant DNA methods (see, e.g., U.S. Pat. No. 4,816,567 (Cabilly et al.)). The "monoclonal antibodies" may also be isolated from phage antibody libraries using the techniques described in Clackson et al., Nature, 352: 624–628 (1991) and Marks et al., *J. Mol. Biol.*, 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. USA*, 81:6851–6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522–525 (1986); Reichmann et al., *Nature*, 332:323–329 (1988); and Presta, *Curr. Op. Struct. Biol.*, 2:593–596 (1992). The humanized antibody includes a Primatized™ antibody wherein the antigen-binding region of the antibody is derived from an antibody produced by immunizing macaque monkeys with the antigen of interest.

"Non-immunogenic in a human" means that upon contacting the polypeptide of interest in a physiologically acceptable carrier and in a therapeutically effective amount with the appropriate tissue of a human, no state of sensitivity or resistance to the polypeptide of interest is demonstrable upon the second administration of the polypeptide of interest after an appropriate latent period (e.g., 8 to 14 days).

By "agonist antibody" is meant an antibody which is able to activate native sequence WSX receptor. WSX receptor activation can be determined using the thymidine incorporation assay described above.

A "neutralizing antibody" is one which is able to block or significantly reduce an effector function of native sequence WSX receptor. For example, a neutralizing antibody may inhibit or reduce WSX receptor activation by a WSX ligand as determined in the thymidine incorporation assay.

The phrase "enhancing proliferation of a cell" encompasses the step of increasing the extent of growth and/or reproduction of the cell relative to an untreated cell either in vitro or in vivo. An increase in cell proliferation in cell culture can be detected by counting the number of cells before and after exposure to a molecule of interest. The extent of proliferation can be quantified via microscopic examination of the degree of confluency. Cell proliferation can also be quantified using the thymidine incorporation assay described herein.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g., identifying morphological changes in the cell).

A "CD34+ cell population" is enriched for hematopoietic stem cells. A CD34+ cell population can be obtained from umbilical cord blood or bone marrow, for example. Human umbilical cord blood CD34+ cells can be selected for using immunomagnetic beads sold by Miltenyi (California), following the manufacturer's directions.

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule. Exemplary salvage receptor binding epitope sequences include HQNLSDGK (SEQ ID NO:39); HQNIS-DGK (SEQ ID NO:40); HQSLGTQ (SEQ ID NO:41); VISSHLGQ (SEQ ID NO:42); and PKNSSMISNTP (SEQ ID NO:43).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "solid phase" is meant a non-aqueous matrix to which a reagent of interest (e.g., the WSX receptor or an antibody thereto) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

II. Modes for Carrying Out the Invention

The present invention is based on the discovery of the WSX receptor. The experiments described herein demonstrate that this molecule is a cytokine receptor which appears to play a role in enhancing proliferation and/or differentiation of hematopoietic cells. In particular, this receptor has been found to be present in enriched human stem cell populations, thus indicating that WSX ligands, such as agonist antibodies, may be used to stimulate proliferation of hematopoietic stem cells/progenitor cells. Other uses for this receptor will be apparent from the following discussion.

A description follows as to how WSX receptor may be prepared.

A. Preparation of WSX Receptor

Techniques suitable for the production of WSX receptor are well known in the art and include isolating WSX receptor from an endogenous source of the polypeptide, peptide synthesis (using a peptide synthesizer) and recombinant techniques (or any combination of these techniques). The preferred technique for production of WSX receptor is a recombinant technique to be described below.

Most of the discussion below pertains to recombinant production of WSX receptor by culturing cells transformed with a vector containing WSX receptor nucleic acid and recovering the polypeptide from the cell culture. It is further envisioned that the WSX receptor of this invention may be produced by homologous recombination, as provided for in WO 91/06667, published May 16, 1991.

Briefly, this method involves transforming primary human cells containing a WSX receptor-encoding gene with a construct (i.e., vector) comprising an amplifiable gene (such as dihydrofolate reductase (DHFR) or others discussed below) and at least one flanking region of a length of at least about 150 bp that is homologous with a DNA sequence at the locus of the coding region of the WSX receptor gene to provide amplification of the WSX receptor gene. The amplifiable gene must be at a site that does not interfere with expression of the WSX receptor gene. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing WSX receptor are grown so as to express the gene and produce the protein.

1. Isolation of DNA Encoding WSX Receptor

The DNA encoding WSX receptor may be obtained from any cDNA library prepared from tissue believed to possess the WSX receptor mRNA and to express it at a detectable level. Accordingly, WSX receptor DNA can be conveniently obtained from a cDNA library prepared from mammalian fetal liver. The WSX receptor-encoding gene may also be obtained from a genomic library or by oligonucleotide synthesis.

Libraries are screened with probes (such as antibodies to the WSX receptor or oligonucleotides of about 20–80 bases) designed to identify the gene of interest or the protein encoded by it. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989). An alternative means to isolate the gene encoding WSX receptor is to use PCR methodology as described in section 14 of Sambrook et al., supra.

A preferred method of practicing this invention is to use carefully selected oligonucleotide sequences to screen cDNA libraries from various human tissues, preferably human fetal liver. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Amino acid sequence variants of WSX receptor are prepared by introducing appropriate nucleotide changes into the WSX receptor DNA, or by synthesis of the desired WSX receptor polypeptide. Such variants represent insertions, substitutions, and/or specified deletions of, residues within or at one or both of the ends of the amino acid sequence of a naturally occurring human WSX receptor, such as the WSX receptor variants shown in FIGS. 2A–D. Preferably, these variants represent insertions and/or substitutions within or at one or both ends of the mature sequence, and/or insertions, substitutions and/or specificed deletions within or at one or both of the ends of the signal sequence of the WSX receptor. Any combination of insertion, substitution, and/or specified deletion is made to arrive at the final construct, provided that the final construct possesses the desired biological activity as defined herein. The amino acid changes also may alter post-translational processes of the WSX receptor, such as changing the number or position of glycosylation sites, altering the membrane anchoring characteristics, and/or altering the intracellular location of the WSX receptor by inserting, deleting, or otherwise affecting the leader sequence of the WSX receptor.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis. See also, for example, Table I therein and the discussion surrounding this table for guidance on selecting amino acids to change, add, or delete.

2. Insertion of Nucleic Acid into Replicable Vector

The nucleic acid (e.g., cDNA or genomic DNA) encoding the WSX receptor is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

a. Signal Sequence Component

The WSX receptors of this invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the WSX receptor DNA that is inserted into the vector. The heterologous signal sequence selected preferably is one that is recognized and processed (i.e., cleaved by a signal peptidase) by the host cell. For prokaryotic host cells that do not recognize and process the native WSX receptor signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, α factor leader (including Saccharomyces and Kluyveromyces α-factor leaders, the latter described in U.S. Pat. No. 5,010,182 issued Apr. 23, 1991), or acid phosphatase leader, the *C. albicans* glucoamylase leader (EP 362,179 published Apr. 4, 1990), or the signal described in WO 90/13646 published Nov. 15, 1990. In mammalian cell expression the native signal sequence (e.g., the WSX receptor presequence that normally directs secretion of WSX receptor from human cells in vivo) is satisfactory, although other mammalian signal sequences may be suitable, such as signal sequences from other animal WSX receptors, and signal sequences from secreted polypeptides of the same or related species, as well as viral secretory leaders, for example, the herpes simplex gD signal.

The DNA for such precursor region is ligated in reading frame to DNA encoding the mature WSX receptor.

b. Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2$\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of WSX receptor DNA. However, the recovery of genomic DNA encoding WSX receptor is more complex than that of an exogenously replicated vector because restriction enzyme digestion is required to excise the WSX receptor DNA.

c. Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the WSX receptor nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes WSX receptor. Amplification is the process by which genes in greater demand for the production of a protein critical for growth are reiterated in tandem within the chromosomes of successive generations of recombinant cells. Increased quantities of WSX receptor are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA*, 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding WSX receptor. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding WSX receptor, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of Kluyveromyces yeasts. Bianchi et al., Curr. Genet., 12:185 (1987). More recently, an expression system for large-scale production of recombinant calf chymosin was reported for K. lactis. Van den Berg, Bio/Technology, 8:135 (1990). Stable multicopy expression vectors for secretion of mature recombinant human serum albumin by industrial strains of Kluyveromyces have also been disclosed. Fleer et al., Bio/Technology, 9:968–975 (1991).

d. Promoter Component

Expression and cloning vectors usually contain a promoter that is recognized by the host organism and is operably linked to the WSX receptor nucleic acid. Promoters are untranslated sequences located upstream (5') to the start codon of a structural gene (generally within about 100 to 1000 bp) that control the transcription and translation of particular nucleic acid sequence, such as the WSX receptor nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to WSX receptor-encoding DNA by removing the promoter from the source DNA by restriction enzyme digestion and inserting the isolated promoter sequence into the vector. Both the native WSX receptor promoter sequence and many heterologous promoters may be used to direct amplification and/or expression of the WSX receptor DNA. However, heterologous promoters are preferred, as they generally permit greater transcription and higher yields of WSX receptor as compared to the native WSX receptor promoter.

Promoters suitable for use with prokaryotic hosts include the β-lactamase and lactose promoter systems (Chang et al., *Nature*, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter. deBoer et al., *Proc. Natl. Acad. Sci. USA*, 80:21–25 (1983). However, other known bacterial promoters are suitable. Their nucleotide sequences have been published, thereby enabling a skilled worker operably to ligate them to DNA encoding WSX receptor (Siebenlist et al., *Cell*, 20:269 (1980)) using linkers or adaptors to supply any required restriction sites. Promoters for use in bacterial systems also will contain a Shine-Dalgarno (S.D.) sequence operably linked to the DNA encoding WSX receptor.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

WSX receptor transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the WSX receptor sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan et al., *Science*, 209:1422–1427 (1980); Pavlakis et al., *Proc. Natl. Acad. Sci. USA*, 78:7398–7402 (1981). The immediate early promoter of the human cytomegalovirus is conveniently obtained as a HindIII E restriction fragment. Greenaway et al., *Gene*, 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295:503–508 (1982) on expressing cDNA encoding immune interferon in monkey cells; Reyes et al., *Nature*, 297:598–601 (1982) on expression of human β-interferon cDNA in mouse cells under the control of a thymidine kinase promoter from herpes simplex virus; Canaani et al., *Proc. Natl. Acad. Sci. USA*, 79:5166–5170 (1982) on expression of the human interferon β1 gene in cultured mouse and rabbit cells; and Gorman et al., *Proc. Natl. Acad. Sci. USA*, 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

e. Enhancer Element Component Transcription of a DNA encoding the WSX receptor of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78:993 (1981)) and 3' (Lusky et al., *Mol. Cell Bio.*, 3:1108 (1983)) to the transcription unit, within an intron (Banerji et al., *Cell*, 33:729 (1983)), as well as within the coding sequence itself. Osborne et al., *Mol. Cell Bio.*, 4:1293 (1984). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the WSX receptor-encoding sequence, but is preferably located at a site 5' from the promoter.

f. Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding WSX receptor.

g. Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9:309 (1981) or by the method of Maxam et al., *Methods in Enzymology*, 65:499 (1980).

h. Transient Expression Vectors

Particularly useful in the practice of this invention are expression vectors that provide for the transient expression in mammalian cells of DNA encoding WSX receptor. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of WSX receptor that are biologically active WSX receptor.

i. Suitable Exemplary Vertebrate Cell Vectors

Other methods, vectors, and host cells suitable for adaptation to the synthesis of WSX receptor in recombinant vertebrate cell culture are described in Gething et al., *Nature*, 293:620–625 (1981); Mantei et al., *Nature*, 281:40–46 (1979); EP 117,060; and EP 117,058. A particularly useful plasmid for mammalian cell culture expression of WSX receptor is pRK5 (EP 307,247) or pSVI6 B. WO 91/08291 published Jun. 13, 1991.

3. Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Eschedchia, e.g., *E. coli*, Enterobacter, Erwinia, Klebsiella, Proteus, Salmonella, e.g., *Salmonella typhimurum*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac)169 ompTΔ degP41kan$^r$. Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed. Alternatively still, methods of cloning, e.g., PCR or other nucleic acid polymerase reactions, are suitable.

In addition to prokaryotes, eukaryotic microbes such as filamentous fungi or yeast are suitable cloning or expression hosts for WSX receptor-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach et al., *Nature*, 290:140 (1981); EP 139,383 published May 2, 1985); Kluyveromyces hosts (U.S. Pat. No. 4,943,529; Fleer et al., supra) such as, e.g., *K. lactis* (MW98-8C, CBS683, CBS4574; Louvencourt et al., *J. Bacteriol.*, 737 (1983)), *K. fragilis* (ATCC 12,424), *K. bulgarcus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; yarrowia (EP 402,226); *Pichia pastods* (EP 183,070; Sreekrishna et al., *J. Basic Microbiol.*, 28:265–278 (1988)); Candida; *Trichoderma reesia* (EP 244,234); *Neurospora crassa* (Case et al., *Proc. Natl. Acad. Sci. USA*, 76:5259–5263 (1979)); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans*

(Ballance et al., *Biochem. Biophys. Res. Commun.*, 112:284–289 (1983); Tilbum et al., *Gene*, 26:205–221 (1983); Yelton et al., *Proc. Natl. Acad. Sci. USA*, 81:1470–1474 (1984)) and *A. niger* Kelly et al., *EMBO J.*, 4:475–479 (1985).

Suitable host cells for the expression of glycosylated WSX receptor are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6:47–55 (1988); Miller et al., in *Genetic Engineering*, Setlow et al., eds., Vol. 8 (Plenum Publishing, 1986), pp. 277–279; and Maeda et al., *Nature*, 315:592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the WSX receptor-encoding DNA. During incubation of the plant cell culture with *A. tumefaciens*, the DNA encoding the WSX receptor is transferred to the plant cell host such that it is transfected, and will, under appropriate conditions, express the WSX receptor-encoding DNA. In addition, regulatory and signal sequences compatible with plant cells are available, such as the nopaline synthase promoter and polyadenylation signal sequences. Depicker et al., *J. Mol. Appl. Gen.*, 1:561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

However, interest has been greatest in vertebrate cells, and propagation of vertebrate cells in culture (tissue culture) has become a routine procedure. See, e.g., *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells/-DHFR (CHO, Urlaub et al., *Proc. Natl. Acad. Sci. USA*, 77:4216 (1980)); mouse sertoli cells (TM4, Mather, *Biol. Reprod.*, 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44–68 (1982)); MRC 5 cells; FS4 cells; and a human hepatoma line (Hep G2).

Host cells are transfected and preferably transformed with the above-described expression or cloning vectors for WSX receptor production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterum tumefaciens* is used for transformation of certain plant cells, as described by Shaw et al., *Gene*, 23:315 (1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham et al., *Virology*, 52:456–457 (1978) is preferred. General aspects of mammalian cell host system transformations have been described in U.S. Pat. No. 4,399,216 issued Aug. 16, 1983. Transformations into yeast are typically carried out according to the method of Van Solingen et al., *J. Bact.*, 130:946 (1977) and Hsiao et al., *Proc. Natl. Acad. Sci. USA*, 76:3829 (1979). However, other methods for introducing DNA into cells, such as by nuclear microinjection, electroporation, bacterial protoplast fusion with intact cells, or polycations, e.g., polybrene, polyomithine, etc., may also be used. For various techniques for transforming mammalian cells, see Keown et al., *Methods in Enzymology*, 185:527–537 (1990) and Mansour et al., *Nature*, 336:348–352 (1988).

4. Culturing the Host Cells

Prokaryotic cells used to produce the WSX receptor polypeptide of this invention are cultured in suitable media as described generally in Sambrook et al., supra.

The mammalian host cells used to produce the WSX receptor of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al. *Meth. Enz.*, 58:44 (1979), Bames et al., *Anal. Biochem.*, 102:255 (1980), U.S. Pat. Nos. 4,767,704; 4,657,866; 4,927,762; 4,560,655; or U.S. Pat. No. 5,122,469; WO 90/03430; WO 87/00195; or U.S. Patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77:5201–5205 (1980)), dot blotting (DNA analysis), or in situ hybridization, using an appropriately labeled probe, based on the sequences provided herein. Various labels may be employed, most commonly radioisotopes, particularly $^{32}$p. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescens, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75:734–738 (1980).

Antibodies useful for immunohistochemical staining and/or assay of sample fluids may be either monoclonal or polyclonal, and may be prepared as described herein.

6. Purification of WSX Receptor Polypeptide

WSX receptor (e.g., WSX receptor ECD) preferably is recovered from the culture medium as a secreted polypeptide, although it also may be recovered from host cell lysates. If the WSX receptor is membrane-bound, it can be released from the membrane using a suitable detergent solution (e.g. Triton-X 100)

When WSX receptor.is produced in a recombinant cell other than one of human origin, the WSX receptor is completely free of proteins or polypeptides of human origin. However, it is necessary to purify WSX receptor from recombinant cell proteins or polypeptides to obtain preparations that are substantially homogeneous as to WSX receptor. As a first step, the culture medium or lysate is centrifuged to remove particulate cell debris. WSX receptor thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX G-75; and protein A SEPHAROSE columns to remove contaminants such as IgG.

WSX receptor variants in which residues have been deleted, inserted, or substituted are recovered in the same fashion as native sequence WSX receptor, taking account of any substantial changes in properties occasioned by the variation. Immunoaffinity columns such as a rabbit polyclonal anti-WSX receptor column can be employed to absorb the WSX receptor variant by binding it to at least one remaining immune epitope.

A protease inhibitor such as phenyl methyl sulfonyl fluoride (PMSF) also may be useful to inhibit proteolytic degradation during purification, and antibiotics may be included to prevent the growth of adventitious contaminants.

7. Covalent Modifications of WSX Receptor Polypeptides

Covalent modifications of WSX receptor polypeptides are included within the scope of this invention. Both native sequence WSX receptor and amino acid sequence variants of the WSX receptor may be covalently modified. One type of covalent modification of the WSX receptor is introduced into the molecule by reacting targeted amino acid residues of the WSX receptor with an organic derivatizing agent that is capable of reacting with selected side chains or the N- or C-terminal residues of the WSX receptor.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $pK_a$ of the guanidine functional group. Furthermore, these reagents may react with the groups of lysine as well as with the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking WSX receptor to a water-insoluble support matrix or surface for use in the method for purifying anti-WSX receptor antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidylpropionate), and bifunctional maleimides such as bis-N-maleimido-1,8-octane. Derivatizing agents such as methyl-3-((p-azidophenyl) dithio)propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and U.S. Pat. No. 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79–86 (1983)), acetylation of the N-terminal amine, and amidation of any C-terminal carboxyl group.

Another type of covalent modification of the WSX receptor polypeptide included within the scope of this invention comprises altering the native glycosylation pattern of the polypeptide. By altering is meant deleting one or more carbohydrate moieties found in native WSX receptor, and/or adding one or more glycosylation sites that are not present in the native WSX receptor.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the WSX receptor polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native WSX receptor sequence (for O-linked glycosylation sites). For ease, the WSX receptor amino acid sequence is preferably altered through changes at the DNA level, particularly by mutating the DNA encoding the WSX receptor polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the WSX receptor polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin et al., *CRC Crit. Rev. Biochem.*, 259–306 (1981).

Removal of carbohydrate moieties present on the WSX receptor polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Glycosylation at potential glycosylation sites may be prevented by the use of the compound tunicamycin as described by Duskin et al., *J. Biol. Chem.*, 257:3105 (1982). Tunicamycin blocks the formation of protein-N-glycoside linkages.

Another type of covalent modification of WSX receptor comprises linking the WSX receptor polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337.

Since it is often difficult to predict in advance the characteristics of a variant WSX receptor, it will be appreciated that some screening of the recovered variant will be needed to select the optimal variant. A change in the immunological character of the WSX receptor molecule, such as affinity for a given antibody, is also able to be measured by a competitive-type immunoassay. The variant is assayed for changes in the ability of the protein to induce cell proliferation in the colony assay of Example 8. Other potential modifications of protein or polypeptide properties such as redox or thermal stability, hydrophobicity, susceptibility to proteolytic degradation, or the tendency to aggregate with carriers or into multimers are assayed by methods well known in the art.

8. Epitope-Tagged WSX Receptor

This invention encompasses chimeric polypeptides comprising WSX receptor fused to a heterologous polypeptide. A chimeric WSX receptor is one type of WSX receptor variant as defined herein. In one preferred embodiment, the chimeric polypeptide comprises a fusion of the WSX receptor with a tag polypeptide which provides an epitope to which an anti-tag antibody can selectively bind. The epitope tag is generally provided at the amino- or carboxyl-terminus of the WSX receptor. Such epitope-tagged forms of the WSX receptor are desirable as the presence thereof can be detected using a labeled antibody against the tag polypeptide. Also, provision of the epitope tag enables the WSX receptor to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., *Mol. Cell. Biol.*, 8:2159–2165 (1988)); the c-myc tag and the 8F9, 3C7, 6E10, G4, B7 and 9E10 antibodies thereto (Evan et al., *Molecular and Cellular Biology*, 5:3610–3616 (1985)); and the Herpes Simplex virus glycoprotein D (gD) tag and its antibody. Paborsky et al., *Protein Engineering*, 3(6): 547–553 (1990). Other tag polypeptides have been disclosed. Examples include the Flag-peptide (Hopp et al., *BioTechnology*, 6:1204–1210 (1988)); the KT3 epitope peptide (Martin et al., *Science*, 255:192–194 (1992)); an α-tubulin epitope peptide (Skinner et al., *J. Biol. Chem.*, 266:15163–15166 (1991)); and the T7 gene 10 protein peptide tag. Lutz-Freyermuth et al., *Proc. Natl. Acad. Sci. USA*, 87:6393–6397 (1990). Once the tag polypeptide has been selected, an antibody thereto can be generated using the techniques disclosed herein.

The general methods suitable for the construction and production of epitope-tagged WSX receptor are the same as those disclosed hereinabove. WSX receptor-tag polypeptide fusions are most conveniently constructed by fusing the cDNA sequence encoding the WSX receptor portion in-frame to the tag polypeptide DNA sequence and expressing the resultant DNA fusion construct in appropriate host cells. Ordinarily, when preparing the WSX receptor-tag polypeptide chimeras of the present invention, nucleic acid encoding the WSX receptor will be fused at its 3' end to nucleic acid encoding the N-terminus of the tag polypeptide, however 5' fusions are also possible.

Epitope-tagged WSX receptor can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-tagged WSX receptor can be eluted from the affinity column by varying the buffer pH or ionic strength or adding chaotropic agents, for example.

9. WSX Receptor Immunoadhesins

Chimeras constructed from a receptor sequence linked to an appropriate immunoglobulin constant domain sequence (immunoadhesins) are known in the art. Immunoadhesins reported in the literature include fusions of the T cell receptor* (Gascoigne et al., *Proc. Natl. Acad. Sci. USA*, 84: 2936–2940 (1987)); CD4* (Capon et al., *Nature* 337: 525–531 (1989); Traunecker et al., *Nature*, 339: 68–70 (1989); Zettmeissl et al., *DNA Cell Biol. USA*, 9: 347–353 (1990); Byrn et al., *Nature*, 344: 667–670 (1990)); L-selectin (homing receptor) ((Watson et al., *J. Cell. Biol.*, 110:2221–2229 (1990); Watson et al., *Nature*, 349: 164–167 (1991)); CD44* (Aruffo et al., *Cell*, 61: 1303–1313 (1990)); CD28* and B7* (Linsley et al., *J. Exp. Med.*, 173: 721–730 (1991)); CTLA-4* (Lisley et al., *J. Exp. Med.* 174: 561–569 (1991)); CD22* (Stamenkovic et al., *Cell*, 66:1133–1144 (1991)); TNF receptor (Ashkenazi et al., *Proc. Natl. Acad. Sci. USA*, 88: 10535–10539 (1991); Lesslauer et al., *Eur. J. Immunol.*, 27: 2883–2886 (1991); Peppel et al., *J. Exp. Med.*, 174:1483–1489 (1991)); NP receptors (Bennett et al., *J. Biol. Chem.* 266:23060–23067 (1991)); and IgE receptor α* (Ridgway et al., *J. Cell. Biol.*, 115:abstr. 1448 (1991)), where the asterisk (*) indicates that the receptor is member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the WSX receptor-immunoglobulin chimeras of the present invention, nucleic acid encoding the extracellular domain of the WSX receptor will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the WSX receptor-immunoglobulin chimeras.

In some embodiments, the WSX receptor-immunoglobulin chimeras are assembled as monomers, or hetero- or homo-multimers, and particularly as dimers or tetramers, essentially as illustrated in WO 91/08298.

In a preferred embodiment, the WSX receptor extracellular domain sequence is fused to the N-terminus of the C-terminal portion of an antibody (in particular the Fc domain), containing the effector functions of an immunoglobulin, e.g. immunoglobulin $G_1$ (IgG1). It is possible to fuse the entire heavy chain constant region to the WSX receptor extracellular domain sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the WSX receptor amino acid sequence is fused to the hinge region, CH2 and CH3, or the CH1, hinge, CH2 and CH3 domains of an IgG1, IgG2, or IgG3 heavy chain. The precise site at which the fusion is made is not critical, and the optimal site can be determined by routine experimentation.

In some embodiments, the WSX receptor-immunoglobulin chimeras are assembled as multimers, and particularly as homo-dimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled WSX receptor-immunoglobulin chimeras within the scope herein are schematically diagrammed below:

(a) $AC_L$-$AC_L$;

(b) $AC_H$-($AC_H$, $AC_L$-$AC_H$, $AC_L$-$V_H C_H$, or $V_L C_L$-$AC_H$);

(c) $AC_L$-$AC_H$-($AC_L$-$AC_H$, $AC_L$-$V_H C_H$, $V_L C_L$-$AC_H$, or $V_L C_L$-$V_H C_H$);
(d) $AC_L$-$V_H C_H$-($AC_H$, or $AC_L$-$V_H C_H$, or $V_L C_L$-$AC_H$);
(e) $V_L C_L$-$AC_H$-($AC_L$-$V_H C_H$, or $V_L C_L$-$AC_H$); and
(f) $(A$-$Y)_n$-$(V_L C_L$-$V_H C_H)_2$, wherein each A represents identical or different WSX receptor amino acid sequences;

$V_L$ is an immunoglobulin light chain variable domain;

$V_H$ is an immunoglobulin heavy chain variable domain;

$C_L$ is an immunoglobulin light chain constant domain;

$C_H$ is an immunoglobulin heavy chain constant domain;

n is an integer greater than 1;

Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the WSX receptor extracellular domain sequence can be inserted between immunoglobulin heavy chain and light chain sequences such that an immunoglobulin comprising a chimeric heavy chain is obtained. In this embodiment, the WSX receptor sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al., *Mol. Immunol.*, 28:1027–1037 (1991).

Although the presence of an immunoglobulin light chain is not required in the immunoadhesins of the present invention, an immunoglobulin light chain might be present either covalently associated to an WSX receptor-immunoglobulin heavy chain fusion polypeptide, or directly fused to the WSX receptor extracellular domain. In the former case, DNA encoding an immunoglobulin light chain is typically coexpressed with the DNA encoding the WSX receptor-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For WSX receptor immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1m1, is non-immunogenic. In contrast, there are 12 serologically-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the WSX receptor part of the molecule is placed directly upstream of the codons for the sequence DKTH-TCPPCP (SEQ ID NO:44) of the IgG1 hinge region.

The general methods suitable for the construction and expression of immunoadhesins are the same as those disclosed hereinabove with regard to WSX receptor. WSX receptor immunoadhesins are most conveniently constructed by fusing the cDNA sequence encoding the WSX receptor portion in-frame to an Ig cDNA sequence. However, fusion to genomic Ig fragments can also be used (see, e.g., Gascoigne et al., *Proc. Natl. Acad. Sci. USA*, 84:2936–2940 (1987); Aruffo et al., *Cell*, 61:1303–1313 (1990); Stamenkovic et al., *Cell*, 66:1133–1144 (1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the WSX receptor and Ig parts of the immunoadhesin are inserted in tandem into a plasmid vector that directs efficient expression in the chosen host cells. For expression in mammalian cells, pRK5-based vectors (Schall et al., *Cell*, 61:361–370 (1990)) and CDM8-based vectors (Seed, *Nature*, 329:840 (1989)) can be used. The exact junction can be created by removing the extra sequences between the designed junction codons using oligonucleotide-directed deletional mutagenesis (Zoller et al., *Nucleic Acids Res.*, 10:6487 (1982); Capon et al., *Nature*, 337:525–531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of WSX receptor immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell*, 61:1303–1313 (1990); Zettmeissl et al., *DNA Cell Biol. US*, 9:347–353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra, Martin et al., *J. Virol.*, 67:3561–3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains (Lindmark et al., *J. Immunol. Meth.*, 62:1–13 (1983)). Protein G is recommended for all mouse isotypes and for human γ3 (Guss et al., *EMBO J.*, 5:1567–1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography (Hutchens et al., *Anal. Biochem.*, 159:217–226 (1986)) and immobilized metal chelate chromatography (Al-Mashikhi et al., *J. Dairy Sci.*, 71:1756–1763 (1988)). In contrast to antibodies, however, their behavior on ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a WSX receptor extracellular domain and a domain, such as the extracellular domain, of another cytokine receptor subunit. Exemplary cytokine receptors from which such bispecific immunoadhesin molecules can be made include TPO (or mpl ligand), EPO, G-CSF, IL-4, IL-7, GH, PRL, IL-3, GM-CSF, IL-5, IL-6, LIF, OSM, CNTF and IL-2 receptors. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

B. Therapeutic Uses for the WSX Receptor

The WSX receptor and WSX receptor gene are believed to find therapeutic use for administration to a mammal in the treatment of diseases characterized by a decrease in hematopoietic cells. Examples of these diseases include: anemia (including macrocytic and aplastic anemia); thrombocytopenia; hypoplasia; disseminated intravascular coagulation (DIC); myelodysplasia; immune (autoimmune) thrombocytopenic purpura (ITP); and HIV induced ITP. Additionally, these WSX receptor molecules may be useful in treating myeloproliferative thrombocytotic diseases as well as thrombocytosis from inflammatory conditions and in iron deficiency. WSX receptor polypeptide and WSX receptor gene which lead to an increase in hematopoietic cell proliferation may also be used to enhance repopulation of mature blood cell lineages in cells having undergone chemo- or radiation therapy or bone marrow transplantation therapy. Generally, the WSX receptor molecules are expected to lead to an enhancement of the proliferation and/or differentiation (but especially proliferation) of primitive hematopoietic cells.

Other potential therapeutic applications for WSX receptor and WSX receptor gene include the treatment of obesity and diabetes and for promoting kidney, liver and lung growth and/or repair (e.g. in renal failure).

Administration of WSX receptor to a mammal having depressed levels of endogenous WSX receptor or a defective WSX receptor gene is contemplated, preferably in the situation where such depressed levels lead to a pathological disorder, or where there is lack of activation of the WSX receptor. In these embodiments where the full length WSX receptor is to be administered to the patient, it is contemplated that the gene encoding the receptor may be administered to the patient via gene therapy technology.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA*, 83:4143–4146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology*, 11:205–210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.*, 262:4429–4432 (1987); and Wagner et al., *Proc. Natl. Acad. Sci. USA*, 87:3410–3414 (1990). For review of the currently known gene marking and gene therapy protocols see Anderson et al., *Science*, 256:808–813 (1992).

The invention also provides antagonists of WSX receptor activation (e.g. WSX receptor ECD, WSX receptor immunoadhesins and WSX receptor antisense nucleic acid; neutralizing antibodies and uses thereof are discussed in section E below). Administration of WSX receptor antagonist to a mammal having increased or excessive levels of endogenous WSX receptor activation is contemplated, preferably in the situation where such levels of WSX receptor activation lead to a pathological disorder.

In one embodiment, WSX receptor antagonist molecules may be used to bind endogenous ligand in the body, thereby causing desensitized WSX receptors to become responsive to WSX ligand, especially when the levels of WSX ligand in the serum exceed normal physiological levels. Also, it may be beneficial to bind endogenous WSX ligand which is activating undesired cellular responses (such as proliferation of tumor cells). Potential therapeutic applications for WSX antagonists include for example, treatment of metabolic disorders (e.g., anorexia and steroid-induced truncalobesity), stem cell tumors and other tumors which express WSX receptor.

Pharmaceutical compositions of the WSX receptor ECD may further include a WSX ligand. Such dual compositions may be beneficial where it is therapeutically useful to prolong half-life of WSX ligand, and/or activate endogenous WSX receptor directly as a heterotrimeric complex.

Therapeutic formulations of WSX receptor are prepared for storage by mixing WSX receptor having the desired degree of purity with optional physiologically acceptable carriers, excipients, or stabilizers (*Remington's Pharmaceutical Sciences*, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics or polyethylene glycol (PEG).

The WSX receptor also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences*, supra.

WSX receptor to be used for in vivo administration must be sterile. This is readily accomplished by filtration through sterile filtration membranes, prior to or following lyophilization and reconstitution. WSX receptor ordinarily will be stored in lyophilized form or in solution.

Therapeutic WSX receptor compositions generally are placed into a container having a sterile access port, for example, an intravenous solution bag or vial having a stopper pierceable by a hypodermic injection needle.

The route of WSX receptor administration is in accord with known methods, e.g., those routes set forth above for specific indications, as well as the general routes of injection or infusion by intravenous, intraperitoneal, intracerebral, intramuscular, intraocular, intraarterial, or intralesional means, or sustained release systems as noted below. WSX receptor is administered continuously by infusion or by bolus injection. Generally, where the disorder permits, one should formulate and dose the WSX receptor for site-specific delivery.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al.,*J. Biomed. Mater. Res.*, 15:167–277 (1981) and Langer, *Chem. Tech.*, 12:98–105 (1982) or poly (vinylalcohol)), polylactides (U.S. Pat. No. 3,773,919, EP 58,481), copolymers of L-glutamic acid and γ ethyl-L-glutamate (Sidman et al., *Biopolymers*, 22:547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D(–)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release WSX receptor compositions also include liposomally entrapped WSX receptor. Liposomes containing WSX receptor are prepared by methods known per se: DE 3,218,121; Epstein et al., *Proc. Natl. Acad. Sci. USA*, 82:3688–3692 (1985); Hwang et al., *Proc. Natl. Acad. Sci. USA*, 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal WSX receptor therapy.

When applied topically, the WSX receptor is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the WSX receptor formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the WSX receptor held within it.

Preferably the polysaccharide is an etherified cellulose derivative, more preferably one that is well defined, purified, and listed in U.S. Patent, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400–600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the WSX receptor is present in an amount of about 300–1000 mg per ml of gel.

An effective amount of WSX receptor to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the WSX receptor until a dosage is reached that achieves the desired effect. A typical daily dosage for systemic treatment might range from about 1 µg/kg to up to 10 mg/kg or more, depending on the factors mentioned above. As an alternative general proposition, the WSX receptor is formulated and delivered to the target site or tissue at a dosage capable of establishing in the tissue a WSX receptor level greater than about 0.1 ng/cc up to a maximum dose that is efficacious but not unduly toxic. This intra-tissue concentration should be maintained if possible by continuous infusion, sustained release, topical application, or injection at empirically determined frequencies. The progress of this therapy is easily monitored by conventional assays.

C. Non-Therapeutic Uses for the WSX Receptor

WSX receptor nucleic acid is useful for the preparation of WSX receptor polypeptide by recombinant techniques exemplified herein which can then be used for production of anti-WSX receptor antibodies having various utilities described below.

The WSX receptor (polypeptide or nucleic acid) can be used to induce proliferation and/or differentiation of cells in vitro. In particular, it is contemplated that this molecule may be used to induce proliferation of stem cellprogenitor cell populations (e.g. CD34+ cell populations obtained as described in Example 8 below). These cells which are to be grown ex vivo may simultaneously be exposed to other known growth factors or cytokines, such as those described herein. This results in proliferation and/or differentiation of the cells having the WSX receptor.

In yet another aspect of the invention, the WSX receptor may be used for affinity purification of WSX ligand. Briefly, this technique involves: (a) contacting a source of WSX ligand with an immobilized WSX receptor under conditions whereby the WSX ligand to be purified is selectively adsorbed onto the immobilized receptor; (b) washing the immobilized WSX receptor and its support to remove non-adsorbed material; and (c) eluting the WSX ligand molecules from the immobilized WSX receptor to which they are adsorbed with an elution buffer. In a particularly preferred embodiment of affinity purification, WSX receptor is covalently attaching to an inert and porous matrix (e.g., agarose reacted with cyanogen bromide). Especially preferred is a WSX receptor immunoadhesin immobilized on a protein A column. A solution containing WSX ligand is then passed through the chromatographic material. The WSX ligand adsorbs to the column and is subsequently released by changing the elution conditions (e.g. by changing pH or ionic strength).

The WSX receptor may be used for competitive screening of potential agonists or antagonists for binding to the WSX receptor. Such agonists or antagonists may constitute potential therapeutics for treating conditions characterized by insufficient or excessive WSX receptor activation, respectively.

The preferred technique for identifying molecules which bind to the WSX receptor utilizes a chimeric receptor (e.g., epitope tagged WSX receptor or WSX receptor immunoadhesin) attached to a solid phase, such as the well of an assay plate. Binding of molecules which are optionally labelled (e.g., radiolabelled) to the immobilized receptor can be evaluated.

To identify WSX receptor agonists or antagonists, the thymidine incorporation assay can be used. For screening for antagonists, the WSX receptor can be exposed to a WSX ligand followed by the putative antagonist, or the WSX ligand and antagonist can be added to the WSX receptor simultaneously, and the ability of the antagonist to block receptor activation can be evaluated.

The WSX receptor polypeptides are also useful as molecular weight markers. To use a WSX receptor polypeptide as a molecular weight marker, gel filtration chromatography or SDS-PAGE, for example, will be used to separate protein(s) for which it is desired to determine their molecular weight(s) in substantially the normal way. The WSX receptor and other molecular weight markers will be used as standards to provide a range of molecular weights. For example, phosphorylase b (mw=97,400), bovine serum albumin (mw=68,000), ovalbumin (mw=46,000), WSX receptor (mw=44,800), trypsin inhibitor (mw=20,100), and lysozyme (mw=14,400) can be used as mw markers. The other molecular weight markers mentioned here can be purchased commercially from Amersham Corporation, Arlington Heights, Ill. The molecular weight markers are generally labeled to facilitate detection thereof. For example, the markers may be biotinylated and following separation can be incubated with streptavidin-horseradish peroxidase so that the various markers can be detected by light detection.

The purified WSX receptor, and the nucleic acid encoding it, may also be sold as reagents for mechanism studies of WSX receptor and its ligands, to study the role of the WSX receptor and WSX ligand in normal growth and development, as well as abnormal growth and development, e.g., in malignancies.

WSX receptor variants are useful as standards or controls in assays for the WSX receptor for example ELISA, RIA, or RRA, provided that they are recognized by the analytical system employed, e.g., an anti-WSX receptor antibody.

D. WSX Receptor Antibody Preparation

1. Polyclonal Antibodies

Polyclonal antibodies are generally raised in animals by multiple subcutaneous (sc) or intraperitoneal (ip) injections of the relevant antigen and an adjuvant. In that the preferred epitope is in the ECD of the WSX receptor, it is desirable to use WSX receptor ECD or a molecule comprising the ECD (e.g., WSX receptor immunoadhesin) as the antigen for generation of polyclonal and monoclonal antibodies. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

2. Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybriddma method first described by Kohler et al., *Nature*, 256:495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzymelinked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993) and Pluckthun, *Immunol. Revs.*, 130:151–188 (1992).

In a further embodiment, antibodies or antibody fragments can be isolated from antibody phage libraries generated using the techniques described in McCafferty et a., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Mark et al., *Bio/Technology*, 10:779–783 (1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (Cabilly et al., supra; Morrison, et al., *Proc. Nat. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Humanized and Human Antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggermann et al., *Year in Immuno.*, 7:33 (1993). Human antibodies can also be produced in phage-display libraries (Hoogenboom et al., *J. Mol. Biol.*, 227:381 (1991); Marks et al., *J. Mol. Biol.*, 222:581 (1991)).

4. Bispecific Antibodies

Bispecific antibodies (BsAbs) are antibodies that have binding specificities for at least two different antigens. BsAbs can be used as tumor targeting or imaging agents and can be used to target enzymes or toxins to a cell possessing the WSX receptor. Such antibodies can be derived from full length antibodies or antibody fragments (e.g. F(ab')$_2$ bispecific antibodies). In accordance with the present invention, the BsAb may possess one arm which binds the WSX receptor and another arm which binds to a cytokine or another cytokine receptor (or a subunit thereof) such as the receptors for TPO, EPO, G-CSF, IL-4, IL-7, GH, PRL; the α or β subunits of the IL-3, GM-CSF, IL-5, IL-6, LIF, OSM and CNTF receptors; or the α, β or γ subunits of the IL-2 receptor complex. For example, the BsAb may bind both WSX receptor and gp130.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., *EMBO J.*, 10:3655–3659 (1991).

According to a different and more preferred approach, antibody variable domains with the desired binding specificities (antibodyantigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. According to these techniques, Fab'-SH fragments can be recovered from *E. coli*, which can be chemically coupled to form bivalent antibodies. Shalaby et al., *J. Exp. Med.*, 175:217–225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodrigues et al., *Int. J. Cancers*, (Suppl.) 7:45–50 (1992).

Various techniques for making and isolating bivalent antibody fragments directly from recombinant cell culture have also been described. For example, bivalent heterodimers have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. USA*, 90:6444–6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites, Another strategy for making BsAb fragments by the use of single-chain Fv (sFv) dimers has also been reported. See. Gruber et al., *J. Immunol*, 152:5368 (1994).

E. Therapeutic Uses for WSX Receptor Antibodies

The agonist WSX receptor antibodies of the present invention can be used to enhance repopulation of mature blood cell lineages in cells having undergone chemo- or radiation therapy or bone marrow transplantation therapy. Generally, the antibodies will act via an enhancement of the proliferation and/or differentiation (but especially proliferation) of primitive hematopoietic cells. The agonist antibodies may similarly be useful for treating diseases characterized by a decrease in blood cells. Examples of these diseases include: anemia (including macrocytic and aplastic anemia); thrombocytopenia; hypoplasia; immune (autoimmune) thrombocytopenic purpura (ITP); and HIV induced ITP. Also, the agonist antibodies may be used to treat a patient having suffered a hemorrhage. Agonist antibodies may also be used to treat metabolic disorders such as obesity and diabetes mellitus, or to promote kidney, liver or lung growth and/or repair (e.g., in renal failure).

Potential therapeutic applications for WSX receptor neutralizing antibodies include the treatment of metabolic disorders (such as cachexia, anorexia and bulimia), stem cell tumors and other tumors at sites of WSX receptor expression, especially those tumors characterized by overexpression of WSX receptor.

For therapeutic applications, the WSX receptor antibodies of the invention are administered to a mammal, preferably a human, in a physiologically acceptable dosage form, including those that may be administered to a human intravenously as a bolus or by continuous infusion over a period of time, by intramuscular, intraperitoneal, intra-cerobrospinal, subcutaneous, intra-articular, intrasynovial, intrathecal, oral, topical, or inhalation routes. The WSX receptor antibodies also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of WSX receptor antibodies include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nanocapsules, liposomes, plasters, inhalation forms, nose sprays, sublingual tablets, and sustained-release preparations. The WSX receptor antibody will typically be formulated in such vehicles at a concentration of about 0.1 mg/ml to 100 mg/ml.

Suitable examples of sustained-release preparations include semipermeable matrices of solid hydrophobic polymers containing the WSX receptor antibody, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and γ ethyl-L-glutamate (Sidman et al., supra), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated WSX receptor antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release WSX receptor antibody compositions also include liposomally entrapped antibodies. Liposomes containing the WSX receptor antibodies are prepared by methods known in the art, such as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Ordinarily, the liposomes are the small (about 200–800 Angstroms) unilamelar type in which the lipid content is greater than about 30 mol. % cholesterol, the selected proportion being adjusted for the optimal WSX receptor antibody therapy. Liposomes with enhanced circulation time are disclosed in U.S. Pat. No. 5,013,556.

For the prevention or treatment of disease, the appropriate dosage of WSX receptor antibody will depend on the type of disease to be treated, as defined above, the severity and course of the disease, whether the antibodies are administered for preventive or therapeutic purposes, previous therapy, the patient's clinical history and response to the WSX receptor antibody, and the discretion of the attending physician. The WSX receptor antibody is suitably administered to the patient at one time or over a series of treatments.

Depending on the type and severity of the disease, about 1 µg/kg to 15 mg/kg of WSX receptor antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

F. Non-Therapeutic Uses for WSX Receptor Antibodies

WSX receptor antibodies may be used for detection of and/or enrichment of hematopoietic stem cell/progenitor cell populations in a similar manner to that in which CD34 antibodies are presently used. For stem cell enrichment, the WSX receptor antibodies may be utilized in the techniques known in the art such as immune panning, flow cytometry or immunomagnetic beads.

The WSX receptor antibodies of the invention are also useful as affinity purification agents. In this process, the antibodies against WSX receptor are immobilized on a suitable support, such a Sephadex resin or filter paper, using methods well known in the art. The immobilized antibody then is contacted with a sample containing the WSX receptor to be purified, and thereafter the support is washed with a suitable solvent that will remove substantially all the material in the sample except the WSX receptor, which is bound to the immobilized antibody. Finally, the support is washed with another suitable solvent, such as glycine buffer, pH 5.0, that will release the WSX receptor from the antibody.

WSX receptor antibodies may also be useful in diagnostic assays for WSX receptor, e.g., detecting its expression in specific cells, tissues, or serum. For diagnostic applications, antibodies typically will be labeled with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^{3}H$; or an enzyme, such as alkaline phosphatase, beta-galactosidase, or horseradish peroxidase.

Any method known in the art for separately conjugating the polypeptide variant to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

Competitive binding assays rely on the ability of a labeled standard to compete with the test sample analyte for binding with a limited amount of antibody. The amount of WSX receptor in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

III. Experimental

Below are examples of specific embodiments for carrying out the present invention. The examples are offered for illustrative purposes only, and are not intended to limit the scope of the present invention in any way.

The disclosures of all publications, patents and patent applications cited herein, whether supra or infra, are hereby incorporated by reference in their entirety.

EXAMPLE 1

Cloning of Human WSX Receptor

An oligonucleotide probe designated WSX.6 #1 was synthesized based upon the T73849 EST sequence. The WSX.6 #1 probe was a 51mer having the following sequence: 5' GTCAGTCTCCCAGTTCCAGACTTGTGT-GCAGTCTATGCTGTTCAGGTGCGC-3' (SEQ ID NO:45).

The radiolabeled WSX.6 #1 probe was used to probe $1.2 \times 10^6$ clones from a random and oligo dT primed λgt10 fetal liver library (Clontech, Palo Alto, Calif.). Following hybridization at 42° C. overnight, the filters were washed at 50° C. in 0.5×SSC and 0.1% $NaDodSO_4$ (SDS). From the initial screen, 10 clones were selected and upon subsequent screening 5 individual plaque pure clones were isolated. Of these 5 individual clones, four clones designated 1, 5, 6 and 9 were subcloned into pBSSK⁻ (Stratagene) following EcoRI digestion. Sequence analysis revealed clone 5 and clone 9 contained the putative initiation methionine and signal peptide. Clone 6 (designated 6.4) contained the most 3' end sequence and subsequently was used for further screening.

To obtain the full length gene, clone 6.4 (fragment Nsi-Hind III) was radiolabeled and used to screen $1.2 \times 10^6$ clones from a λ.gt 10 library constructed from a hepatoma Hep3B cell line. This screen resulted in 24 positive clones. Following PCR analysis of the clones using λ.gt10 primers (F and R), the four longest clones 12.1, 13.2, 22.3, and 24.3 were isolated. These clones were subcloned into pBSSK⁻ using the EcoRI site, and following examination by restriction enzyme digest, clones 12.1 and 13.2 were submitted for sequencing. DNA sequencing was performed with the Taq dye deoxynucleotide terminator cycle sequencing kit on an automated Applied Biosystems DNA sequencer.

The assembled contiguous sequence from all the isolated clones encoded a consensus amino terminus for the newly identified polypeptide designated the WSX receptor. However, sequence analysis revealed that at least three naturally occurring variants of the WSX receptor exist which have different cytoplasmic regions. These variants appear to be differentially spliced at the lysine residue at position 891. Clone 6.4 stops 5 amino acids after Lys 891. Clone 12.1 is different from 13.2 and 6.4 following Lys 891 and encodes a putative box 2 region which is distinct from that encoded by clone 13.2. Clone 13.2 contains a potential box 1 region and following Lys 891 encodes putative box 2 and box 3 motifs. See, Baumann et al., *Mol. Cell. Biol.*, 14(1): 138–146 (1994).

The full length WSX gene based on the clone 13.2 cytoplasmic region putatively encodes an 1165 amino acid transmembrane protein. The 841 amino acid extracellular domain (ECD) contains two WSXWS domains. The ECD is followed by a 24 amino acid transmembrane domain and a 300 amino acid cytoplasmic region.

EXAMPLE 2

WSX Receptor Immunoadhesin

Using polymerase chain amplification, a WSX receptor immunoadhesin was created by engineering an in-frame fusion of the WSX receptor gene extracellular domain (WSX.ECD) with human CH2CH3(Fc)IgG (Bennett et al., *J. Biol. Chem.* 266(34):23060–23067 (1991)) at the C terminus of the ECD and cloned into pBSSK⁻ (Stratagene). For expression, the WSX-Fc was excised with ClaI and BstEII and ligated into the pRK5.HuIF.grbhIgG Genenase I vector (Beck et al., 31(17):1335–1344 (1994)), to create the plasmid pRK5.WSX-IgG Genenase I. This plasmid was transiently transfected into 293 cells using standard calcium phosphate transfection techniques. The transfected cells were cultured at 37° C. in 5% $CO_2$ in DMEM F12 50:50 supplemented with 10% FBS, 100 mM HEPES (pH 7.2) and 1 mM glutamine. The WSX receptor immunoadhesin was purified using a ProSepA™ protein A column.

EXAMPLE 3

Antibody Production

In order to raise antibodies against the WSX receptor, the WSX receptor immunoadhesin of Example 2 was used to inoculate rabbits to raise polyclonal antibodies and mice to raise monoclonal antibodies using conventional technology.

EXAMPLE 4

Generation of a Cell Line Expressing WSX Receptor

The nucleic acid encoding full length WSX receptor variant 13.2 was inserted in the pRKtkNeo plasmid (Holmes et al., Science, 253:1278–1280 (1991)). 100 μgs of the pRKtkNeo.WSX plasmid thus generated was linearized, ethanol precipitated and resuspended in 100 μL of RPMI 1640. 7×10⁶ Baf3 cells (5×10⁵/ml) were suspended in 900 μL of RPMI and added to the linearized plasmid. Following electroporation at 325V, 1180 μF using a BRL electroporation apparatus, the cells were plated into 15 mls of RPMI 1640 containing 5% WEHI3B conditioned media and 15% serum. 48 hours later cells were selected in 2 mg/ml G418.

To obtain the Baf3/WSX cell line expressing WSX receptor variant 13.2, the G418 selected clones were analyzed by FACS using the rabbit polyclonal antisera raised against the WSX-Fc chimeric protein as described above. The highest expressing clone (designated E6) was sorted by FACS to maintain a population with a high level of WSX receptor expression.

EXAMPLE 5

Role of WSX Receptor in Cellular Proliferation

The proliferative potential of the WSX receptor was tested by constructing a human growth hormone receptor-WSX receptor (GH-WSX) fusion encoding for a chimeric protein consisting of the GH receptor extracellular and transmembrane domains and the WSX receptor variant 13.2 intracellular domain. This chimeric gene fusion was transfected into the IL-3 dependent cell line Baf3. The ability of the GH-WSX transfected Baf3 cells to respond to exogenous growth hormone (GH) was tested in a thymidine incorporation assay. As can be seen in FIG. 6, the GH-WSX receptor chimera was capable of increasing thymidine uptake in the transfected Baf3 cells, thus indicating the proliferative potential of the WSX receptor.

Materials and Methods

The GH-WSX chimera was constructed by first using PCR to generate the extracellular and transmembrane domain of the human GH receptor. The 3' end primer used for this PCR contained 20 nucleotides at the 5' end of the primer corresponding to the first 20 nucleotides of the WSX cytoplasmic domain. The 3' end of the chimera was generated using PCR where the 5' end primer contained the last 19 nucleotides of the human GH receptor transmembrane domain. To generate the full length chimera, the 5' end of the human GH receptor product was combined with the 3' end WSX receptor cytoplasmic PCR product and subsequently amplified to create a fusion of the two products.

This chimeric fusion was digested with ClaI and XbaI and ligated to pRKtkNeo (Holmes et al., Science, 253:1278–1280 (1991)) to create the chimeric expression vector. The IL-3 dependent cell line Baf3 was then electroporated with this hGH/WSX chimeric expression vector.

Briefly, 100 μg of the pRKtkNeo/GH.WSX plasmid was linearized, ethanol precipitated and resuspended in 100 μL of RPMI 1640. 7×10⁶ Baf3 cells (5×10⁵/ml) were suspended in 900 μL of RPMI and added to the linearized plasmid. Following electroporation at 325V, 1180 μF using a BRL electroporation apparatus, the cells were plated into 15 mls of RPMI 1640 containing 5% wehi conditioned media and 15% serum. 48 hours later, cells were selected in 2 mg/ml G418.

To obtain the Baf3/GH.WSX cell lines, the G418 selected cells were FACS sorted using an anti-human GH Mab (3B7) at 1 μg/ml. The top 10% expressing cells were selected and expanded.

EXAMPLE 6

Expression Analysis of the WSX Receptor

The expression profile of the WSX receptor was initially examined by Northern analysis. Northern blots of human fetal or adult tissue mRNA were obtained from Clontech (Palo Alto, Calif.). A transcript of approximately 6 kb was detected in human fetal lung, liver and kidney. In the adult, low level expression was detected in a variety of tissues including liver, placenta, lung skeletal muscle, kidney, ovary, prostate and small intestine.

PCR analysis of human cord blood identified transcripts in CD34⁺ subfraction. The CD34⁻ subfraction appeared negative by this same PCR analysis.

EXAMPLE 7

Cloning of Murine WSX Receptor

The human WSX receptor was used as a probe to isolate murine WSX receptor. The pRKtkNeo.WSX plasmid of Example 4 was digested using Ssp1. This Ssp1 fragment (1624 bps) was isolated, and radiolabelled, and used to screen a murine liver λgt10 library (Clontech). This resulted in 4 positive clones which were isolated and sequenced after sub-cloning into pBSSK⁻ via EcoRI digestion. The resultant clones, designated 1, 2, 3, 4 showed homology to the extracellular domain of the human WSX receptor; the contiguous sequences resulting from these clones extended from the initiation methionine to tryptophan at position 783. The overall similarity of human WSX receptor and murine WSX receptor is 73% over this region of the respective extracellular domains (see FIGS. 4A–D).

EXAMPLE 8

The Role of WSX Receptor in Hematopoietic Cell Proliferation

The presence of the WSX receptor in the enriched human stem cell population CD34+ from cord blood is indicative of a potential role for this receptor in stem cell/progenitor cell proliferation.

The proliferation of CD34+ human blood cells in methylcellulose media (Stem Cell Technologies) was determined in the presence or absence of WSX receptor antisense oligonucleotides. These experiments were also repeated in the murine hematopoietic system using AA4⁺ Sca⁺ Kit⁺ stem cells from the murine fetal liver. In both instances, the antisense oligonucleotides statistically significantly inhibited colony formation from the hematopoietic progenitor cells. See Table 1 below. The anti-proliferative effects were most pronounced using the −20 antisense and the +85 antisense oligonucleotide constructs. This inhibition was not lineage specific to any particular myeloid lineage that resulted from the progenitor expansion. The principal effect of the antisense oligonucleotides was a reduction of overall colony numbers. The size of the individual colonies was also reduced.

TABLE 1

| EXPERIMENT | OLIGO | AVG. COLONY # | % INHIBITION |
| --- | --- | --- | --- |
| Human Cord Blood (KL) | (−20)AS | 32 | |
| | (−20)S | 100 | 70 |
| | (−20)SCR | 114 | |
| | (+85)AS | 80 | |
| | (+85)S | 123 | 38 |
| | (+85)SCR | 138 | |
| | Control | 158 | |

TABLE 1-continued

| EXPERIMENT | OLIGO | AVG. COLONY # | % INHIBITION |
|---|---|---|---|
| Human Cord Blood | (−20)AS | 78 | |
| (IL−3, IL−6, KL) | (−20)S | 188 | 54 |
| | (−20)SCR | 151 | |
| | (+85)AS | 167 | |
| | (+85)S | 195 | 18 |
| | (+85)SCR | 213 | |
| | Control | 266 | |
| Human Cord Blood (KL) | (−20)AS | 42 | |
| | (−20)S | 146 | 69 |
| | (−20)SCR | 121 | |
| | (+85)AS | 123 | |
| | (+85)S | 162 | 23 |
| | (+85)SCR | 156 | |
| | Control | 145 | |
| Murine Fetal Liver (KL) | (+84)AS | 33 | |
| | (+84)S | 86 | 54 |
| | (+84)SCR | 57 | |
| | (−20)AS | 27 | |
| | (−20)S | 126 | 71 |
| | (−20)SCR | 60 | |
| | (−99)AS | 109 | |
| | (−99)S | 93 | 0 |
| | (−99)SCR | 109 | |
| | Control | 121 | |
| Murine Fetal Liver (KL) | (−213)AS | 51 | |
| | (−213)S | 60 | 10 |
| | (−213)SCR | 53 | |
| | (+211)AS | 58 | |
| | (+211)S | 54 | 3 |
| | (+211)SCR | 66 | |
| | Control | 59 | |

Materials and Methods

Human stem cells: Human umbilical cord blood was collected in PBS/Heparin (1000 u/ml). The mononuclear fraction was separated using a dextran gradient and any remaining red blood cells lysed in 20 mM $NH_4$ Cl. $CD34^+$ cells were isolated using $CD34^+$ immunomagnetic beads (Miltenyi, Calif.). These isolated $CD34^+$ cells were found to be 90–97% $CD34^+$ by FACS analysis.

Murine stem cells: Midgestation fetal liver were harvested and positively selected for the $AA4^-$ antigen by immune panning. The $AA4^-$ positive fraction was then further enriched for stem cell content by FACS isolation of the $AA4^+$ $Sca^+$ $Kit^+$ fraction.

Antisense expedments: Oligodeoxynucleotides were synthesized against regions of the human or murine WSX receptors. For each oligonucleotide chosen, antisense (AS), sense (S) and scrambled (SCR) versions were synthesized (see FIG. 7). + or − indicates position relative the initiation methionine of the WSX receptor. $CD34^+$ or $AA4^+$ $Sca^+$ $Kit^+$ cells were incubated at a concentration of $10^3$ /ml in 50:50 DMEM/F12 media supplemented with 10% FBS, L-glutamine, and GIBCO™ lipid concentrate containing either sense, antisense or scrambled oligonucleotides at a concentration of 70 μg/ml. After 16 hours, a second aliquot of the respective oligonucleotide was added (35 μg/ml) and the cells incubated for a further 6 hours.

Colony assays: 5000 cells from each of the above conditions were aliquoted into 5 ml of methylcellulose (Stem Cell Technologies) containing kit ligand (KL) (25 ng/ml), interleukin-3 (IL-3) (25 ng/ml) and interleukin-6 (IL-6) (50 ng/ml). The methylcellulose cultures were then incubated at 37° C. for 14 days and the resultant colonies counted and phenotyped. All assays were performed in triplicate.

What is claimed is:

1. Isolated WSX receptor comprising the amino acid sequence of mature human WSX receptor variant 12.1 as in SEQ ID NO:4.

* * * * *

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
      (A) LENGTH: 4102 base pairs
      (B) TYPE: Nucleic Acid
      (C) STRANDEDNESS: Double
      (D) TOPOLOGY: Linear (xi) SEQUENCE DESCRIPTION: SEQ ID NO:1:

```
GAATTCTCGA GTCGACGGCG GGCGTTAAAG CTCTCGTGGC ATTATCCTTC          50

AGTGGGGCTA TTGGACTGAC TTTTCTTATG CTGGGATGTG CCTTAGAGGA         100

TTATGGGTGT ACTTCTCTGA AGTAAGATGA TTTGTCAAAA ATTCTGTGTG         150

GTTTTGTTAC ATTGGGAATT TATTTATGTG ATAACTGCGT TTAACTTGTC         200

ATATCCAATT ACTCCTTGGA GATTTAAGTT GTCTTGCATG CCACCAAATT         250

CAACCTATGA CTACTTCCTT TTGCCTGCTG GACTCTCAAA GAATACTTCA         300

AATTCGAATG GACATTATGA GACAGCTGTT GAACCTAAGT TTAATTCAAG         350

TGGTACTCAC TTTTCTAACT TATCCAAAAC AACTTTCCAC TGTTGCTTTC         400

GGAGTGAGCA AGATAGAAAC TGCTCCTTAT GTGCAGACAA CATTGAAGGA         450

AAGACATTTG TTTCAACAGT AAATTCTTTA GTTTTTCAAC AAATAGATGC         500
```

-continued

| | |
|---|---|
| AAACTGGAAC ATACAGTGCT GGCTAAAAGG AGACTTAAAA TTATTCATCT | 550 |
| GTTATGTGGA GTCATTATTT AAGAATCTAT TCAGGAATTA TAACTATAAG | 600 |
| GTCCATCTTT TATATGTTCT GCCTGAAGTG TTAGAAGATT CACCTCTGGT | 650 |
| TCCCCAAAAA GGCAGTTTTC AGATGGTTCA CTGCAATTGC AGTGTTCATG | 700 |
| AATGTTGTGA ATGTCTTGTG CCTGTGCCAA CAGCCAAACT CAACGACACT | 750 |
| CTCCTTATGT GTTTGAAAAT CACATCTGGT GGAGTAATTT TCCAGTCACC | 800 |
| TCTAATGTCA GTTCAGCCCA TAAATATGGT GAAGCCTGAT CCACCATTAG | 850 |
| GTTTGCATAT GGAAATCACA GATGATGGTA ATTTAAAGAT TTCTTGGTCC | 900 |
| AGCCCACCAT TGGTACCATT TCCACTTCAA TATCAAGTGA AATATTCAGA | 950 |
| GAATTCTACA ACAGTTATCA GAGAAGCTGA CAAGATTGTC TCAGCTACAT | 1000 |
| CCCTGCTAGT AGACAGTATA CTTCCTGGGT CTTCGTATGA GGTTCAGGTG | 1050 |
| AGGGGCAAGA GACTGGATGG CCCAGGAATC TGGAGTGACT GGAGTACTCC | 1100 |
| TCGTGTCTTT ACCACACAAG ATGTCTATAT CTTTCCACCT AAAATTCTGA | 1150 |
| CAAGTGTTGG GTCTAATGTT TCTTTTCACT GCATCTATAA GAAGGAAAAC | 1200 |
| AAGATTGTTC CCTCAAAAGA GATTGTTTGG TGGATGAATT TAGCTGAGAA | 1250 |
| AATTCCTCAA AGCCAGTATG ATGTTGTGAG TGATCATGTT AGCAAAGTTA | 1300 |
| CTTTTTTCAA TCTGAATGAA ACCAAACCTC GAGGAAAGTT TACCTATGAT | 1350 |
| GCAGTGTACT GCTGCAATGA ACATGAATGC CATCATCGCT ATGCTGAATT | 1400 |
| ATATGTGATT GATGTCAATA TCAATATCTC ATGTGAAACT GATGGGTACT | 1450 |
| TAACTAAAAT GACTTGCAGA TGGTCAACCA GTACAATCCA GTCACTTGCG | 1500 |
| GAAAGCACTT TGCAATTGAG GTATCATAGG AGCAGCCTTT ACTGTTCTGA | 1550 |
| TATTCCATCT ATTCATCCCA TATCTGAGCC CAAAGATTGC TATTTGCAGA | 1600 |
| GTGATGGTTT TTATGAATGC ATTTTCCAGC CAATCTTCCT ATTATCTGGC | 1650 |
| TACACAATGT GGATTAGGAT CAATCACTCT CTAGGTTCAC TTGACTCTCC | 1700 |
| ACCAACATGT GTCCTTCCTG ATTCTGTGGT GAAGCCACTG CCTCCATCCA | 1750 |
| GTGTGAAAGC AGAAATTACT ATAAACATTG GATTATTGAA AATATCTTGG | 1800 |
| GAAAAGCCAG TCTTTCCAGA GAATAACCTT CAATTCCAGA TTCGCTATGG | 1850 |
| TTTAAGTGGA AAAGAAGTAC AATGGAAGAT GTATGAGGTT TATGATGCAA | 1900 |
| AATCAAAATC TGTCAGTCTC CCAGTTCCAG ACTTGTGTGC AGTCTATGCT | 1950 |
| GTTCAGGTGC GCTGTAAGAG GCTAGATGGA CTGGGATATT GGAGTAATTG | 2000 |
| GAGCAATCCA GCCTACACAG TTGTCATGGA TATAAAAGTT CCTATGAGAG | 2050 |
| GACCTGAATT TTGGAGAATA ATTAATGGAG ATACTATGAA AAAGGAGAAA | 2100 |
| AATGTCACTT TACTTTGGAA GCCCCTGATG AAAAATGACT CATTGTGCAG | 2150 |
| TGTTCAGAGA TATGTGATAA ACCATCATAC TTCCTGCAAT GGAACATGGT | 2200 |
| CAGAAGATGT GGGAAATCAC ACGAAATTCA CTTTCCTGTG GACAGAGCAA | 2250 |
| GCACATACTG TTACGGTTCT GGCCATCAAT TCAATTGGTG CTTCTGTTGC | 2300 |
| AAATTTTAAT TTAACCTTTT CATGGCCTAT GAGCAAAGTA AATATCGTGC | 2350 |
| AGTCACTCAG TGCTTATCCT TTAAACAGCA GTTGTGTGAT TGTTTCCTGG | 2400 |
| ATACTATCAC CCAGTGATTA CAAGCTAATG TATTTTATTA TTGAGTGGAA | 2450 |
| AAATCTTAAT GAAGATGGTG AAATAAAATG GCTTAGAATC TCTTCATCTG | 2500 |

```
TTAAGAAGTA TTATATCCAT GATCATTTTA TCCCCATTGA GAAGTACCAG       2550

TTCAGTCTTT ACCCAATATT TATGGAAGGA GTGGGAAAAC CAAAGATAAT       2600

TAATAGTTTC ACTCAAGATG ATATTGAAAA ACACCAGAGT GATGCAGGTT       2650

TATATGTAAT TGTGCCAGTA ATTATTTCCT CTTCCATCTT ATTGCTTGGA       2700

ACATTATTAA TATCACACCA AGAATGAAA AAGCTATTTT GGGAAGATGT        2750

TCCGAACCCC AAGAATTGTT CCTGGGCACA AGGACTTAAT TTTCAGAAGC       2800

CAGAAACGTT TGAGCATCTT TTTATCAAGC ATACAGCATC AGTGACATGT       2850

GGTCCTCTTC TTTTGGAGCC TGAAACAATT TCAGAAGATA TCAGTGTTGA       2900

TACATCATGG AAAAATAAAG ATGAGATGAT GCCAACAACT GTGGTCTCTC       2950

TACTTTCAAC AACAGATCTT GAAAAGGGTT CTGTTTGTAT TAGTGACCAG       3000

TTCAACAGTG TTAACTTCTC TGAGGCTGAG GGTACTGAGG TAACCTATGA       3050

GGACGAAAGC CAGAGACAAC CCTTTGTTAA ATACGCCACG CTGATCAGCA       3100

ACTCTAAACC AAGTGAAACT GGTGAAGAAC AAGGGCTTAT AAATAGTTCA       3150

GTCACCAAGT GCTTCTCTAG CAAAAATTCT CCGTTGAAGG ATTCTTTCTC       3200

TAATAGCTCA TGGGAGATAG AGGCCCAGGC ATTTTTTATA TTATCAGATC       3250

AGCATCCCAA CATAATTTCA CCACACCTCA CATTCTCAGA AGGATTGGAT       3300

GAACTTTTGA AATTGGAGGG AAATTTCCCT GAAGAAAATA ATGATAAAAA       3350

GTCTATCTAT TATTTAGGGG TCACCTCAAT CAAAAAGAGA GAGAGTGGTG       3400

TGCTTTTGAC TGACAAGTCA AGGGTATCGT GCCCATTCCC AGCCCCCTGT       3450

TTATTCACGG ACATCAGAGT TCTCCAGGAC AGTTGCTCAC ACTTTGTAGA       3500

AAATAATATC AACTTAGGAA CTTCTAGTAA GAAGACTTTT GCATCTTACA       3550

TGCCTCAATT CCAAACTTGT TCTACTCAGA CTCATAAGAT CATGGAAAAC       3600

AAGATGTGTG ACCTAACTGT GTAATTTCAC TGAAGAAACC TTCAGATTTG       3650

TGTTATAATG GGTAATATAA AGTGTAATAG ATTATAGTTG TGGGTGGGAG       3700

AGAGAAAAGA AACCAGAGTC AAATTTGAAA ATAATTGTTC CAAATGAATG       3750

TTGTCTGTTT GTTCTCTCTT AGTAACATAG ACAAAAAATT TGAGAAAGCC       3800

TTCATAAGCC TACCAATGTA GACACGCTCT TCTATTTTAT TCCCAAGCTC       3850

TAGTGGGAAG GTCCCTTGTT TCCAGCTAGA AATAAGCCCA ACAGACACCA       3900

TCTTTTGTGA GATGTAATTG TTTTTTCAGA GGGCGTGTTG TTTTACCTCA       3950

AGTTTTTGTT TTGTACCAAC ACACACACAC ACACACATTC TTAACACATG       4000

TCCTTGTGTG TTTTGAGAGT ATATTATGTA TTTATATTTT GTGCTATCAG       4050

ACTGTAGGAT TTGAAGTAGG ACTTCCTAA ATGTTTAAGA TAAACAGAAT        4100

TC                                                          4102
```

(2) INFORMATION FOR SEQ ID NO:2:

(i) SEQUENCE CHARACTERISTICS:
        (A) LENGTH: 1165 amino acids
        (B) TYPE: Amino Acid
        (D) TOPOLOGY: Linear (xi) SEQUENCE DESCRIPTION: SEQ ID NO:2:

```
Met Ile Cys Gln Lys Phe Cys Val Val Leu Leu His Trp Glu Phe
 1               5                  10                  15
```

-continued

Ile Tyr Val Ile Thr Ala Phe Asn Leu Ser Tyr Pro Ile Thr Pro
                20                  25                  30

Trp Arg Phe Lys Leu Ser Cys Met Pro Pro Asn Ser Thr Tyr Asp
            35                  40                  45

Tyr Phe Leu Leu Pro Ala Gly Leu Ser Lys Asn Thr Ser Asn Ser
        50                  55                  60

Asn Gly His Tyr Glu Thr Ala Val Glu Pro Lys Phe Asn Ser Ser
    65                  70                  75

Gly Thr His Phe Ser Asn Leu Ser Lys Thr Thr Phe His Cys Cys
80                  85                  90

Phe Arg Ser Glu Gln Asp Arg Asn Cys Ser Leu Cys Ala Asp Asn
            95                 100                 105

Ile Glu Gly Lys Thr Phe Val Ser Thr Val Asn Ser Leu Val Phe
        110                 115                 120

Gln Gln Ile Asp Ala Asn Trp Asn Ile Gln Cys Trp Leu Lys Gly
    125                 130                 135

Asp Leu Lys Leu Phe Ile Cys Tyr Val Glu Ser Leu Phe Lys Asn
140                 145                 150

Leu Phe Arg Asn Tyr Asn Tyr Lys Val His Leu Leu Tyr Val Leu
            155                 160                 165

Pro Glu Val Leu Glu Asp Ser Pro Leu Val Pro Gln Lys Gly Ser
        170                 175                 180

Phe Gln Met Val His Cys Asn Cys Ser Val His Glu Cys Cys Glu
    185                 190                 195

Cys Leu Val Pro Val Pro Thr Ala Lys Leu Asn Asp Thr Leu Leu
200                 205                 210

Met Cys Leu Lys Ile Thr Ser Gly Val Ile Phe Gln Ser Pro
            215                 220                 225

Leu Met Ser Val Gln Pro Ile Asn Met Val Lys Pro Asp Pro Pro
        230                 235                 240

Leu Gly Leu His Met Glu Ile Thr Asp Asp Gly Asn Leu Lys Ile
    245                 250                 255

Ser Trp Ser Ser Pro Pro Leu Val Pro Phe Pro Leu Gln Tyr Gln
260                 265                 270

Val Lys Tyr Ser Glu Asn Ser Thr Thr Val Ile Arg Glu Ala Asp
            275                 280                 285

Lys Ile Val Ser Ala Thr Ser Leu Leu Val Asp Ser Ile Leu Pro
        290                 295                 300

Gly Ser Ser Tyr Glu Val Gln Val Arg Gly Lys Arg Leu Asp Gly
    305                 310                 315

Pro Gly Ile Trp Ser Asp Trp Ser Thr Pro Arg Val Phe Thr Thr
320                 325                 330

Gln Asp Val Ile Tyr Phe Pro Pro Lys Ile Leu Thr Ser Val Gly
            335                 340                 345

Ser Asn Val Ser Phe His Cys Ile Tyr Lys Lys Glu Asn Lys Ile
        350                 355                 360

Val Pro Ser Lys Glu Ile Val Trp Trp Met Asn Leu Ala Glu Lys
    365                 370                 375

Ile Pro Gln Ser Gln Tyr Asp Val Val Ser Asp His Val Ser Lys
380                 385                 390

Val Thr Phe Phe Asn Leu Asn Glu Thr Lys Pro Arg Gly Lys Phe
            395                 400                 405

-continued

```
Thr Tyr Asp Ala Val Tyr Cys Cys Asn Glu His Glu Cys His His
                410                 415                 420
Arg Tyr Ala Glu Leu Tyr Val Ile Asp Val Asn Ile Asn Ile Ser
            425                 430                 435
Cys Glu Thr Asp Gly Tyr Leu Thr Lys Met Thr Cys Arg Trp Ser
            440                 445                 450
Thr Ser Thr Ile Gln Ser Leu Ala Glu Ser Thr Leu Gln Leu Arg
            455                 460                 465
Tyr His Arg Ser Ser Leu Tyr Cys Ser Asp Ile Pro Ser Ile His
            470                 475                 480
Pro Ile Ser Glu Pro Lys Asp Cys Tyr Leu Gln Ser Asp Gly Phe
            485                 490                 495
Tyr Glu Cys Ile Phe Gln Pro Ile Phe Leu Leu Ser Gly Tyr Thr
            500                 505                 510
Met Trp Ile Arg Ile Asn His Ser Leu Gly Ser Leu Asp Ser Pro
            515                 520                 525
Pro Thr Cys Val Leu Pro Asp Ser Val Val Lys Pro Leu Pro Pro
            530                 535                 540
Ser Ser Val Lys Ala Glu Ile Thr Ile Asn Ile Gly Leu Leu Lys
            545                 550                 555
Ile Ser Trp Glu Lys Pro Val Phe Pro Glu Asn Asn Leu Gln Phe
            560                 565                 570
Gln Ile Arg Tyr Gly Leu Ser Gly Lys Glu Val Gln Trp Lys Met
            575                 580                 585
Tyr Glu Val Tyr Asp Ala Lys Ser Lys Ser Val Ser Leu Pro Val
            590                 595                 600
Pro Asp Leu Cys Ala Val Tyr Ala Val Gln Val Arg Cys Lys Arg
            605                 610                 615
Leu Asp Gly Leu Gly Tyr Trp Ser Asn Trp Ser Asn Pro Ala Tyr
            620                 625                 630
Thr Val Val Met Asp Ile Lys Val Pro Met Arg Gly Pro Glu Phe
            635                 640                 645
Trp Arg Ile Ile Asn Gly Asp Thr Met Lys Lys Glu Lys Asn Val
            650                 655                 660
Thr Leu Leu Trp Lys Pro Leu Met Lys Asn Asp Ser Leu Cys Ser
            665                 670                 675
Val Gln Arg Tyr Val Ile Asn His His Thr Ser Cys Asn Gly Thr
            680                 685                 690
Trp Ser Glu Asp Val Gly Asn His Thr Lys Phe Thr Phe Leu Trp
            695                 700                 705
Thr Glu Gln Ala His Thr Val Thr Val Leu Ala Ile Asn Ser Ile
            710                 715                 720
Gly Ala Ser Val Ala Asn Phe Asn Leu Thr Phe Ser Trp Pro Met
            725                 730                 735
Ser Lys Val Asn Ile Val Gln Ser Leu Ser Ala Tyr Pro Leu Asn
            740                 745                 750
Ser Ser Cys Val Ile Val Ser Trp Ile Leu Ser Pro Ser Asp Tyr
            755                 760                 765
Lys Leu Met Tyr Phe Ile Ile Glu Trp Lys Asn Leu Asn Glu Asp
            770                 775                 780
Gly Glu Ile Lys Trp Leu Arg Ile Ser Ser Ser Val Lys Lys Tyr
            785                 790                 795
```

-continued

```
Tyr Ile His Asp His Phe Ile Pro Ile Glu Lys Tyr Gln Phe Ser
                800             805                 810
Leu Tyr Pro Ile Phe Met Glu Gly Val Gly Lys Pro Lys Ile Ile
                815             820                 825
Asn Ser Phe Thr Gln Asp Asp Ile Glu Lys His Gln Ser Asp Ala
                830             835                 840
Gly Leu Tyr Val Ile Val Pro Val Ile Ile Ser Ser Ser Ile Leu
                845             850                 855
Leu Leu Gly Thr Leu Leu Ile Ser His Gln Arg Met Lys Lys Leu
                860             865                 870
Phe Trp Glu Asp Val Pro Asn Pro Lys Asn Cys Ser Trp Ala Gln
                875             880                 885
Gly Leu Asn Phe Gln Lys Pro Glu Thr Phe Glu His Leu Phe Ile
                890             895                 900
Lys His Thr Ala Ser Val Thr Cys Gly Pro Leu Leu Leu Glu Pro
                905             910                 915
Glu Thr Ile Ser Glu Asp Ile Ser Val Asp Thr Ser Trp Lys Asn
                920             925                 930
Lys Asp Glu Met Met Pro Thr Thr Val Ser Leu Leu Ser Thr
                935             940                 945
Thr Asp Leu Glu Lys Gly Ser Val Cys Ile Ser Asp Gln Phe Asn
                950             955                 960
Ser Val Asn Phe Ser Glu Ala Glu Gly Thr Glu Val Thr Tyr Glu
                965             970                 975
Asp Glu Ser Gln Arg Gln Pro Phe Val Lys Tyr Ala Thr Leu Ile
                980             985                 990
Ser Asn Ser Lys Pro Ser Glu Thr Gly Glu Gln Gly Leu Ile
                995             1000                1005
Asn Ser Ser Val Thr Lys Cys Phe Ser Ser Lys Asn Ser Pro Leu
                1010            1015                1020
Lys Asp Ser Phe Ser Asn Ser Ser Trp Glu Ile Glu Ala Gln Ala
                1025            1030                1035
Phe Phe Ile Leu Ser Asp Gln His Pro Asn Ile Ile Ser Pro His
                1040            1045                1050
Leu Thr Phe Ser Glu Gly Leu Asp Glu Leu Leu Lys Leu Glu Gly
                1055            1060                1065
Asn Phe Pro Glu Glu Asn Asn Asp Lys Lys Ser Ile Tyr Tyr Leu
                1070            1075                1080
Gly Val Thr Ser Ile Lys Lys Arg Glu Ser Gly Val Leu Leu Thr
                1085            1090                1095
Asp Lys Ser Arg Val Ser Cys Pro Phe Pro Ala Pro Cys Leu Phe
                1100            1105                1110
Thr Asp Ile Arg Val Leu Gln Asp Ser Cys Ser His Phe Val Glu
                1115            1120                1125
Asn Asn Ile Asn Leu Gly Thr Ser Ser Lys Lys Thr Phe Ala Ser
                1130            1135                1140
Tyr Met Pro Gln Phe Gln Thr Cys Ser Thr Gln Thr His Lys Ile
                1145            1150                1155
Met Glu Asn Lys Met Cys Asp Leu Thr Val
                1160            1165
```

(2) INFORMATION FOR SEQ ID NO:3:

(i) SEQUENCE CHARACTERISTICS:
       (A) LENGTH: 896 amino acids
       (B) TYPE: Amino Acid
       (D) TOPOLOGY: Linear (xi) SEQUENCE DESCRIPTION: SEQ ID NO:3:

```
Met Ile Cys Gln Lys Phe Cys Val Val Leu Leu His Trp Glu Phe
 1               5                  10                  15

Ile Tyr Val Ile Thr Ala Phe Asn Leu Ser Tyr Pro Ile Thr Pro
                20                  25                  30

Trp Arg Phe Lys Leu Ser Cys Met Pro Pro Asn Ser Thr Tyr Asp
                35                  40                  45

Tyr Phe Leu Leu Pro Ala Gly Leu Ser Lys Asn Thr Ser Asn Ser
                50                  55                  60

Asn Gly His Tyr Glu Thr Ala Val Glu Pro Lys Phe Asn Ser Ser
                65                  70                  75

Gly Thr His Phe Ser Asn Leu Ser Lys Thr Thr Phe His Cys Cys
                80                  85                  90

Phe Arg Ser Glu Gln Asp Arg Asn Cys Ser Leu Cys Ala Asp Asn
                95                 100                 105

Ile Glu Gly Lys Thr Phe Val Ser Thr Val Asn Ser Leu Val Phe
               110                 115                 120

Gln Gln Ile Asp Ala Asn Trp Asn Ile Gln Cys Trp Leu Lys Gly
               125                 130                 135

Asp Leu Lys Leu Phe Ile Cys Tyr Val Glu Ser Leu Phe Lys Asn
               140                 145                 150

Leu Phe Arg Asn Tyr Asn Tyr Lys Val His Leu Leu Tyr Val Leu
               155                 160                 165

Pro Glu Val Leu Glu Asp Ser Pro Leu Val Pro Gln Lys Gly Ser
               170                 175                 180

Phe Gln Met Val His Cys Asn Cys Ser Val His Glu Cys Cys Glu
               185                 190                 195

Cys Leu Val Pro Val Pro Thr Ala Lys Leu Asn Asp Thr Leu Leu
               200                 205                 210

Met Cys Leu Lys Ile Thr Ser Gly Gly Val Ile Phe Gln Ser Pro
               215                 220                 225

Leu Met Ser Val Gln Pro Ile Asn Met Val Lys Pro Asp Pro Pro
               230                 235                 240

Leu Gly Leu His Met Glu Ile Thr Asp Asp Gly Asn Leu Lys Ile
               245                 250                 255

Ser Trp Ser Ser Pro Pro Leu Val Pro Phe Pro Leu Gln Tyr Gln
               260                 265                 270

Val Lys Tyr Ser Glu Asn Ser Thr Thr Val Ile Arg Glu Ala Asp
               275                 280                 285

Lys Ile Val Ser Ala Thr Ser Leu Leu Val Asp Ser Ile Leu Pro
               290                 295                 300

Gly Ser Ser Tyr Glu Val Gln Val Arg Gly Lys Arg Leu Asp Gly
               305                 310                 315

Pro Gly Ile Trp Ser Asp Trp Ser Thr Pro Arg Val Phe Thr Thr
               320                 325                 330

Gln Asp Val Ile Tyr Phe Pro Pro Lys Ile Leu Thr Ser Val Gly
               335                 340                 345
```

-continued

```
Ser Asn Val Ser Phe His Cys Ile Tyr Lys Lys Glu Asn Lys Ile
                350                 355                 360

Val Pro Ser Lys Glu Ile Val Trp Trp Met Asn Leu Ala Glu Lys
            365                 370                 375

Ile Pro Gln Ser Gln Tyr Asp Val Ser Asp His Val Ser Lys
            380                 385                 390

Val Thr Phe Phe Asn Leu Asn Glu Thr Lys Pro Arg Gly Lys Phe
            395                 400                 405

Thr Tyr Asp Ala Val Tyr Cys Cys Asn Glu His Glu Cys His His
            410                 415                 420

Arg Tyr Ala Glu Leu Tyr Val Ile Asp Val Asn Ile Asn Ile Ser
            425                 430                 435

Cys Glu Thr Asp Gly Tyr Leu Thr Lys Met Thr Cys Arg Trp Ser
            440                 445                 450

Thr Ser Thr Ile Gln Ser Leu Ala Glu Ser Thr Leu Gln Leu Arg
            455                 460                 465

Tyr His Arg Ser Ser Leu Tyr Cys Ser Asp Ile Pro Ser Ile His
            470                 475                 480

Pro Ile Ser Glu Pro Lys Asp Cys Tyr Leu Gln Ser Asp Gly Phe
            485                 490                 495

Tyr Glu Cys Ile Phe Gln Pro Ile Phe Leu Leu Ser Gly Tyr Thr
            500                 505                 510

Met Trp Ile Arg Ile Asn His Ser Leu Gly Ser Leu Asp Ser Pro
            515                 520                 525

Pro Thr Cys Val Leu Pro Asp Ser Val Lys Pro Leu Pro Pro
            530                 535                 540

Ser Ser Val Lys Ala Glu Ile Thr Ile Asn Ile Gly Leu Leu Lys
            545                 550                 555

Ile Ser Trp Glu Lys Pro Val Phe Pro Glu Asn Asn Leu Gln Phe
            560                 565                 570

Gln Ile Arg Tyr Gly Leu Ser Gly Lys Glu Val Gln Trp Lys Met
            575                 580                 585

Tyr Glu Val Tyr Asp Ala Lys Ser Lys Ser Val Ser Leu Pro Val
            590                 595                 600

Pro Asp Leu Cys Ala Val Tyr Ala Val Gln Val Arg Cys Lys Arg
            605                 610                 615

Leu Asp Gly Leu Gly Tyr Trp Ser Asn Trp Ser Asn Pro Ala Tyr
            620                 625                 630

Thr Val Val Met Asp Ile Lys Val Pro Met Arg Gly Pro Glu Phe
            635                 640                 645

Trp Arg Ile Ile Asn Gly Asp Thr Met Lys Lys Glu Lys Asn Val
            650                 655                 660

Thr Leu Leu Trp Lys Pro Leu Met Lys Asn Asp Ser Leu Cys Ser
            665                 670                 675

Val Gln Arg Tyr Val Ile Asn His His Thr Ser Cys Asn Gly Thr
            680                 685                 690

Trp Ser Glu Asp Val Gly Asn His Thr Lys Phe Thr Phe Leu Trp
            695                 700                 705

Thr Glu Gln Ala His Thr Val Thr Val Leu Ala Ile Asn Ser Ile
            710                 715                 720

Gly Ala Ser Val Ala Asn Phe Asn Leu Thr Phe Ser Trp Pro Met
            725                 730                 735
```

-continued

```
Ser Lys Val Asn Ile Val Gln Ser Leu Ser Ala Tyr Pro Leu Asn
            740                 745                 750

Ser Ser Cys Val Ile Val Ser Trp Ile Leu Ser Pro Ser Asp Tyr
            755                 760                 765

Lys Leu Met Tyr Phe Ile Ile Glu Trp Lys Asn Leu Asn Glu Asp
            770                 775                 780

Gly Glu Ile Lys Trp Leu Arg Ile Ser Ser Val Lys Lys Tyr
            785                 790                 795

Tyr Ile His Asp His Phe Ile Pro Ile Glu Lys Tyr Gln Phe Ser
            800                 805                 810

Leu Tyr Pro Ile Phe Met Glu Gly Val Gly Lys Pro Lys Ile Ile
            815                 820                 825

Asn Ser Phe Thr Gln Asp Asp Ile Glu Lys His Gln Ser Asp Ala
            830                 835                 840

Gly Leu Tyr Val Ile Val Pro Val Ile Ile Ser Ser Ser Ile Leu
            845                 850                 855

Leu Leu Gly Thr Leu Leu Ile Ser His Gln Arg Met Lys Lys Leu
            860                 865                 870

Phe Trp Glu Asp Val Pro Asn Pro Lys Asn Cys Ser Trp Ala Gln
            875                 880                 885

Gly Leu Asn Phe Gln Lys Arg Thr Asp Ile Leu
            890                 895 896
```

(2) INFORMATION FOR SEQ ID NO:4:

(i) SEQUENCE CHARACTERISTICS:
        (A) LENGTH: 923 amino acids
        (B) TYPE: Amino Acid
        (D) TOPOLOGY: Linear (xi) SEQUENCE DESCRIPTION: SEQ ID NO:4:

```
Met Ile Cys Gln Lys Phe Cys Val Val Leu Leu His Trp Glu Phe
 1               5                  10                  15

Ile Tyr Val Ile Thr Ala Phe Asn Leu Ser Tyr Pro Ile Thr Pro
                20                  25                  30

Trp Arg Phe Lys Leu Ser Cys Met Pro Pro Asn Ser Thr Tyr Asp
                35                  40                  45

Tyr Phe Leu Leu Pro Ala Gly Leu Ser Lys Asn Thr Ser Asn Ser
                50                  55                  60

Asn Gly His Tyr Glu Thr Ala Val Glu Pro Lys Phe Asn Ser Ser
                65                  70                  75

Gly Thr His Phe Ser Asn Leu Ser Lys Thr Thr Phe His Cys Cys
                80                  85                  90

Phe Arg Ser Glu Gln Asp Arg Asn Cys Ser Leu Cys Ala Asp Asn
                95                  100                 105

Ile Glu Gly Lys Thr Phe Val Ser Thr Val Asn Ser Leu Val Phe
                110                 115                 120

Gln Gln Ile Asp Ala Asn Trp Asn Ile Gln Cys Trp Leu Lys Gly
                125                 130                 135

Asp Leu Lys Leu Phe Ile Cys Tyr Val Glu Ser Leu Phe Lys Asn
                140                 145                 150

Leu Phe Arg Asn Tyr Asn Tyr Lys Val His Leu Leu Tyr Val Leu
                155                 160                 165

Pro Glu Val Leu Glu Asp Ser Pro Val Pro Gln Lys Gly Ser
                170                 175                 180
```

-continued

Phe Gln Met Val His Cys Asn Cys Ser Val His Glu Cys Cys Glu
            185                 190                 195

Cys Leu Val Pro Val Pro Thr Ala Lys Leu Asn Asp Thr Leu Leu
            200                 205                 210

Met Cys Leu Lys Ile Thr Ser Gly Gly Val Ile Phe Gln Ser Pro
            215                 220                 225

Leu Met Ser Val Gln Pro Ile Asn Met Val Lys Pro Asp Pro Pro
            230                 235                 240

Leu Gly Leu His Met Glu Ile Thr Asp Asp Gly Asn Leu Lys Ile
            245                 250                 255

Ser Trp Ser Ser Pro Pro Leu Val Pro Phe Pro Leu Gln Tyr Gln
            260                 265                 270

Val Lys Tyr Ser Glu Asn Ser Thr Thr Val Ile Arg Glu Ala Asp
            275                 280                 285

Lys Ile Val Ser Ala Thr Ser Leu Leu Val Asp Ser Ile Leu Pro
            290                 295                 300

Gly Ser Ser Tyr Glu Val Gln Val Arg Gly Lys Arg Leu Asp Gly
            305                 310                 315

Pro Gly Ile Trp Ser Asp Trp Ser Thr Pro Arg Val Phe Thr Thr
            320                 325                 330

Gln Asp Val Ile Tyr Phe Pro Pro Lys Ile Leu Thr Ser Val Gly
            335                 340                 345

Ser Asn Val Ser Phe His Cys Ile Tyr Lys Lys Glu Asn Lys Ile
            350                 355                 360

Val Pro Ser Lys Glu Ile Val Trp Trp Met Asn Leu Ala Glu Lys
            365                 370                 375

Ile Pro Gln Ser Gln Tyr Asp Val Val Ser Asp His Val Ser Lys
            380                 385                 390

Val Thr Phe Phe Asn Leu Asn Glu Thr Lys Pro Arg Gly Lys Phe
            395                 400                 405

Thr Tyr Asp Ala Val Tyr Cys Cys Asn Glu His Glu Cys His His
            410                 415                 420

Arg Tyr Ala Glu Leu Tyr Val Ile Asp Val Asn Ile Asn Ile Ser
            425                 430                 435

Cys Glu Thr Asp Gly Tyr Leu Thr Lys Met Thr Cys Arg Trp Ser
            440                 445                 450

Thr Ser Thr Ile Gln Ser Leu Ala Glu Ser Thr Leu Gln Leu Arg
            455                 460                 465

Tyr His Arg Ser Ser Leu Tyr Cys Ser Asp Ile Pro Ser Ile His
            470                 475                 480

Pro Ile Ser Glu Pro Lys Asp Cys Tyr Leu Gln Ser Asp Gly Phe
            485                 490                 495

Tyr Glu Cys Ile Phe Gln Pro Ile Phe Leu Leu Ser Gly Tyr Thr
            500                 505                 510

Met Trp Ile Arg Ile Asn His Ser Leu Gly Ser Leu Asp Ser Pro
            515                 520                 525

Pro Thr Cys Val Leu Pro Asp Ser Val Val Lys Pro Leu Pro Pro
            530                 535                 540

Ser Ser Val Lys Ala Glu Ile Thr Ile Asn Ile Gly Leu Leu Lys
            545                 550                 555

Ile Ser Trp Glu Lys Pro Val Phe Pro Glu Asn Asn Leu Gln Phe
            560                 565                 570

```
Gln Ile Arg Tyr Gly Leu Ser Gly Lys Glu Val Gln Trp Lys Met
                575                 580                 585

Tyr Glu Val Tyr Asp Ala Lys Ser Lys Ser Val Ser Leu Pro Val
                590                 595                 600

Pro Asp Leu Cys Ala Val Tyr Ala Val Gln Val Arg Cys Lys Arg
                605                 610                 615

Leu Asp Gly Leu Gly Tyr Trp Ser Asn Trp Ser Asn Pro Ala Tyr
                620                 625                 630

Thr Val Val Met Asp Ile Lys Val Pro Met Arg Gly Pro Glu Phe
                635                 640                 645

Trp Arg Ile Ile Asn Gly Asp Thr Met Lys Lys Glu Lys Asn Val
                650                 655                 660

Thr Leu Leu Trp Lys Pro Leu Met Lys Asn Asp Ser Leu Cys Ser
                665                 670                 675

Val Gln Arg Tyr Val Ile Asn His His Thr Ser Cys Asn Gly Thr
                680                 685                 690

Trp Ser Glu Asp Val Gly Asn His Thr Lys Phe Thr Phe Leu Trp
                695                 700                 705

Thr Glu Gln Ala His Thr Val Thr Val Leu Ala Ile Asn Ser Ile
                710                 715                 720

Gly Ala Ser Val Ala Asn Phe Asn Leu Thr Phe Ser Trp Pro Met
                725                 730                 735

Ser Lys Val Asn Ile Val Gln Ser Leu Ser Ala Tyr Pro Leu Asn
                740                 745                 750

Ser Ser Cys Val Ile Val Ser Trp Ile Leu Ser Pro Ser Asp Tyr
                755                 760                 765

Lys Leu Met Tyr Phe Ile Ile Glu Trp Lys Asn Leu Asn Glu Asp
                770                 775                 780

Gly Glu Ile Lys Trp Leu Arg Ile Ser Ser Ser Val Lys Lys Tyr
                785                 790                 795

Tyr Ile His Asp His Phe Ile Pro Ile Glu Lys Tyr Gln Phe Ser
                800                 805                 810

Leu Tyr Pro Ile Phe Met Glu Gly Val Gly Lys Pro Lys Ile Ile
                815                 820                 825

Asn Ser Phe Thr Gln Asp Asp Ile Glu Lys His Gln Ser Asp Ala
                830                 835                 840

Gly Leu Tyr Val Ile Val Pro Val Ile Ile Ser Ser Ser Ile Leu
                845                 850                 855

Leu Leu Gly Thr Leu Leu Ile Ser His Gln Arg Met Lys Lys Leu
                860                 865                 870

Phe Trp Glu Asp Val Pro Asn Pro Lys Asn Cys Ser Trp Ala Gln
                875                 880                 885

Gly Leu Asn Phe Gln Lys Met Phe Arg Thr Pro Arg Ile Val Pro
                890                 895                 900

Gly His Lys Asp Leu Ile Phe Arg Arg Cys Leu Lys Ala Ala Cys
                905                 910                 915

Ser Leu Arg Val Ile Thr Thr Pro
                920             923

(2) INFORMATION FOR SEQ ID NO:5:

(i) SEQUENCE CHARACTERISTICS:
        (A) LENGTH: 3004 base pairs
        (B) TYPE: Nucleic Acid
```

(C) STRANDEDNESS: Single
    (D) TOPOLOGY: Linear (xi) SEQUENCE DESCRIPTION: SEQ ID NO:5:

| | | | | | |
|---|---|---|---|---|---|
| GAATTCCGGG | TTAAAGCTCT | CGTGGCATTA | TCCTTCAGTG | GGGCTATTGG | 50 |
| ACTGACTTTT | CTTATGCTGG | GATGTGCCTT | AGAGGATTAT | GGATTTGCCA | 100 |
| GTTCACCCTG | ACCATCTTGA | AAATAAGTTA | TCTCTGATCT | CTGTCTGTAT | 150 |
| GTTACTTCTC | TCCCCTCACC | AATGGAGAAC | AAATGTGGGC | AAAGTGTACT | 200 |
| TCTCTGAAGT | AAGATGATTT | GTCAAAAATT | CTGTGTGGTT | TTGTTACATT | 250 |
| GGGAATTTAT | TTATGTGATA | ACTGCGTTTA | ACTTGTCATA | TCCAATTACT | 300 |
| CCTTGGAGAT | TTAAGTTGTC | TTGCATGCCA | CCAAATTCAA | CCTATGACTA | 350 |
| CTTCCTTTTG | CCTGCTGGAC | TCTCAAAGAA | TACTTCAAAT | TCGAATGGAC | 400 |
| ATTATGAGAC | AGCTGTTGAA | CCTAAGTTTA | ATTCAAGTGG | TACTCACTTT | 450 |
| TCTAACTTAT | CCAAAACAAC | TTTCCACTGT | TGCTTTCGGA | GTGAGCAAGA | 500 |
| TAGAAACTGC | TCCTTATGTG | CAGACAACAT | TGAAGGAAAG | ACATTTGTTT | 550 |
| CNACAGTAAA | TTCTTTAGTT | TTTCAACAAA | TAGATGCAAA | CTGGAACATA | 600 |
| CAGTGCTGGC | TAAAAGGAGA | CTTAAAATTA | TTCATCTGTT | ATGTGGAGTC | 650 |
| ATTATTTAAG | AATCTATTCA | GGAATTATAA | CTATAAGGTC | CATCTTTTAT | 700 |
| ATGTTCTGCC | TGAAGTGTTA | GAAGATTCAC | CTCTGGTTCC | CCAAAAAGGC | 750 |
| AGTTTTCAGA | TGGTTCACTG | CAATTGCAGT | GTTCATGAAT | GTTGTGAATG | 800 |
| TCTTGTGCCT | GTGCCAACAG | CCAAACTCAA | CGACACTCTC | CTTATGTGTT | 850 |
| TGAAAATCAC | ATCTGGTGGA | GTAATTTTCC | AGTCACCTCT | AATGTCAGTT | 900 |
| CAGCCCATAA | ATATGGTGAA | GCCTGATCCA | CCATTAGGTT | TGCATATGGA | 950 |
| AATCACAGAT | GATGGTAATT | TAAAGATTTC | TTGGTCCAGC | CCACCATTGG | 1000 |
| TACCATTTCC | ACTTCAATAT | CAAGTGAAAT | ATTCAGAGAA | TTCTACAACA | 1050 |
| GTTATCAGAG | AAGCTGACAA | GATTGTCTCA | GCTACATCCC | TGCTAGTAGA | 1100 |
| CAGTATACTT | CCTGGGTCTT | CGTATGAGGT | TCAGGTGAGG | GGCAAGAGAC | 1150 |
| TGGATGGCCC | AGGAATCTGG | AGTGACTGGA | GTACTCCTCG | TGTCTTTACC | 1200 |
| ACACAAGATG | TCATATACTT | TCCACCTAAA | ATTCTGACAA | GTGTTGGGTC | 1250 |
| TAATGTTTCT | TTTCACTGCA | TCTATAAGAA | GGAAAACAAG | ATTGTTCCCT | 1300 |
| CAAAAGAGAT | TGTTTGGTGG | ATGAATTTAG | CTGAGAAAAT | TCCTCAAAGC | 1350 |
| CAGTATGATG | TTGTGAGTGA | TCATGTTAGC | AAAGTTACTT | TTTTCAATCT | 1400 |
| GAATGAAACC | AAACCTCGAG | GAAAGTTTAC | CTATGATGCA | GTGTACTGCT | 1450 |
| GCAATGAACA | TGAATGCCAT | CATCGCTATG | CTGAATTATA | TGTGATTGAT | 1500 |
| GTCAATATCA | ATATCTCATG | TGAAACTGAT | GGGTACTTAA | CTAAAATGAC | 1550 |
| TTGCAGATGG | TCAACCAGTA | CAATCCAGTC | ACTTGCGGAA | AGCACTTTGC | 1600 |
| AATTGAGGTA | TCATAGGAGC | AGCCTTTACT | GTTCTGATAT | CCATCTATT | 1650 |
| CATCCCATAT | CTGAGCCCAA | AGATTGCTAT | TTGCAGAGTG | ATGGTTTTA | 1700 |
| TGAATGCATT | TTCCAGCCAA | TCTTCCTATT | ATCTGGCTAC | ACAATGTGGA | 1750 |
| TTAGGATCAA | TCACTCTCTA | GGTTCACTTG | ACTCTCCACC | AACATGTGTC | 1800 |
| CTTCCTGATT | CTGTGGTGAA | GCCACTGCCT | CCATCCAGTG | TGAAAGCAGA | 1850 |

| | |
|---|---|
| AATTACTATA AACATTGGAT TATTGAAAAT ATCTTGGGAA AAGCCAGTCT | 1900 |
| TTCCAGAGAA TAACCTTCAA TTCCAGATTC GCTATGGTTT AAGTGGAAAA | 1950 |
| GAAGTACAAT GGAAGATGTA TGAGGTTTAT GATGCAAAAT CAAAATCTGT | 2000 |
| CAGTCTCCCA GTTCCAGACT TGTGTGCAGT CTATGCTGTT CAGGTGCGCT | 2050 |
| GTAAGAGGCT AGATGGACTG GGATATTGGA GTAATTGGAG CAATCCAGCC | 2100 |
| TACACAGTTG TCATGGATAT AAAAGTTCCT ATGAGAGGAC CTGAATTTTG | 2150 |
| GAGAATAATT AATGGAGATA CTATGAAAAA GGAGAAAAAT GTCACTTTAC | 2200 |
| TTTGGAAGCC CCTGATGAAA AATGACTCAT TGTGCAGTGT TCAGAGATAT | 2250 |
| GTGATAAACC ATCATACTTC CTGCAATGGA ACATGGTCAG AAGATGTGGG | 2300 |
| AAATCACACG AAATTCACTT TCCTGTGGAC AGAGCAAGCA CATACTGTTA | 2350 |
| CGGTTCTGGC CATCAATTCA ATTGGTGCTT CTGTTGCAAA TTTTAATTTA | 2400 |
| ACCTTTTCAT GGCCTATGAG CAAAGTAAAT ATCGTGCAGT CACTCAGTGC | 2450 |
| TTATCCTTTA AACAGCAGTT GTGTGATTGT TTCCTGGATA CTATCACCCA | 2500 |
| GTGATTACAA GCTAATGTAT TTTATTATTG AGTGGAAAAA TCTTAATGAA | 2550 |
| GATGGTGAAA TAAAATGGCT TAGAATCTCT TCATCTGTTA AGAAGTATTA | 2600 |
| TATCCATGAT CATTTTATCC CCATTGAGAA GTACCAGTTC AGTCTTTACC | 2650 |
| CAATATTTAT GGAAGGAGTG GGAAAACCAA AGATAATTAA TAGTTTCACT | 2700 |
| CAAGATGATA TTGAAAAACA CCAGAGTGAT GCAGGTTTAT ATGTAATTGT | 2750 |
| GCCAGTAATT ATTTCCTCTT CCATCTTATT GCTTGGAACA TTATTAATAT | 2800 |
| CACACCAAAG AATGAAAAAG CTATTTTGGG AAGATGTTCC GAACCCCAAG | 2850 |
| AATTGTTCCT GGGCACAAGG ACTTAATTTT CAGAAGAGAA CGGACATTCT | 2900 |
| TTGAAGTCTA ATCATGATCA CTACAGATGA ACCCAATGTG CCAACTTCCC | 2950 |
| AACAGTCTAT AGAGTATTAG AAGATTTTTA CATTTTGAAG AAGGGCCGGA | 3000 |
| ATTC | 3004 |

(2) INFORMATION FOR SEQ ID NO:6:

(i) SEQUENCE CHARACTERISTICS:
        (A) LENGTH: 3102 base pairs
        (B) TYPE: Nucleic Acid
        (C) STRANDEDNESS: Single
        (D) TOPOLOGY: Linear (xi) SEQUENCE DESCRIPTION: SEQ ID NO:6:

| | |
|---|---|
| GAATTCTCGA GTCGACGGCG GGCGTTAAAG CTCTCGTGGC ATTATCCTTC | 50 |
| AGTGGGGCTA TTGGACTGAC TTTTCTTATG CTGGGATGTG CCTTAGAGGA | 100 |
| TTATGGGTGT ACTTCTCTGA AGTAAGATGA TTTGTCAAAA ATTCTGTGTG | 150 |
| GTTTTGTTAC ATTGGGAATT TATTTATGTG ATAACTGCGT TTAACTTGTC | 200 |
| ATATCCAATT ACTCCTTGGA GATTTAAGTT GTCTTGCATG CCACCAAATT | 250 |
| CAACCTATGA CTACTTCCTT TTGCCTGCTG GACTCTCAAA GAATACTTCA | 300 |
| AATTCGAATG GACATTATGA GACAGCTGTT GAACCTAAGT TTAATTCAAG | 350 |
| TGGTACTCAC TTTTCTAACT TATCCAAAAC AACTTTCCAC TGTTGCTTTC | 400 |
| GGAGTGAGCA AGATAGAAAC TGCTCCTTAT GTGCAGACAA CATTGAAGGA | 450 |
| AAGACATTTG TTTCAACAGT AAATTCTTTA GTTTTTCAAC AAATAGATGC | 500 |

| | |
|---|---|
| AAACTGGAAC ATACAGTGCT GGCTAAAAGG AGACTTAAAA TTATTCATCT | 550 |
| GTTATGTGGA GTCATTATTT AAGAATCTAT TCAGGAATTA TAACTATAAG | 600 |
| GTCCATCTTT TATATGTTCT GCCTGAAGTG TTAGAAGATT CACCTCTGGT | 650 |
| TCCCCAAAAA GGCAGTTTTC AGATGGTTCA CTGCAATTGC AGTGTTCATG | 700 |
| AATGTTGTGA ATGTCTTGTG CCTGTGCCAA CAGCCAAACT CAACGACACT | 750 |
| CTCCTTATGT GTTTGAAAAT CACATCTGGT GGAGTAATTT TCCAGTCACC | 800 |
| TCTAATGTCA GTTCAGCCCA TAAATATGGT GAAGCCTGAT CCACCATTAG | 850 |
| GTTTGCATAT GGAAATCACA GATGATGGTA ATTTAAAGAT TTCTTGGTCC | 900 |
| AGCCCACCAT TGGTACCATT TCCACTTCAA TATCAAGTGA AATATTCAGA | 950 |
| GAATTCTACA ACAGTTATCA GAGAAGCTGA CAAGATTGTC TCAGCTACAT | 1000 |
| CCCTGCTAGT AGACAGTATA CTTCCTGGGT CTTCGTATGA GGTTCAGGTG | 1050 |
| AGGGGCAAGA GACTGGATGG CCCAGGAATC TGGAGTGACT GGAGTACTCC | 1100 |
| TCGTGTCTTT ACCACACAAG ATGTCTATA CTTTCCACCT AAAATTCTGA | 1150 |
| CAAGTGTTGG GTCTAATGTT TCTTTTCACT GCATCTATAA GAAGGAAAAC | 1200 |
| AAGATTGTTC CCTCAAAAGA GATTGTTTGG TGGATGAATT TAGCTGAGAA | 1250 |
| AATTCCTCAA AGCCAGTATG ATGTTGTGAG TGATCATGTT AGCAAAGTTA | 1300 |
| CTTTTTTCAA TCTGAATGAA ACCAAACCTC GAGGAAAGTT TACCTATGAT | 1350 |
| GCAGTGTACT GCTGCAATGA ACATGAATGC CATCATCGCT ATGCTGAATT | 1400 |
| ATATGTGATT GATGTCAATA TCAATATCTC ATGTGAAACT GATGGGTACT | 1450 |
| TAACTAAAAT GACTTGCAGA TGGTCAACCA GTACAATCCA GTCACTTGCG | 1500 |
| GAAAGCACTT TGCAATTGAG GTATCATAGG AGCAGCCTTT ACTGTTCTGA | 1550 |
| TATTCCATCT ATTCATCCCA TATCTGAGCC CAAAGATTGC TATTTGCAGA | 1600 |
| GTGATGGTTT TTATGAATGC ATTTTCCAGC CAATCTTCCT ATTATCTGGC | 1650 |
| TACACAATGT GGATTAGGAT CAATCACTCT CTAGGTTCAC TTGACTCTCC | 1700 |
| ACCAACATGT GTCCTTCCTG ATTCTGTGGT GAAGCCACTG CCTCCATCCA | 1750 |
| GTGTGAAAGC AGAAATTACT ATAAACATTG GATTATTGAA AATATCTTGG | 1800 |
| GAAAAGCCAG TCTTTCCAGA GAATAACCTT CAATTCCAGA TTCGCTATGG | 1850 |
| TTTAAGTGGA AAAGAAGTAC AATGGAAGAT GTATGAGGTT TATGATGCAA | 1900 |
| AATCAAAATC TGTCAGTCTC CCAGTTCCAG ACTTGTGTGC AGTCTATGCT | 1950 |
| GTTCAGGTGC GCTGTAAGAG GCTAGATGGA CTGGGATATT GGAGTAATTG | 2000 |
| GAGCAATCCA GCCTACACAG TTGTCATGGA TATAAAAGTT CCTATGAGAG | 2050 |
| GACCTGAATT TTGGAGAATA ATTAATGGAG ATACTATGAA AAAGGAGAAA | 2100 |
| AATGTCACTT TACTTTGGAA GCCCCTGATG AAAAATGACT CATTGTGCAG | 2150 |
| TGTTCAGAGA TATGTGATAA ACCATCATAC TTCCTGCAAT GGAACATGGT | 2200 |
| CAGAAGATGT GGGAAATCAC ACGAAATTCA CTTTCCTGTG GACAGAGCAA | 2250 |
| GCACATACTG TTACGGTTCT GGCCATCAAT TCAATTGGTG CTTCTGTTGC | 2300 |
| AAATTTTAAT TTAACCTTTT CATGGCCTAT GAGCAAAGTA AATATCGTGC | 2350 |
| AGTCACTCAG TGCTTATCCT TTAAACAGCA GTTGTGTGAT TGTTTCCTGG | 2400 |
| ATACTATCAC CCAGTGATTA CAAGCTAATG TATTTTATTA TTGAGTGGAA | 2450 |
| AAATCTTAAT GAAGATGGTG AAATAAAATG GCTTAGAATC TCTTCATCTG | 2500 |

-continued

```
TTAAGAAGTA TTATATCCAT GATCATTTTA TCCCCATTGA GAAGTACCAG        2550

TTCAGTCTTT ACCCAATATT TATGGAAGGA GTGGGAAAAC CAAAGATAAT        2600

TAATAGTTTC ACTCAAGATG ATATTGAAAA ACACCAGAGT GATGCAGGTT        2650

TATATGTAAT TGTGCCAGTA ATTATTTCCT CTTCCATCTT ATTGCTTGGA        2700

ACATTATTAA TATCACACCA AAGAATGAAA AAGCTATTTT GGGAAGATGT        2750

TCCGAACCCC AAGAATTGTT CCTGGGCACA AGGACTTAAT TTTCAGAAGA        2800

TGTTCCGAAC CCAAGAATT GTTCCTGGGC ACAAGGACTT AATTTTCAGA         2850

AGATGCTTGA AGGCAGCATG TTCGTTAAGA GTCATCACCA CTCCCTAATC        2900

TCAAGTACCC AGGGACACAA ACACTGCGGA AGGCCACAGG GTCCTCTGCA        2950

TAGGAAAACC AGAGACCTTT GTTCACTTGT TTATCTGCTG ACCCTCCCTC        3000

CACTATTGTC CTATGACCCT GCCAAATCCC CCTCTGTGAG AAACACCCAA        3050

GAATGATCAA TAAAAAAAAA AAAAAAAAA AAAAAAGTCG ACTCGAGAAT         3100

TC                                                            3102
```

(2) INFORMATION FOR SEQ ID NO:7:

(i) SEQUENCE CHARACTERISTICS:
        (A) LENGTH: 783 amino acids
        (B) TYPE: Amino Acid
        (D) TOPOLOGY: Linear (xi) SEQUENCE DESCRIPTION: SEQ ID NO:7:

```
Met Met Cys Gln Lys Phe Tyr Val Val Leu Leu His Trp Glu Phe
 1               5                  10                  15

Leu Tyr Val Ile Ala Ala Leu Asn Leu Ala Tyr Pro Ile Ser Pro
                20                  25                  30

Trp Lys Phe Lys Leu Phe Cys Gly Pro Pro Asn Thr Thr Asp Asp
                35                  40                  45

Ser Phe Leu Ser Pro Ala Gly Ala Pro Asn Asn Ala Ser Ala Leu
                50                  55                  60

Lys Gly Ala Ser Glu Ala Ile Val Glu Ala Lys Phe Asn Ser Ser
                65                  70                  75

Gly Ile Tyr Val Pro Glu Leu Ser Lys Thr Val Phe His Cys Cys
                80                  85                  90

Phe Gly Asn Glu Gln Gly Gln Asn Cys Ser Ala Leu Thr Asp Asn
                95                  100                 105

Thr Glu Gly Lys Thr Leu Ala Ser Val Val Lys Ala Ser Val Phe
                110                 115                 120

Arg Gln Leu Gly Val Asn Trp Asp Ile Glu Cys Trp Met Lys Gly
                125                 130                 135

Asp Leu Thr Leu Phe Ile Cys His Met Glu Pro Leu Pro Lys Asn
                140                 145                 150

Pro Phe Lys Asn Tyr Asp Ser Lys Val His Leu Leu Tyr Asp Leu
                155                 160                 165

Pro Glu Val Ile Asp Asp Ser Pro Leu Pro Leu Lys Asp Ser
                170                 175                 180

Phe Gln Thr Val Gln Cys Asn Cys Ser Leu Arg Gly Cys Glu Cys
                185                 190                 195

His Val Pro Val Pro Arg Ala Lys Leu Asn Tyr Ala Leu Leu Met
                200                 205                 210
```

```
Tyr Leu Glu Ile Thr Ser Ala Gly Val Ser Phe Gln Ser Pro Leu
            215                 220                 225

Met Ser Leu Gln Pro Met Leu Val Val Lys Pro Asp Pro Pro Leu
            230                 235                 240

Gly Leu His Met Glu Val Thr Asp Asp Gly Asn Leu Lys Ile Ser
            245                 250                 255

Trp Asp Ser Gln Thr Met Ala Pro Phe Pro Leu Gln Tyr Gln Val
            260                 265                 270

Lys Tyr Leu Glu Asn Ser Thr Ile Val Arg Glu Ala Ala Glu Ile
            275                 280                 285

Val Ser Ala Thr Ser Leu Leu Val Asp Ser Val Leu Pro Gly Ser
            290                 295                 300

Ser Tyr Glu Val Gln Val Arg Ser Lys Arg Leu Asp Gly Ser Gly
            305                 310                 315

Val Trp Ser Asp Trp Ser Ser Pro Gln Val Phe Thr Thr Gln Asp
            320                 325                 330

Val Val Tyr Phe Pro Pro Lys Ile Leu Thr Ser Val Gly Ser Asn
            335                 340                 345

Ala Ser Phe His Cys Ile Tyr Lys Asn Glu Asn Gln Ile Val Ser
            350                 355                 360

Ser Lys Gln Ile Val Trp Trp Arg Asn Leu Ala Glu Lys Ile Pro
            365                 370                 375

Glu Ile Gln Tyr Ser Ile Val Ser Asp Arg Val Ser Lys Val Thr
            380                 385                 390

Phe Ser Asn Leu Lys Ala Thr Arg Pro Arg Gly Lys Phe Thr Tyr
            395                 400                 405

Asp Ala Val Tyr Cys Cys Asn Glu Gln Ala Cys His His Arg Tyr
            410                 415                 420

Ala Glu Leu Tyr Val Ile Asp Val Asn Ile Asn Ile Ser Cys Glu
            425                 430                 435

Thr Asp Gly Tyr Leu Thr Lys Met Thr Cys Arg Trp Ser Pro Ser
            440                 445                 450

Thr Ile Gln Ser Leu Val Gly Ser Thr Val Gln Leu Arg Tyr His
            455                 460                 465

Arg Cys Ser Leu Tyr Cys Pro Asp Ser Pro Ser Ile His Pro Thr
            470                 475                 480

Ser Glu Pro Lys Thr Ala Ser Tyr Arg Glu Thr Ala Phe Met Asn
            485                 490                 495

Val Phe Ser Ser Gln Ser Phe Tyr Tyr Leu Ala Ile Gln Cys Gly
            500                 505                 510

Phe Arg Ile Asn His Ser Leu Gly Ser Leu Asp Ser Pro Pro Thr
            515                 520                 525

Cys Val Leu Pro Asp Ser Val Val Lys Pro Leu Pro Pro Ser Asn
            530                 535                 540

Val Lys Ala Glu Ile Thr Val Asn Thr Gly Leu Leu Lys Val Ser
            545                 550                 555

Trp Glu Lys Pro Val Phe Pro Glu Asn Asn Leu Gln Phe Gln Ile
            560                 565                 570

Arg Tyr Gly Leu Ser Gly Lys Glu Ile Gln Trp Lys Thr His Glu
            575                 580                 585

Val Phe Asp Ala Lys Ser Lys Ser Ala Ser Leu Leu Val Ser Asp
            590                 595                 600
```

-continued

```
Leu Cys Ala Val Tyr Val Val Gln Val Arg Cys Arg Arg Leu Asp
            605                 610                 615

Gly Leu Gly Tyr Trp Ser Asn Trp Ser Ser Pro Ala Tyr Thr Leu
            620                 625                 630

Val Met Asp Val Lys Val Pro Met Arg Gly Pro Glu Phe Trp Arg
            635                 640                 645

Lys Met Asp Gly Asp Val Thr Lys Lys Glu Arg Asn Val Thr Leu
            650                 655                 660

Leu Trp Lys Pro Leu Thr Lys Asn Asp Ser Leu Cys Ser Val Arg
            665                 670                 675

Arg Tyr Val Val Lys His Arg Thr Ala His Asn Gly Thr Trp Ser
            680                 685                 690

Glu Asp Val Gly Asn Arg Thr Asn Leu Thr Phe Leu Trp Thr Glu
            695                 700                 705

Pro Ala His Thr Val Thr Val Leu Ala Val Asn Ser Leu Gly Ala
            710                 715                 720

Ser Leu Val Asn Phe Asn Leu Thr Phe Ser Trp Pro Met Ser Lys
            725                 730                 735

Val Ser Ala Val Glu Ser Leu Ser Ala Tyr Pro Leu Ser Ser Ser
            740                 745                 750

Cys Val Ile Leu Ser Trp Thr Leu Ser Pro Asp Asp Tyr Ser Leu
            755                 760                 765

Leu Tyr Leu Val Ile Glu Trp Lys Ile Leu Asn Glu Asp Asp Gly
            770                 775                 780

Met Lys Trp
     783
```

(2) INFORMATION FOR SEQ ID NO:8:

(i) SEQUENCE CHARACTERISTICS:
        (A) LENGTH: 2868 base pairs
        (B) TYPE: Nucleic Acid
        (C) STRANDEDNESS: Single
        (D) TOPOLOGY: Linear (xi) SEQUENCE DESCRIPTION: SEQ ID NO:8:

```
GGGCCCCCCC TCGAAGTCGA CGGTATCGAT AAGCTTGATA TCGAATTCCG           50

GCCGGGACAC AGGTGGGACA CTCTTTTAGT CCTCAATCCC TGGCGCGAGG          100

CCACCCAAGG CAACGCAGGA CGCAGGGCGT TTGGGGACCA GGCAGCAGAC          150

TGGGGCGGTA CCTGCGGAGA GCCACGCAAC TTCTCCAGGC CTCTGACTAC          200

TTTGGAAACT GCCCGGGGCT GCGACATCAA CCCCTTAAGT CCCGGAGGCG          250

GAAAGAGGGT GGGTTGGTTT GAAAGACACA AGGAAGAAAA ATGTGCTGTG          300

GGGCGGGTTA AGTTTCCCAC CCTCTTCCCC CTTCCCGAGC AAATTAGAAA          350

CAAAACAAAT AGAAAGCCA GCCCTCCGGC CAACCAAAGC CCCAAGCGGA          400

GCCCCAAGCG GAGCCCCAGC CGGAGCACTC CTTTAAAAGG ATTTGCAGCG          450

GTGAGGAAAA AACCAGACCC GACCGAGGAA TCGTTCTGCA AATCCAGGTG          500

TACACCTCTG AAGAAAGATG ATGTGTCAGA AATTCTATGT GGTTTTGTTA          550

CACTGGGAAT TCTTTATGT GATAGCTGCA CTTAACCTGG CATATCCAAT           600

CTCTCCCTGG AAATTTAAGT TGTTTTGTGG ACCACCGAAC ACAACCGATG          650

ACTCCTTTCT CTCACCTGCT GGAGCCCCAA ACAATGCCTC GGCTTTGAAG          700

GGGGCTTCTG AAGCAATTGT TGAAGCTAAA TTTAATTCAA GTGGTATCTA          750
```

-continued

```
CGTTCCTGAG TTATCCAAAA CAGTCTTCCA CTGTTGCTTT GGGAATGAGC        800

AAGGTCAAAA CTGCTCTGCA CTCACAGACA ACACTGAAGG GAAGACACTG        850

GCTTCAGTAG TGAAGGCTTC AGTTTTTCGC CAGCTAGGTG TAAACTGGGA        900

CATAGAGTGC TGGATGAAAG GGGACTTGAC ATTATTCATC TGTCATATGG        950

AGCCATTACC TAAGAACCCC TTCAAGAATT ATGACTCTAA GGTCCATCTT       1000

TTATATGATC TGCCTGAAGT CATAGATGAT TCGCCTCTGC CCCCACTGAA       1050

AGACAGCTTT CAGACTGTCC AATGCAACTG CAGTCTTCGG GGATGTGAAT       1100

GTCATGTGCC AGTACCCAGA GCCAAACTCA ACTACGCTCT TCTGATGTAT       1150

TTGGAAATCA CATCTGCCGG TGTGAGTTTT CAGTCACCTC TGATGTCACT       1200

GCAGCCCATG CTTGTTGTGA AACCCGATCC ACCCTTAGGT TTGCATATGG       1250

AAGTCACAGA TGATGGTAAT TTAAAGATTT CTTGGGACAG CCAAACAATG       1300

GCACCATTTC CGCTTCAATA TCAGGTGAAA TATTTAGAGA ATTCTACAAT       1350

TGTAAGAGAG GCTGCTGAAA TTGTCTCAGC TACATCTCTG CTGGTAGACA       1400

GTGTGCTTCC TGGATCTTCA TATGAGGTCC AGGTGAGGAG CAAGAGACTG       1450

GATGGTTCAG GAGTCTGGAG TGACTGGAGT TCACCTCAAG TCTTTACCAC       1500

ACAAGATGTT GTGTATTTTC CACCCAAAAT TCTGACTAGT GTTGGATCGA       1550

ATGCTTCCTT TCATTGCATC TACAAAAACG AAAACCAGAT TGTCTCCTCA       1600

AAACAGATAG TTTGGTGGAG GAATCTAGCT GAGAAAATCC CTGAGATACA       1650

GTACAGCATT GTGAGTGACC GAGTTAGCAA AGTTACCTTC TCCAACCTGA       1700

AAGCCACCAG ACCTCGAGGG AAGTTTACCT ATGACGCAGT GTACTGCTGC       1750

AATGAGCAGG CGTGCCATCA CCGCTATGCT GAATTATACG TGATCGATGT       1800

CAATATCAAT ATATCATGTG AAACTGACGG GTACTTAACT AAAATGACTT       1850

GCAGATGGTC ACCCAGCACA ATCCAATCAC TAGTGGGAAG CACTGTGCAG       1900

CTGAGGTATC ACAGGTGCAG CCTGTATTGT CCTGATAGTC CATCTATTCA       1950

TCCTACGTCT GAGCCCAAAA CTGCGTCTTA CAGAGAGACG GCTTTTATGA       2000

ATGTGTTTTC CAGCCAATCT TTCTATTATC TGGCTATACA ATGTGGATTC       2050

AGGATCAACC ATTCTTTAGG TTCACTTGAC TCGCCACCAA CGTGTGTCCT       2100

TCCTGACTCC GTAGTAAAAC CACTACCTCC ATCTAACGTA AAAGCAGAGA       2150

TTACTGTAAA CACTGGATTA TTGAAAGTAT CTTGGGAAAA GCCAGTCTTT       2200

CCGGAGAATA ACCTTCAATT CCAGATTCGA TATGGCTTAA GTGGAAAAGA       2250

AATACAATGG AAGACACATG AGGTATTCGA TGCAAAGTCA AAGTCTGCCA       2300

GCCTGCTGGT GTCAGACCTC TGTGCAGTCT ATGTGGTCCA GGTTCGCTGC       2350

CGGCGGTTGG ATGGACTAGG ATATTGGAGT AATTGGAGCA GTCCAGCCTA       2400

TACGCTTGTC ATGGATGTAA AAGTTCCTAT GAGAGGGCCT GAATTTGGA        2450

GAAAAATGGA TGGGGACGTT ACTAAAAAGG AGAGAAATGT CACCTTGCTT       2500

TGGAAGCCCC TGACGAAAAA TGACTCACTG TGTAGTGTGA GGAGGTACGT       2550

GGTGAAGCAT CGTACTGCCC ACAATGGGAC GTGGTCAGAA GATGTGGGAA       2600

ATCGGACCAA TCTCACTTTC CTGTGGACAG AACCAGCGCA CACTGTTACA       2650

GTTCTGGCTG TCAATTCCCT CGGCGCTTCC CTTGTGAATT TTAACCTTAC       2700

CTTCTCATGG CCCATGAGTA AAGTGAGTGC TGTGGAGTCA CTCAGTGCTT       2750
```

| | |
|---|---|
| ATCCCCTGAG CAGCAGCTGT GTCATCCTTT CCTGGACACT GTCACCTGAT | 2800 |
| GATTATAGTC TGTTATATCT GGTTATTGAA TGGAAGATCC TTAATGAAGA | 2850 |
| TGATGGAATG AAGTGGCT | 2868 |

(2) INFORMATION FOR SEQ ID NO:9:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:9:

| | |
|---|---|
| GGGTTAAGTT TCCCACCC | 18 |

(2) INFORMATION FOR SEQ ID NO:10:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:10:

| | |
|---|---|
| GGGTGGGAAA CTTAACCC | 18 |

(2) INFORMATION FOR SEQ ID NO:11:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:11:

| | |
|---|---|
| AGGATACAGT GGGATCCC | 18 |

(2) INFORMATION FOR SEQ ID NO:12:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:12:

| | |
|---|---|
| GCCCGAGCAC TCCTTTAA | 18 |

(2) INFORMATION FOR SEQ ID NO:13:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:13:

| | |
|---|---|
| TTAAAGGAGT GCTCCCGC | 18 |

(2) INFORMATION FOR SEQ ID NO:14:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:14:

GAGCGGCCCT GTTAGATA                                                   18

(2) INFORMATION FOR SEQ ID NO:15:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:15:

GTATACACCT CTGAAGAA                                                   18

(2) INFORMATION FOR SEQ ID NO:16:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:16:

TTCTTCAGAG GTGTACAC                                                   18

(2) INFORMATION FOR SEQ ID NO:17:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:17:

ATGCGAGGCT ACTTCTAT                                                   18

(2) INFORMATION FOR SEQ ID NO:18:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:18:

CTCTCCCTGG AAATTTAA                                                   18

(2) INFORMATION FOR SEQ ID NO:19:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:19:

TTAAATTTCC AGGGAGAG                                                   18

(2) INFORMATION FOR SEQ ID NO:20:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (xi) SEQUENCE DESCRIPTION: SEQ ID NO:20:

ATTTGAAGGA GTTAAGCC                                              18

(2) INFORMATION FOR SEQ ID NO:21:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:21:

AATTTAATTC AAGTGGTA                                              18

(2) INFORMATION FOR SEQ ID NO:22:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:22:

TACCAGTTGA ATTAAATT                                              18

(2) INFORMATION FOR SEQ ID NO:23:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:23:

GTATCACTTC ATAATATA                                              18

(2) INFORMATION FOR SEQ ID NO:24:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:24:

GATGGTCAGG GTGAACTG                                              18

(2) INFORMATION FOR SEQ ID NO:25:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:25:

CAGTTCACCC TGACCATC                                              18

(2) INFORMATION FOR SEQ ID NO:26:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:26:

GAGGCGAATG TGCGGATT                                                     18

(2) INFORMATION FOR SEQ ID NO:27:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:27:

CTTAAATCTC CAAGGAGT                                                     18

(2) INFORMATION FOR SEQ ID NO:28:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:28:

ACTCCTTGGA GATTTAAG                                                     18

(2) INFORMATION FOR SEQ ID NO:29:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:29:

AAGTCTTAAG CCAGACTT                                                     18

(2) INFORMATION FOR SEQ ID NO:30:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:30:

TCTAAGGCAC ATCCCAGC                                                     18

(2) INFORMATION FOR SEQ ID NO:31:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:31:

GCTGGGATGT GCCTTAGA                                                     18

(2) INFORMATION FOR SEQ ID NO:32:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:32:

CGCAATGAAT TGACCCCC                                          18

(2) INFORMATION FOR SEQ ID NO:33:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:33:

TACTTCAGAG AAGTACAC                                          18

(2) INFORMATION FOR SEQ ID NO:34:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:34:

GTGTACTTCT CTGAAGTA                                          18

(2) INFORMATION FOR SEQ ID NO:35:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:35:

GAATCACGGT AACTATCA                                          18

(2) INFORMATION FOR SEQ ID NO:36:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:36:

CAGCTGTCTC ATAATGTC                                          18

(2) INFORMATION FOR SEQ ID NO:37:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:37:

GACATTATGA GACAGCTG                                          18

(2) INFORMATION FOR SEQ ID NO:38:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:38:

TTCGTCAAGC CATCTGAT                                           18

(2) INFORMATION FOR SEQ ID NO:39:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:39:

His Gln Asn Leu Ser Asp Gly Lys
 1               5           8

(2) INFORMATION FOR SEQ ID NO:40:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:40:

His Gln Asn Ile Ser Asp Gly Lys
 1               5           8

(2) INFORMATION FOR SEQ ID NO:41:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO:41:

His Gln Ser Leu Gly Thr Gln
 1               5       7

(2) INFORMATION FOR SEQ ID NO:42:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO:42:

Val Ile Ser Ser His Leu Gly Gln
 1               5           8

(2) INFORMATION FOR SEQ ID NO:43:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO:43:

Pro Lys Asn Ser Ser Met Ile Ser Asn Thr Pro
 1               5                  10  11

(2) INFORMATION FOR SEQ ID NO:44:

(i) SEQUENCE CHARACTERISTICS:
        (A) LENGTH: 10 amino acids
        (B) TYPE: Amino Acid
        (D) TOPOLOGY: Linear

```
    (xi) SEQUENCE DESCRIPTION: SEQ ID NO:44:

Asp Lys Thr His Thr Cys Pro Pro Cys Pro
 1               5                   10

(2) INFORMATION FOR SEQ ID NO:45:

(i) SEQUENCE CHARACTERISTICS:
        (A) LENGTH: 51 base pairs
        (B) TYPE: Nucleic Acid
        (C) STRANDEDNESS: Single
        (D) TOPOLOGY: Linear (xi) SEQUENCE DESCRIPTION: SEQ ID NO:45:

GTCAGTCTCC CAGTTCCAGA CTTGTGTGCA GTCTATGCTG TTCAGGTGCG              50

C                                                                  51
```